(12) United States Patent
Hol et al.

(10) Patent No.: US 10,632,122 B2
(45) Date of Patent: *Apr. 28, 2020

(54) COMPOSITIONS AND METHODS FOR TREATING TOXOPLASMOSIS, CRYPTOSPORIDIOSIS AND OTHER APICOMPLEXAN PROTOZOAN RELATED DISEASES

(71) Applicant: University of Washington, Seattle, WA (US)

(72) Inventors: Wilhelmus G. J. Hol, Seattle, WA (US); Eric T. Larson, Seattle, WA (US); Dustin James Maly, Seattle, WA (US); Wesley C. Van Voorhis, Seattle, WA (US); Ethan Merritt, Seattle, WA (US); Kayode K. Ojo, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/402,227

(22) Filed: May 2, 2019

(65) Prior Publication Data

US 2019/0358231 A1 Nov. 28, 2019

Related U.S. Application Data

(63) Continuation of application No. 15/544,606, filed as application No. PCT/US2016/014996 on Jan. 26, 2016, now Pat. No. 10,307,425.

(60) Provisional application No. 62/107,746, filed on Jan. 26, 2015, provisional application No. 62/131,539, filed on Mar. 11, 2015.

(51) Int. Cl.
| | | |
|---|---|---|
| C07D 487/04 | (2006.01) | |
| A61K 31/519 | (2006.01) | |
| A61K 31/4985 | (2006.01) | |
| A61P 35/00 | (2006.01) | |
| A61P 33/02 | (2006.01) | |

(52) U.S. Cl.
CPC ........ A61K 31/519 (2013.01); A61K 31/4985 (2013.01); A61P 33/02 (2018.01); A61P 35/00 (2018.01); C07D 487/04 (2013.01); Y02A 50/411 (2018.01); Y02A 50/488 (2018.01)

(58) Field of Classification Search
CPC .......................... A61K 31/519; C07D 487/04
See application file for complete search history.

(56) References Cited

U.S. PATENT DOCUMENTS

| 10,307,425 B2* | 6/2019 | Hol ...................... C07D 487/04 |
|---|---|---|
| 2003/0187001 A1 | 10/2003 | Calderwood |
| 2006/0235031 A1 | 10/2006 | Arnold et al. |
| 2008/0014200 A1 | 1/2008 | Arnold |
| 2013/0018040 A1 | 1/2013 | Van Voorhis et al. |

FOREIGN PATENT DOCUMENTS

| DE | 102004063269 A1 | 7/2006 |
|---|---|---|
| WO | 2008/074997 A1 | 6/2008 |
| WO | 2009/150230 A1 | 12/2009 |
| WO | 2011/057064 A1 | 5/2011 |
| WO | 2011/094628 A1 | 8/2011 |
| WO | 2012/078859 A2 | 6/2012 |

OTHER PUBLICATIONS

Ajjampur et al., "Closing the diarrhea diagnostic gap in Indian children by the application of molecular techniques," J. Med. Microbiol. 57(Pt 11): 1364-1368 (2008).
Apsel et al., "Targeted polypharmacology: discovery of dual inhibitors of tyrosine and phosphoinositide kinases," Nat. Chem. Biol., 4(11): 691-699 (2008).
Billker et al., "Calcium-dependent signaling and kinases in apicomplexan parasites," Cell Host Microbe. 5(6):612-22 (2009).
Bishop et al., "A chemical switch for inhibitor-sensitive alleles of any protein kinase," Nature 407(6802): 395-401 (2000).
Bishop et al., "Design of allele-specific inhibitors to probe protein kinase signaling," Curr. Biol. 8(5): 257-266 (1998).
Bishop et al., "Generation of monospecific nanomolar tyrosine kinase inhibitors via a chemical genetic approach," J. Am. Chem. Soc. 121(4): 627-631 (1999).
Burchat et al., "Pyrazolo[3,4-d]pyrimidines containing an extended 3-substituent as potent inhibitors of Lck—a selectivity insight," Bioorg. Med. Chem. Lett., 12(12): 1687-1690 (2002).
Castellanos-Gonzalez et al., "A novel calcium dependent protein kinase inhibitor as a lead compound for treating cryptosporidiosis," J. Infect. Dis. 208(8):1342-1348 (2013).

(Continued)

*Primary Examiner* — D Margaret M Seaman
(74) *Attorney, Agent, or Firm* — McDonnell Boehnen Hulbert & Berghoff LLP

(57) ABSTRACT

The present disclosure is directed to compositions and methods for inhibiting either *Toxoplasma gondii* (*T. gondii*) calcium dependent protein kinases (TgCDPKs) or *Cryptosporidium parvum* (*C. parvum*) and *Cryptosporidium hominus* (*C. hominus*) calcium dependent protein kinases (CpCDPKs) using pyrazolopyrimidine and/or imidazo[1,5-a]pyrazine inhibitors, of the Formula (I), wherein the variables X, Y, Z, $R^1$, and $R^3$ are defined herein.

20 Claims, 5 Drawing Sheets

(56) References Cited

OTHER PUBLICATIONS

Chen et al., "Apical Organelle discharge by *Cryptosporidium parvum* is temperature, cytoskeleton, and intracellular calcium dependent and required for host cell invasion," Infect. Immun. 72(12): 6806-16 (2004).
Chen et al., "Protein kinase D3 (PKD3) contributes to prostate cancer cell growth and survival through a PKCepsilon/ PKD3 pathway downstream of Akt and ERK 1/2". Cancer Res. 68(10):3844-53 (2008).
Cohen et al., "Structural bioinformatics-based design of selective, irreversible kinase inhibitors," Science 308(5726): 1318-1321 (2005).
Demar et al. "Acute toxoplasmoses in immunocompetent patients hospitalized in an intensive care unit in French Guiana," Clin. Microbiol. Infect. 18:E221-E231 (2012).
Deng et al., "PKD3 contributes to up-regulation of prostate-specific antigen in prostate cancer cells," Nan Fang Yi Ke Da Xue Xue Bao. 30(8):1779-82 (2010).
Doerig et al., "Protein kinases as targets for antimalarial intervention: kinomics, structure-based design, transmission-blockade, and targeting host cell enzymes," Biophysica et Biochimica Acta—Proteins and Proteomics 1754(1-2): 132-150 (2005).
Doggett et al., "Bumped Kinase Inhibitor 1294 Treats Established *Toxoplasma gondii* Infection," Antimicrob Agents Chemother 58(6):3547-9 (2014).
Gilbert et al., "Ocular sequelae of congenital toxoplasmosis in Brazil compared with Europe," PLoS Negl. Trop. Dis. 2(8):e277 (2008).
Hanke et al., "Discovery of a novel, potent, and Src family-selective tyrosine kinase Inhibitor: Study of Lck- and FynT-dependent T cell activation," J. Biol. Chem. 271(2): 695-701 (1996).
Hines et al., "Theileria equi isolates vary in susceptibility to imidocarb dipropionate but demonstrate uniform in vitro susceptibility to a bumped kinase inhibitor," Parasit Vectors. 8:33 (2015).
Huang et al., "SAR Studies of 5-Aminopyrazole-4-carboxamide Analogues as Potent and Selective Inhibitors of Toxoplasma gondii CDPK1," ACS Med Chem Lett. 6(12):1184-1189 (2015).
Johnson et al., "Development of Toxoplasma gondii calcium-dependent protein kinase 1 (TgCDPK1) inhibitors with potent anti-toxoplasma activity," J. Med. Chem. 55(5): 2416-2426 (2012).
Keyloun et al., "The gatekeeper residue and beyond: homologous calcium-dependent protein kinases as drug development targets for veterinarian Apicomplexa parasites," Parasitology. 141(11):1499-509 (2014).
Kieschnick et al., "Toxoplasma gondii attachment to host cells is regulated by a calmodulin-like domain protein kinase," J. Biol. Chem. 276(15): 12369-12377 (2001).
Larson et al., "Multiple Determinants for Selective Inhibition of Apicomplexan Calcium-Dependent Protein Kinase CDPK1," Journal of Medicinal Chemistry 55(6):2803-10 (2012).
Lavalle et al., "Inducible silencing of protein kinase D3 inhibits secretion of tumor-promoting factors in prostatecancer," Mol Cancer Ther. 11(7):1389-99 (2012).
Lavalle et al., "Novel protein kinase D inhibitors cause potent arrest in prostate cancer cell growth and motility," BMC Chem Biol. 10:5 (2010).
Lender et al., "A novel CDPK1 inhibitor—a potential treatment for cryptosporidiosis in calves?" Parasitol Res. 114 (1):335-6 (2015).
Liao, JJ. "Molecular recognition of protein kinase binding pockets for design of potentand selective kinase inhibitors," J. Med. Chem. 50(3): 409-424 (2007).
Lourido et al. "Optimizing small molecule inhibitors of calcium-dependent protein kinase 1 to prevent infection by Toxoplasma gondii," J. Med. Chem. 56(7):3068-3077 (2013).
Lourido et al., "Calcium-dependent protein kinase 1 is an essential regulator of exocytosis in Toxoplasma," Nature 465 (7296):359-362 (2010).

Montoya et al., Chapter 276: Toxoplasma gondii in Mandell, Bennett, & Dolin: Principles and Practice of Infectious Diseases, 6th ed. Publ: Churchill Livingston (2005).
Murhpy et al., "Discovery of Potent and Selective Inhibitors of CDPK1 from C. parvum and T. gondii" ACS Med. Chem. Lett. 1(7): 331-335 (2010).
Nagamune and Sibley, "Comparative genomic and phylogenetic analyses of calcium ATPases and calcium-regulated proteins in the apicomplexa," Mol. Biol. Evol. 23(8): 1613-1627 (2006).
Ojo et al., "A specific inhibitor of PfCDPK4 blocks malaria transmission: Chemical-genetic validation," J. Infect. Dis. 209(2):275-284 (2014).
Ojo et al., "Neospora caninum Calcium-Dependent Protein Kinase 1 Is an Effective Drug Target for Neosporosis Therapy," PLoS One, 9(3):e92929 (2014).
Ojo et al., "Toxoplasma gondii calcium-dependent protein kinase 1 is a target for selective kinase inhibitors," Nat. Struct. Mol. Biol. 17(5):602-7 (2010).
Samie et al., "*Cryptosporidium* species: preliminary descriptions of the prevalence and genotype distribution among school children and hospital patients in the Venda region, Limpopo Province, South Africa," Exp.Parasitol. 114 (4):314-322 (2006).
Sugi et al., "1NM-PP1 treatment of mice infected with *Toxoplasma gondii*," J. Vet. Med. Sci. 73(10):1377-1379 (2011).
Sugi et al., "Identification of mutations in TgMAPK1 of Toxoplasma gondii conferring resistance to 1NM-PP1," Int. J. Parasitol. Drugs Drug Resist. 3:93-101 (2013).
Sugi et al., "Use of the kinase inhibitor analog 1NM-PP1 reveals a role for Toxoplasma gondii CDPK1 in the invasion step," Eukaryot. Cell 9(4): 667-70. (2010).
Tandon et al., "New Pyrazolopyrimidine Inhibitors of Protein Kinase D as Potent Anticancer Agents for Prostate Cancer," PLoS One. 8(9):e75601 (2013).
Valeur and Roche. "Efficient, mild, parallel and purification-free synthesis of arylethers via Mitsunobu reaction," Tet. Lett. 49(23): 4182-4185 (2008).
Vidadala, et al., "Development of potent and selective *Plasmodium falciparum* calcium-dependent protein kinase 4 (PfCDPK4) inhibitors that block the transmission of malaria to mosquitoes," Eur J Med Chem 74:562-73 (2014).
White AC., Jr. Chapter 280: Cryptosporidiosis (*Cryptosporidium hominis, Cryptosporidium parvum*, and Other Species) in Mandell, Bennett, & Dolin: Principles and Practice of Infectious Diseases, 6th ed. Publ: Churchill Livingston (2005).
Winzer et al. "In Vitro and In Vivo Effects of the Bumped Kinase Inhibitor 1294 in the Related Cyst-Forming Apicomplexans Toxoplasma gondii and Neospora caninum," Antimicrob Agents Chemother 59(10):6361-74 (2015).
Zhang et al., "A second-site suppressor strategy for chemical genetic analysis of diverse protein kinases," Nat. Methods 2(6): 435-441 (2005).
Zhang et al., "Benzoylbenzimidazole-based selective inhibitors targeting Cryptosporidium parvum and Toxoplasma gondii calcium-dependent protein kinase-1," Bioorg Med Chem Lett. 22(16):5264-7 (2012).
Zhang et al., "Potent and Selective Inhibitors of CDPK1 from T. gondii and C. parvum Based on a 5-Aminopyrazole-4-carboxamide Scaffold," ACS Med. Chem. Letters. 5(1): 40-44 (2013).
Zou et al., "Protein kinase D3 is involved in negative regulation of MMP-7 in prostate cancer cells," Nan Fang Yi Ke Da Xue Xue Bao. 30(8):1767-70 (2010).
Zou et al., "PKD2 and PKD3 promote prostate cancer cell invasion by modulating NF-κB- and HDAC1-mediated expression and activation of uPA," J Cell Sci. 125(Pt 20):4800-11 (2012).
The International Search Report (ISR) for PCT/US2016/014996 dated Mar. 4, 2016, pp. 1-3.
Written Opinion of the International Searching Authority for PCT/US2016/014996 dated Mar. 4, 2016, pates 1-5.
The International Search Report (ISR) for PCT/US2016/014995, 3 pages, dated Mar. 30, 2016.
International Preliminary Report on Patentability (IPRP) and Written Opinion of the International Searching Authority for PCT/US2016/014995, 11 pages, dated Aug. 1, 2017 and Mar. 30, 2016.

(56) References Cited

OTHER PUBLICATIONS

Ojo et al., "Transmission of malaria to mosquitoes blocked by bumped kinase inhibitors," J. Clin. Invest. 122(6):2301-2305 (2012).
Pedroni et al., "Bumped kinase inhibitor prohibits egression in Babesia bovis," Vet Parasitol 215:22-8 (2016).

* cited by examiner

A

B

… (1)

COMPOSITIONS AND METHODS FOR TREATING TOXOPLASMOSIS, CRYPTOSPORIDIOSIS AND OTHER APICOMPLEXAN PROTOZOAN RELATED DISEASES

CROSS-REFERENCE TO RELATED APPLICATIONS

This application is a continuation of U.S. patent application Ser. No. 15/544,606, filed Jul. 19, 2017, which is a U.S. national phase of International Application No. PCT/US2016/014996, filed on Jan. 26, 2016, which claims priority to U.S. Provisional Application No. 62/131,539, filed Mar. 11, 2015 and U.S. Provisional Application No. 62/107,746, filed Jan. 26, 2015, all of which are incorporated by reference herein in their entirety.

STATEMENT OF GOVERNMENT SUPPORT

This invention was made with government support under Grant Nos. 5 R01 AI089441-02, P01 AI067921, R01 AI050506, R01 AI080625 and R01 GM086858, awarded by the National Institutes of Health. The government has certain rights in the invention.

FIELD OF THE INVENTION

The present disclosure is generally directed to compositions and methods for treating apicomplexan protozoan related disease, such as toxoplasmosis and cryptosporidiosis.

BACKGROUND OF THE INVENTION

The apicomplexan protozoans *Cryptosporidium parvum* and *Toxoplasma gondii* are ubiquitous parasites that infect humans and domesticated animals. Recently *C. hominus* was recognized to be distinct from *C. parvum*, and does not appear to infect domesticated animals, but rather appears limited to human infections. *C. parvum* and *C. hominus* are infectious parasites of major health concern in humans as they are a common cause of illness transmitted by water. *C. parvum* and *C. hominus* infections result in debilitating diarrhea that can be life-threatening in immunocompromised patients.

Recent studies have implicated *Cryptosporidium* spp. in around 15-20% of childhood diarrheal disease in the developing world. Currently, nitazoxanide is the only approved therapy for cryptosporidiosis but it is expensive and has not been shown to be effective in treating immunocompromised hosts. *T. gondii* may be the most common infectious eukaryotic parasite in humans, based on sero-surveys. Transmitted primarily through undercooked meat or accidental ingestion of cat feces, *T. gondii* infection presents major health concerns in immunocompromised hosts, where it causes toxoplasmic encephalitis, and in pregnancy, where it can result in severe birth defects or miscarriage.

Sulfadiazine and pyrimethamine are the current therapies for toxoplasmosis, but they can cause nephrotoxicity, rash, and additional complications in pregnancy. Thus, new therapies for treating infections caused by both parasites are greatly needed. In *T. gondii*, calcium-regulated signaling is associated with a number of cellular functions such as secretion, gliding motility and host cell invasion. The proper control of intracellular calcium levels is important for host cell invasion and *T. gondii* use several mechanisms for the uptake and release of calcium. Furthermore, this organism contains specialized calcium-regulated signaling enzymes, including a unique family of calciumdependent protein kinases (CDPKs) which are present in plants, ciliates and green algae but not in animals. These kinases are believed to be mediators of secretion, invasion, and gliding motility. *T. gondii, C. parvum*, and *C. hominus* are highly related obligate intracellular parasites. While much less is known about the role of calcium signaling in *C. parvum* and *C. hominus*, it appears that many calcium-regulated signaling processes are conserved from *T. gondii* to *C. parvum. C. parvum* and *C. hominus* also possess CDPKs that are believed to play important roles in calcium-regulated processes and they are virtually identical in these two spp. Thus, inhibitors of *C. parvum* CDPKs would be expected to inhibit *C. hominus* CDPK.

SUMMARY OF THE INVENTION

We have recognized that the roles that CDPKs play in calcium signaling in *T. gondii, C. parvum* and *C. hominus* make this family of kinases intriguing targets for the development of anti-parasitic agents. Previous studies have demonstrated that TgCDPK1 plays an important role in *T. gondii* invasion of mammalian cells. Pharmacological agents that selectively inhibit the catalytic activity of TgCDPK1 block parasitic invasion of human fibroblast cells. Furthermore, we have demonstrated that a unique sequence and structural variation in the ATP-binding cleft of TgCDPK1 provides an opportunity to develop highly selective inhibitors of this kinase (the U.S. Patent Publication 2013/0018040). Specifically, TgCDPK1 contains a glycine residue at the "gatekeeper" position which allows inhibitors to access a large hydrophobic pocket that is adjacent to the site of ATP binding (Hydrophobic Pocket II).

The present disclosure is generally directed to compositions and methods for the treatment of apicomplexan-related disorders, including but not limited to toxoplasmosis, caused by the infectious eukaryotic parasite *Toxoplasma gondii* (*T. gondii*), cryptosporidiosis, caused by the infectious eukaryotic parasites *Cryptosporidium parvum* (*C. parvum*) and *Cryptosporidium hominus* (*C. hominus*), malaria, caused by the eukaryotic parasites *Plasmodium falciparum* (*P. falciparum*), *Plasmodium vivax* (*P. vivax*), and *Plasmodium berghei* (*P. berghei*), neosporosis, caused by the eukaryotic parasite *Neospora caninum*, sarcocystosis, caused by the eukaryotic parasite *Sarcocystis neuronae* and other species, besnoitiosis, (originally named globidiosis) caused by *Besnoitia besnoiti*, coccidiosis, caused by *Hammondia hammondi* and other *Hammondia* spp., cystoisoporosis, caused by the eukaryotic parasitic species *Cystoisoporosis suis* and other species, babesiosis, caused by the eukaryotic parasites *Babesia microtii* and other species, and theileriosis, caused by the eukaryotic parasites *Theileria equi* and other species. Because all known human kinases possess larger residues (threonine, valine or a larger amino acid) at the gatekeeper position, the inventors have recognized that it is possible to gain selectivity by developing inhibitors that optimize interactions with the enlarged ATP-binding pocket of TgCDPK1. In one embodiment, the present disclosure is directed to compositions and methods for inhibiting apicomplexan calcium dependent protein kinases, including but not limited to *T. gondii* calcium dependent protein kinases (TgCDPKs), *C. parvum* and *C. hominus* calcium dependent protein kinases (CpCDPKs), or *P. falciparum* and *P. berghei* calcium dependent protein kinase 4 (PfCDPKs) using pyrazolopyrimidine inhibitors, or in another embodiment, imidazo[1,5-a]pyrazine inhibitors, both classes of compounds designed to be inactive against mammalian kinases.

In one aspect, the present disclosure provides compounds of the formula (I),

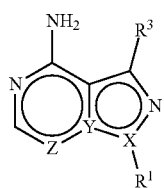

or a pharmaceutically acceptable salt thereof, wherein
X, Y, and Z are defined by either: (i) X is N, Y is C, and Z is N; or (ii) X is C, Y is N, and Z is C(H);
$R^1$ is $C_{2-6}$ alkyl, $C_{1-6}$ haloalkyl, —$C_{1-6}$ alkyl-$R^{12}$, $C_{3-8}$ cycloalkyl, heterocyclyl, heteroaryl, or aryl, wherein the alkyl, cycloalkyl, heterocyclyl, heteroaryl, and aryl groups are each optionally substituted with one or two $R^{11}$ groups;
each $R^{11}$ is independently halogen, cyano, nitro, $C_{1-6}$ alkyl, $C_{1-6}$ haloalkyl, —OR, —SR, —$NR_2$, —C(O)R, —C(O)OR, —C(O)$NR_2$, —S(O)$_2NR_2$, or —S(O)$_2$R; and
$R^{12}$ is —OR, —SR, —$NR_2$, —C(O)R, —C(O)OR, —C(O)$NR_2$, —S(O)$_2$R, —OC(O)R, —OC(O)OR, —OC(O)$NR_2$, —N(R)C(O)R, —N(R)C(O)OR, —N(R)C(O)$NR_2$, aryl, heteroaryl, $C_{3-8}$ cycloalkyl, or heterocyclyl, wherein $R^{12}$ is optionally substituted by one, two, or three groups that are each independently halogen, cyano, nitro, $C_{1-6}$ alkyl, $C_{1-6}$ haloalkyl, $C_{1-6}$ hydoxyalkyl, —OR, —SR, —$NR_2$, —C(O)R, —C(O)OR, —C(O)$NR_2$, —S(O)$_2$R, —OC(O)R, —OC(O)OR, —OC(O)$NR_2$, —N(R)C(O)R, —N(R)C(O)OR, or —N(R)C(O)$NR_2$;
$R^3$ is one of the formulas,

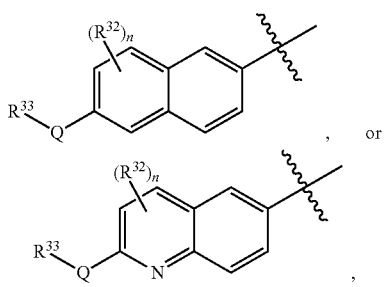

wherein
n is 0, 1, or 2;
Q is —O—, —S—, or —N($R^Q$)—, wherein $R^Q$ is hydrogen or $C_{1-6}$ alkyl; and
$R^{33}$ is $C_{1-6}$ alkyl, $C_{1-6}$ haloalkyl, $C_{3-8}$ cycloalkyl, ($C_{3-8}$ cycloalkyl)$C_{1-6}$ alkyl, or heterocyclyl, wherein the alkyl, cycloalkyl, and heterocyclyl are optionally substituted with one, two, three, or four groups that are each independently halogen, cyano, nitro, $C_{1-6}$ alkyl, $C_{1-6}$ haloalkyl, —$OR^{20}$, —$SR^{20}$, —$N(R^{20})_2$, —C(O)$R^{20}$, —C(O)$OR^{20}$, —C(O)N($R^{20})_2$, —S(O)$_2R^{20}$, —OC(O)$R^{20}$, —OC(O)$OR^{20}$, —OC(O)N($R^{20})_2$, —$N(R^{20})$C(O)$R^{20}$, —$N(R^{20})$C(O)$OR^{20}$, or —$N(R^{20})$C(O)N($R^{20})_2$, wherein each $R^{20}$ is independently hydrogen or $C_{1-6}$ alkyl, each $R^{32}$ is independently halogen, cyano, nitro, $C_{1-6}$ alkyl, $C_{1-6}$ haloalkyl, —$OR^{34}$, —$SR^{34}$, —$N(R^{34})_2$, —C(O)$R^{34}$, —C(O)$OR^{34}$, —C(O)N($R^{34})_2$, —S(O)$_2R^{34}$, —OC(O)$R^{34}$, —OC(O)$OR^{34}$, —OC(O)N($R^{34})_2$, —$N(R^{34})$C(O)$R^{34}$, —$N(R^{34})$C(O)$OR^{34}$, or —$N(R^{34})$C(O)N($R^{34})_2$, wherein each $R^{34}$ is independently hydrogen or $C_{1-6}$ alkyl;
and
each R is independently hydrogen, $C_{1-6}$ alkyl, $C_{2-6}$ alkenyl, $C_{1-6}$ haloalkyl, $C_{3-8}$ cycloalkyl, heterocyclyl, aryl, aryl$C_{1-6}$ alkyl, heteroaryl, or heteroaryl$C_{1-6}$ alkyl wherein the alkyl, aryl, arylalkyl, heteroaryl, and heteroarylalkyl are optionally substituted with one, two, three, or four groups that are each independently halogen, cyano, nitro, $C_{1-6}$ alkyl, $C_{1-6}$ haloalkyl, —$OR^0$, —$SR^0$, —$N(R^0)_2$, —C(O)$R^0$, —C(O)$OR^0$, —C(O)N($R^0)_2$, —S(O)$_2R^0$, —OC(O)$R^0$, —OC(O)$OR^0$, —OC(O)N($R^0)_2$, —N(R)C(O)$R^0$, —$N(R^0)$C(O)$OR^0$, or —$N(R^0)$C(O)N($R^0)_2$, wherein each $R^0$ is independently hydrogen or $C_{1-6}$ alkyl.

In certain embodiments, the compound of the formula (I) is not:
1-(6-ethoxynaphthalen-2-yl)-3-isopropylimidazo[1,5-a]pyrazin-8-amine;
3-(6-isopropoxynaphthalen-2-yl)-1-isopropyl-1H-pyrazolo[3,4-d]pyrimidin-4-amine;
1-isopropyl-3-(6-propoxynaphthalen-2-yl)-1H-pyrazolo[3,4-d]pyrimidin-4-amine;
1-isopropyl-3-(6-methoxynaphthalen-2-yl)-1H-pyrazolo[3,4-d]pyrimidin-4-amine;
3-(6-ethoxynaphthalen-2-yl)-1-isopropyl-1H-pyrazolo[3,4-d]pyrimidin-4-amine;
3-(6-methoxynaphthalen-2-yl)-1-(piperidin-4-ylmethyl)-1H-pyrazolo[3,4-d]pyrimidin-4-amine;
3-(6-ethoxynaphthalen-2-yl)-1-(piperidin-4-ylmethyl)-1H-pyrazolo[3,4-d]pyrimidin-4-amine;
3-(6-ethoxynaphthalen-2-yl)-1-((1-methylpiperidin-4-yl)methyl)-1H-pyrazolo[3,4-d]pyrimidin-4-amine;
3-(6-isopropoxynaphthalen-2-yl)-1-(piperidin-4-ylmethyl)-1H-pyrazolo[3,4-d]pyrimidin-4-amine;
1-(piperidin-4-ylmethyl)-3-(6-propoxynaphthalen-2-yl)-1H-pyrazolo[3,4-d]pyrimidin-4-amine;
3-(6-(benzyloxy)naphthalen-2-yl)-1-(piperidin-4-ylmethyl)-1H-pyrazolo[3,4-d]pyrimidin-4-amine;
3-(6-butoxynaphthalen-2-yl)-1-(piperidin-4-ylmethyl)-1H-pyrazolo[3,4-d]pyrimidin-4-amine;
3-(6-(allyloxy)naphthalen-2-yl)-1-(piperidin-4-ylmethyl)-1H-pyrazolo[3,4-d]pyrimidin-4-amine;
3-(6-(2-chlorobenzyloxy)naphthalen-2-yl)-1-(piperidin-4-ylmethyl)-1H-pyrazolo[3,4-d]pyrimidin-4-amine;
3-(6-(3-chlorobenzyloxy)naphthalen-2-yl)-1-(piperidin-4-ylmethyl)-1H-pyrazolo[3,4-d]pyrimidin-4-amine;
3-(6-(4-chlorobenzyloxy)naphthalen-2-yl)-1-(piperidin-4-ylmethyl)-1H-pyrazolo[3,4-d]pyrimidin-4-amine;
3-(6-(benzyloxy)naphthalen-2-yl)-1-isopropyl-1H-pyrazolo[3,4-d]pyrimidin-4-amine;
3-(6-(allyloxy)naphthalen-2-yl)-1-isopropyl-1H-pyrazolo[3,4-d]pyrimidin-4-amine;
3-(6-butoxynaphthalen-2-yl)-1-isopropyl-1H-pyrazolo[3,4-d]pyrimidin-4-amine;
3-(6-isobutoxynaphthalen-2-yl)-1-isopropyl-1H-pyrazolo[3,4-d]pyrimidin-4-amine;
3-(6-isobutoxynaphthalen-2-yl)-1-(piperidin-4-ylmethyl)-1H-pyrazolo[3,4-d]pyrimidin-4-amine;
3-(6-(2-chlorobenzyloxy)naphthalen-2-yl)-1-isopropyl-1H-pyrazolo[3,4-d]pyrimidin-4-amine;
3-(6-(3-chlorobenzyloxy)naphthalen-2-yl)-1-isopropyl-1H-pyrazolo[3,4-d]pyrimidin-4-amine;

3-(6-(2,5-dimethylbenzyloxy)naphthalen-2-yl)-1-isopropyl-1H-pyrazolo[3,4-d]pyrimidin-4-amine;

1-isopropyl-3-(6-(2-methylbenzyloxy)naphthalen-2-yl)-1H-pyrazolo[3,4-d]pyrimidin-4-amine;

1-isopropyl-3-(6-(2-methyl-5-(trifluoromethyl)benzyloxy) naphthalen-2-yl)-1H-pyrazolo[3,4-d]pyrimidin-4-amine;

3-(6-(3-chloro-4-(2,2,2-trifluoroethyl)benzyloxy)naphthalen-2-yl)-1-isopropyl-1H-pyrazolo[3,4-d]pyrimidin-4-amine;

3-(6-(3-chloro-5-fluorobenzyloxy)naphthalen-2-yl)-1-isopropyl-1H-pyrazolo[3,4-d]pyrimidin-4-amine;

1-isopropyl-3-(6-(1-phenylethoxy)naphthalen-2-yl)-1H-pyrazolo[3,4-d]pyrimidin-4-amine;

3-(6-(4-tert-butylbenzyloxy)naphthalen-2-yl)-1-isopropyl-1H-pyrazolo[3,4-d]pyrimidin-4-amine;

1-isopropyl-3-(6-(pyridin-4-ylmethoxy)naphthalen-2-yl)-1H-pyrazolo[3,4-d]pyrimidin-4-amine;

3-(6-(4-chlorobenzyloxy)naphthalen-2-yl)-1-isopropyl-1H-pyrazolo[3,4-d]pyrimidin-4-amine;

6-(4-amino-1-(piperidin-4-ylmethyl)-1H-pyrazolo[3,4-d] pyrimidin-3-yl)-N,N-dimethylquinolin-2-amine;

3-tert-butyl-1-(6-ethoxynaphthalen-2-yl)imidazo[1,5-a] pyrazin-8-amine;

3-tert-butyl-1-(6-methoxynaphthalen-2-yl)imidazo[1,5-a] pyrazin-8-amine;

3-(6-ethoxynaphthalen-2-yl)-1-(1-ethylpiperidin-4-yl)-1H-pyrazolo[3,4-d]pyrimidin-4-amine;

3-(6-ethoxynaphthalen-2-yl)-1-(piperidin-4-yl)-1H-pyrazolo[3,4-d]pyrimidin-4-amine; or 3-(6-ethoxynaphthalen-2-yl)-1-(1-methylpiperidin-4-yl)-1H-pyrazolo[3,4-d]pyrimidin-4-amine.

In certain other embodiments, the compound of the formula (I) is not any one of compounds disclosed in International Patent Publication WO 2011/0094628 and/or the U.S. Patent Publication 2013/0018040, both incorporated herein by reference in their entirety.

In another aspect, the present disclosure provides methods for treating an apicomplexan protozoan related disease comprising providing to a patient in need of such treatment a therapeutically effective amount of either (i) a compound of the disclosure or (ii) a pharmaceutical composition comprising a compound of the disclosure and a pharmaceutically acceptable excipient, carrier, or diluent.

In another aspect, the present disclosure provides methods for treating toxoplasmosis, cryptosporidiosis, coccidiosis, and malaria comprising providing to a patient in need of such treatment a therapeutically effective amount of either (i) a compound of the disclosure or (ii) a pharmaceutical composition comprising a compound of the disclosure and a pharmaceutically acceptable excipient, carrier, or diluent.

In another aspect, the present disclosure provides methods for treating malaria comprising providing to a patient in need of such treatment a therapeutically effective amount of either (i) a compound of the disclosure or (ii) a pharmaceutical composition comprising a compound of the disclosure and a pharmaceutically acceptable excipient, carrier, or diluent.

In one aspect, the present disclosure provides methods for treating neosporosis, caused by the eukaryotic parasite *Neospora caninum*, sarcocystosis, caused by the eukaryotic parasite *Sarcocystis neuronae* and other species, besnoitiosis, caused by *Besnoitia besnoiti*, coccidiosis, caused by *Hammondia hammondi* and other *Hammondia* spp., cystoisoporosis, caused by the eukaryotic parasitic species *Cystoisoporosis suis* and other species, babesiosis, caused by the eukaryotic parasites *Babesia microtii* and other species, and theileriosis, caused by the eukaryotic parasites *Theileria equi* and other species comprising providing to a patient in need of such treatment a therapeutically effective amount of either (i) a compound of the disclosure or (ii) a pharmaceutical composition comprising a compound of the disclosure and a pharmaceutically acceptable excipient, carrier, or diluent. In some embodiments of this aspect, the compound is 3-(6-ethoxynaphthalen-2-yl)-1-((1-methylpiperidin-4-yl) methyl)-1H-pyrazolo[3,4-d]pyrimidin-4-amine or 1-(4-Amino-3-(6-cyclopropoxynaphthalen-2-yl)-1H-pyrazolo[3, 4-d]pyrimidin-1-yl)-2-methylpropan-2-ol.

DETAILED DESCRIPTION OF THE INVENTION

Figure 1:
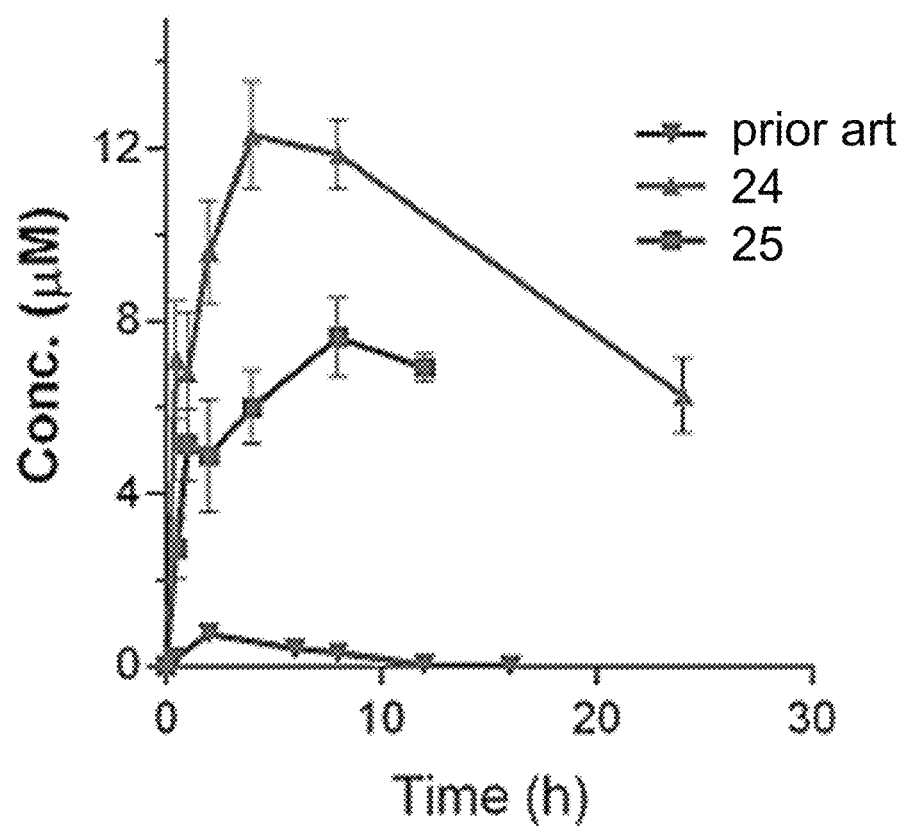
FIG. 1 shows comparison of oral PK for compounds of Example 24 and 25 in mice. Both compounds were dosed at 10 mg/kg, PO.

Before the disclosed methods are described, it is to be understood that the aspects described herein are not limited to specific embodiments, or compositions, and as such can, of course, vary. It is also to be understood that the terminology used herein is for the purpose of describing particular aspects only and, unless specifically defined herein, is not intended to be limiting.

Throughout this specification, unless the context requires otherwise, the word "comprise" and "include" and variations (e.g., "comprises," "comprising," "includes," "including") will be understood to imply the inclusion of a stated component, feature, element, or step or group of components, features, elements or steps but not the exclusion of any other integer or step or group of integers or steps.

As used in the specification and the appended claims, the singular forms "a," "an" and "the" include plural referents unless the context clearly dictates otherwise.

The term "pharmaceutical composition" is used in its widest sense, encompassing all pharmaceutically applicable compositions containing at least one active substance, and optional carriers, adjuvants, constituents etc. The term "pharmaceutical composition" also encompasses a composition comprising the active substance in the form of derivative or pro-drug, such as pharmaceutically acceptable salts and esters. The manufacture of pharmaceutical compositions for different routes of administration falls within the capabilities of a person skilled in medicinal chemistry.

In view of the present disclosure, the methods described herein can be configured by the person of ordinary skill in the art to meet the desired need. In general, the disclosed methods provide improved compounds useful in the treatment of apicomplexan-related diseases.

In one aspect, the present disclosure provides compounds of the formula (I),

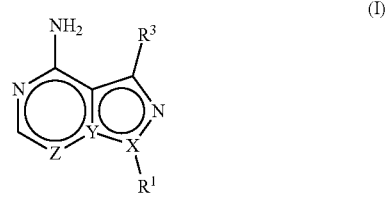

(I)

or a pharmaceutically acceptable salt thereof, wherein
X, Y, and Z are defined by either: (i) X is N, Y is C, and Z is N; or (ii) X is C, Y is N, and Z is C(H);

$R^1$ is $C_{2-6}$ alkyl, $C_{1-6}$ haloalkyl, —$C_{1-6}$ alkyl-$R^{12}$, $C_{3-8}$ cycloalkyl, heterocyclyl, heteroaryl, or aryl, wherein
  the alkyl, cycloalkyl, heterocyclyl, heteroaryl, and aryl groups are each optionally substituted with one or two $R^{11}$ groups;
  each $R^{11}$ is independently halogen, cyano, nitro, $C_{1-6}$ alkyl, $C_{1-6}$ haloalkyl, —OR, —SR, —$NR_2$, —C(O)R, —C(O)OR, —C(O)$NR_2$, —S(O)$_2NR_2$, or S(O)$_2$R;
  and
  $R^{12}$ is —OR, —SR, —$NR_2$, —C(O)R, —C(O)OR, —C(O)$NR_2$, —S(O)$_2$R, —OC(O)R, —OC(O)OR, —OC(O)$NR_2$, —N(R)C(O)R, —N(R)C(O)OR, —N(R)C(O)$NR_2$, aryl, heteroaryl, $C_{3-8}$ cycloalkyl, or heterocyclyl, wherein $R^{12}$ is optionally substituted by one, two, or three groups that are each independently halogen, cyano, nitro, $C_{1-6}$ alkyl, $C_{1-6}$ haloalkyl, $C_{1-6}$ hydoxyalkyl, —OR, —SR, —$NR_2$, —C(O)R, —C(O)OR, —C(O)$NR_2$, —S(O)$_2$R, —OC(O)R, —OC(O)OR, —OC(O)$NR_2$, —N(R)C(O)R, —N(R)C(O)OR, or —N(R)C(O)$NR_2$;

$R^3$ is one of the formulas,

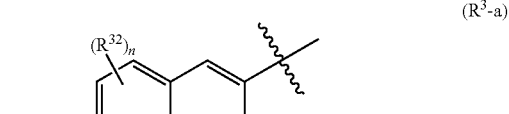

($R^3$-a)

, or

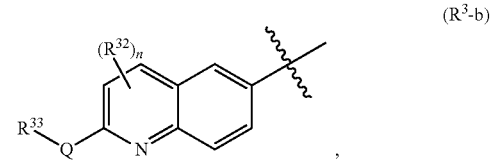

($R^3$-b)

, wherein
  n is 0, 1, or 2;
  Q is —O—, —S—, or —N($R^Q$)—, wherein $R^Q$ is hydrogen or $C_{1-6}$ alkyl; and
  $R^{33}$ is $C_{1-6}$ alkyl, $C_{1-6}$ haloalkyl, $C_{3-8}$ cycloalkyl, ($C_{3-8}$ cycloalkyl)$C_{1-6}$ alkyl, or heterocyclyl, wherein the alkyl, cycloalkyl, and heterocyclyl are optionally substituted with one, two, three, or four groups that are each independently halogen, cyano, nitro, $C_{1-6}$ alkyl, $C_{1-6}$ haloalkyl, —OR$^{20}$, —SR$^{20}$, —N(R$^{20}$)$_2$, —C(O)R$^{20}$, —C(O)OR$^{20}$, —C(O)N(R$^{20}$)$_2$, —S(O)$_2$R$^{20}$, —OC(O)R$^{20}$, —OC(O)OR$^{20}$, —OC(O)N(R$^{20}$)$_2$, —N(R$^{20}$)C(O)R$^{20}$, —N(R$^{20}$)C(O)OR$^{20}$, or or —N(R$^{20}$)C(O)N(R$^{20}$)$_2$, wherein each $R^{20}$ is independently hydrogen or $C_{1-6}$ alkyl,
  each $R^{32}$ is independently halogen, cyano, nitro, $C_{1-6}$ alkyl, $C_{1-6}$ haloalkyl, —OR$^{34}$, —SR$^{34}$, —N(R$^{34}$)$_2$, —C(O)R$^{34}$, —C(O)OR$^{34}$, —C(O)N(R$^{34}$)$_2$, —S(O)$_2$R$^{34}$, —OC(O)R$^{34}$, —OC(O)OR$^{34}$, —OC(O)N(R$^{34}$)$_2$, —N(R$^{34}$)C(O)R$^{34}$, —N(R$^{34}$)C(O)OR$^{34}$, or —N(R$^{34}$)C(O)N(R$^{34}$)$_2$, wherein each $R^{34}$ is independently hydrogen or $C_{1-6}$ alkyl;
and
each R is independently hydrogen, $C_{1-6}$ alkyl, $C_{2-6}$ alkenyl, $C_{1-6}$ haloalkyl, $C_{3-8}$ cycloalkyl, heterocyclyl, aryl, aryl$C_{1-6}$ alkyl, heteroaryl, or heteroaryl$C_{1-6}$ alkyl wherein the alkyl, aryl, arylalkyl, heteroaryl, and heteroarylalkyl are optionally substituted with one, two, three, or four groups that are each independently halogen, cyano, nitro, $C_{1-6}$ alkyl, $C_{1-6}$ haloalkyl, —OR$^0$, —SR$^0$, —N(R$^0$)$_2$, —C(O)R$^0$, —C(O)OR$^0$, —C(O)N(R$^0$)$_2$, —S(O)$_2$R$^0$, —OC(O)R$^0$, —OC(O)OR$^0$, —OC(O)N(R$^0$)$_2$, —N(R$^0$)C(O)R$^0$, —N(R$^0$)C(O)OR$^0$, or —N(R$^0$)C(O)N(R$^0$)$_2$, wherein each $R^0$ is independently hydrogen or $C_{1-6}$ alkyl.

The disclosure further comprises subgenera of formula (I) in which the substituents are selected as any and all combinations of one or more of structural formula (I), n, Q, $R^1$, $R^3$, $R^{32}$, and $R^{33}$ as defined herein, including without limitation, the following:

Structural Formula I is one of formulae (Ia)-(Ib):

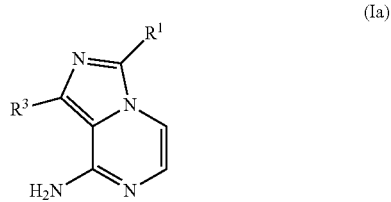

(Ia)

-continued

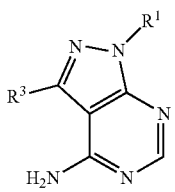
(Ib)

R¹ is selected from one of the following groups (1a)-(1ii):
(1a) R¹ is $C_{2-4}$ alkyl, —$C_{1-6}$ alkyl-$R^{12}$, $C_{3-8}$ cycloalkyl, heterocyclyl, heteroaryl, or aryl, wherein the cycloalkyl, heterocyclyl, heteroaryl, and aryl groups are each optionally substituted with one or two $R^{11}$ groups.
(1b) R¹ is $C_{3-8}$ cycloalkyl, heterocyclyl, heteroaryl, or aryl, wherein the cycloalkyl, heterocyclyl, heteroaryl, and aryl groups are each optionally substituted with one or two $R^{11}$ groups.
(1c) R¹ is $C_{3-8}$ cycloalkyl or a monocyclic heterocyclyl optionally substituted with one $R^{11}$ group.
(1d) R¹ is $C_{3-8}$ cycloalkyl.
(1e) R¹ is monocyclic heterocyclyl optionally substituted with one $R^{11}$ group.
(1f) R¹ is piperidinyl or tetrahydropyranyl, each optionally substituted with one $R^{11}$ group.
(1g) R¹ is phenyl optionally substituted with one or two $R^{11}$ groups.
(1h) R¹ is $C_{2-6}$ alkyl optionally substituted with one or two $R^{11}$ groups.
(1i) R¹ is $C_{2-4}$ alkyl optionally substituted with one or two $R^{11}$ groups.
(1j) R¹ is isopropyl or t-butyl.
(1k) R¹ is t-butyl.
(1l) R¹ is isopropyl.
(1m) R¹ is $C_{2-6}$ alkyl or —$C_{1-6}$ alkyl-$R^{12}$.
(1n) R¹ is —$C_{1-6}$ alkyl-$R^{12}$.
(1o) R¹ is —$C_{1-4}$ alkyl-$R^{12}$.
(1p) R¹ is $CH_2$—$R^{12}$.
(1q) Any one of groups (1m)-(1p), wherein $R^{12}$ is —OR, —C(O)OR, —C(O)$NR_2$, phenyl, monocyclic heteroaryl, $C_{3-8}$ cycloalkyl, or monocyclic heterocyclyl, wherein the phenyl, heteroaryl, $C_{3-8}$ cycloalkyl, and heterocyclyl groups are each optionally substituted by one, two, or three groups that are each independently halogen, cyano, nitro, $C_{1-6}$ alkyl, $C_{1-6}$ haloalkyl, —OR, —SR, —$NR_2$, —C(O)R, —C(O)OR, —C(O)$NR_2$, —S(O)$_2$R, —OC(O)R, —OC(O)OR, —OC(O)$NR_2$, —N(R)C(O)R, —N(R)C(O)OR, or —N(R)C(O)$NR_2$.
(1r) Any one of groups (1m)-(1p), $R^{12}$ is —OR.
(1s) Any one of groups (1m)-(1p), $R^{12}$ is —OH.
(1t) Any one of groups (1m)-(1p), wherein $R^{12}$ is phenyl, monocyclic heteroaryl, $C_{3-8}$ cycloalkyl, or monocyclic heterocyclyl, wherein the phenyl, heteroaryl, $C_{3-8}$ cycloalkyl, and heterocyclyl groups are each optionally substituted by one or two groups that are each independently halogen, $C_{1-6}$ alkyl, —C(O)R, —C(O)OR, —C(O)$NR_2$, —S(O)$_2$R, —OC(O)R, —OC(O)OR, —OC(O)$NR_2$, —N(R)C(O)R, —N(R)C(O)OR, or —N(R)C(O)$NR_2$.
(1u) Any one of groups (1m)-(1p), $R^{12}$ is phenyl or monocyclic heterocyclyl, each optionally substituted by one, two, or three groups that are each independently halogen, cyano, nitro, $C_{1-6}$ alkyl, $C_{1-6}$ haloalkyl, —OR, —SR, —$NR_2$, —C(O)R, —C(O)OR, —C(O)$NR_2$, —S(O)$_2$R, —OC(O)R, —OC(O)OR, —OC(O)$NR_2$, —N(R)C(O)R, —N(R)C(O)OR, or —N(R)C(O)$NR_2$.
(1v) Any one of groups (1m)-(1p), $R^{12}$ is monocyclic heterocyclyl optionally substituted by one, two, or three groups that are each independently halogen, cyano, nitro, $C_{1-6}$ alkyl, $C_{1-6}$ haloalkyl, —OR, —SR, —$NR_2$, —C(O)R, —C(O)OR, —C(O)$NR_2$, —S(O)$_2$R, —OC(O)R, —OC(O)OR, —OC(O)$NR_2$, —N(R)C(O)R, —N(R)C(O)OR, or —N(R)C(O)$NR_2$.
(1w) Any one of groups (1m)-(1p), wherein $R^{12}$ is monocyclic heterocyclyl optionally substituted by one or two groups that are each independently halogen, $C_{1-6}$ alkyl, —C(O)R, —C(O)OR, —C(O)$NR_2$, —S(O)$_2$R, —OC(O)R, —OC(O)OR, —OC(O)$NR_2$, —N(R)C(O)R, —N(R)C(O)OR, or —N(R)C(O)$NR_2$.
(1x) Any one of groups (1m)-(1p), $R^{12}$ is piperidinyl or tetrahydropyranyl, each optionally substituted by one or two groups that are each independently halogen, cyano, nitro, $C_{1-6}$ alkyl, $C_{1-6}$ haloalkyl, —OR, —SR, —$NR_2$, —C(O)R, —C(O)OR, —C(O)$NR_2$, —S(O)$_2$R, —OC(O)R, —OC(O)OR, —OC(O)$NR_2$, —N(R)C(O)R, —N(R)C(O)OR, or —N(R)C(O)$NR_2$.
(1y) Any one of groups (1m)-(1p), wherein $R^{12}$ is piperidinyl optionally substituted by one or two groups that are each independently halogen, cyano, nitro, $C_{1-6}$ alkyl, $C_{1-6}$ haloalkyl, —OR, —SR, —$NR_2$, —C(O)R, —C(O)OR, —C(O)$NR_2$, —S(O)$_2$R, —OC(O)R, —OC(O)OR, —OC(O)$NR_2$, —N(R)C(O)R, —N(R)C(O)OR, or —N(R)C(O)$NR_2$.
(1z) Any one of groups (1m)-(1p), wherein $R^{12}$ is piperidinyl optionally substituted by one or two groups that are each independently $C_{1-6}$ alkyl, —C(O)$R^4$, —C(O)O$R^4$, —C(O)N($R^4$)$_2$, —S(O)$_2R^4$, —OC(O)$R^4$, —OC(O)O$R^4$, —OC(O)N($R^4$)$_2$, —N($R^4$)C(O)$R^4$, —N($R^4$)C(O)O$R^4$, or —N($R^4$)C(O)N($R^4$)$_2$, wherein each $R^4$ is independently hydrogen, $C_{1-6}$ alkyl, $C_{2-6}$ alkenyl, $C_{1-6}$ haloalkyl, $C_{3-8}$ cycloalkyl, heterocyclyl, aryl, aryl$C_{1-6}$ alkyl, heteroaryl, or heteroaryl$C_{1-6}$ alkyl.
(1aa) Any one of groups (1m)-(1p), wherein $R^{12}$ is piperidinyl optionally substituted by one or two groups that are each independently $C_{1-6}$ alkyl, —C(O)R, —C(O)OR, —C(O)$NR_2$, —S(O)$_2$R, —OC(O)R, —OC(O)OR, —OC(O)$NR_2$, —N(R)C(O)R, —N(R)C(O)OR, or —N(R)C(O)$NR_2$.
(1bb) Any one of groups (1m)-(1p), wherein $R^{12}$ is piperidinyl optionally substituted by one or two groups that are each independently $C_{1-6}$ alkyl, —C(O)$R^4$, —C(O)O$R^4$, —C(O)N($R^4$)$_2$, —S(O)$_2R^4$, —OC(O)$R^4$, —OC(O)O$R^4$, —OC(O)N($R^4$)$_2$, —N($R^4$)C(O)$R^4$, —N($R^4$)C(O)O$R^4$, or —N($R^4$)C(O)N($R^4$)$_2$, wherein each $R^4$ is independently hydrogen or $C_{1-6}$ alkyl.
(1cc) Any one of groups (1m)-(1p), wherein $R^{12}$ is piperidinyl optionally substituted by one or two groups that are each independently $C_{1-6}$ alkyl, —C(O)R, —C(O)OR, —C(O)$NR_2$, or —S(O)$_2$R.
(1dd) Any one of groups (1m)-(1p), wherein $R^{12}$ is piperidinyl optionally substituted by one or two groups that are each independently $C_{1-6}$ alkyl, —C(O)$R^4$, or —S(O)$_2R^4$, wherein each $R^4$ is independently hydrogen or $C_{1-6}$ alkyl.
(1ee) Any one of groups (1m)-(1p), wherein $R^{12}$ is

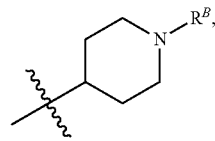

wherein $R^B$ is hydrogen, $C_{1-6}$ alkyl, —C(O)R, —C(O)OR, —C(O)NR$_2$, —S(O)$_2$R, —OC(O)R, —OC(O)OR, —OC(O)NR$_2$, —N(R)C(O)R, —N(R)C(O)OR, or —N(R)C(O)NR$_2$.

(1ff) Any one of groups (1m)-(1p), wherein $R^{12}$ is

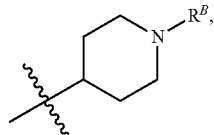

wherein $R^B$ is hydrogen, $C_{1-6}$ alkyl, —C(O)R$^A$, —C(O)OR$^A$, —C(O)N(R$^A$)$_2$, —S(O)$_2$R$^A$, —OC(O)R$^A$, —OC(O)OR$^A$, —OC(O)N(R$^A$)$_2$, —N(R$^A$)C(O)R$^A$, —N(R$^A$)C(O)OR$^A$, or —N(R$^A$)C(O)N(R$^A$)$_2$, wherein each $R^A$ is independently hydrogen, $C_{1-6}$ alkyl, $C_{2-6}$ alkenyl, $C_{1-6}$ haloalkyl, $C_{3-8}$ cycloalkyl, heterocyclyl, aryl, aryl$C_{1-6}$ alkyl, heteroaryl, or heteroaryl$C_{1-6}$ alkyl.

(1gg) Any one of groups (1m)-(1p), wherein $R^{12}$ is

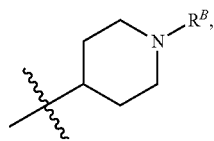

wherein $R^B$ is hydrogen, $C_{1-6}$ alkyl, —C(O)R$^A$, —C(O)OR$^A$, —C(O)N(R$^A$)$_2$, —S(O)$_2$R$^A$, —OC(O)R$^A$, —OC(O)OR$^A$, —OC(O)N(R$^A$)$_2$, —N(R$^A$)C(O)R$^A$, —N(R$^A$)C(O)OR$^A$, or —N(R$^A$)C(O)N(R$^A$)$_2$, wherein each $R^A$ is independently hydrogen or $C_{1-6}$ alkyl.

(1hh) Any one of groups (1m)-(1p), wherein $R^{12}$ is

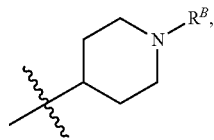

wherein $R^B$ is hydrogen, $C_{1-6}$ alkyl, —C(O)R, —C(O)OR, —C(O)NR$_2$, or —S(O)$_2$R.

(1ii) Any one of groups (1m)-(1p), wherein $R^{12}$ is

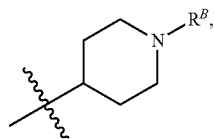

wherein $R^B$ is hydrogen, $C_{1-6}$ alkyl, —C(O)R$^A$, or —S(O)$_2$R$^A$, wherein each $R^A$ is independently hydrogen or $C_{1-6}$ alkyl.

$R^3$ is selected from one of the following groups (2a)-(2b):
(2a) $R^3$ is group ($R^3$-a).
(2b) $R^3$ is group ($R^3$-b).

Q is selected from one of the following groups (3a)-(3e):
(3a) Q is —O— or —(R$^Q$)—.
(3b) Q is —O— or —N(H)—.
(3c) Q is —O—.
(3d) Q is —N(R$^Q$)—.
(3e) Q is —N(H)—.

n and $R^{32}$ are selected from one of the following groups (4a)-(4x):
(4a) n is 0.
(4b) n is 0 or 1 and $R^{32}$ is as defined for formula (I).
(4c) n is 0 or 1 and $R^{32}$ is halogen, cyano, nitro, $C_{1-6}$ alkyl, or $C_{1-6}$ haloalkyl.
(4d) n is 0 or 1 and $R^{32}$ is halogen, $C_{1-6}$ alkyl, or $C_{1-6}$ haloalkyl.
(4e) n is 0 or 1 and each $R^{32}$ is —OR$^{34}$, —SR$^{34}$, —N(R$^{34}$)$_2$, —C(O)R$^{34}$, —C(O)OR$^{34}$, —C(O)N(R$^{34}$)$_2$, —S(O)$_2$R$^{34}$, —OC(O)R$^{34}$, —OC(O)OR$^{34}$, —OC(O)N(R$^{34}$)$_2$, —N(R$^{34}$)C(O)R$^{34}$, —N(R$^{34}$)C(O)OR$^{34}$, or —N(R$^{34}$)C(O)N(R$^{34}$)$_2$, wherein each $R^{34}$ is independently hydrogen or $C_{1-6}$ alkyl.
(4f) n is 0 or 1 and $R^{32}$ is OR$^{34}$, —SR$^{34}$, —N(R$^{34}$)$_2$, wherein each $R^{34}$ is independently hydrogen or $C_{1-6}$ alkyl.
(4g) n is 0 or 1 and $R^{32}$ is —C(O)R$^{34}$, —C(O)OR$^{34}$, —C(O)N(R$^{34}$)$_2$, or S(O)$_2$R$^{34}$, wherein each $R^{34}$ is independently hydrogen or $C_{1-6}$ alkyl.
(4h) n is as defined for formula (I) and each $R^{32}$ is independently halogen, cyano, nitro, $C_{1-6}$ alkyl, or $C_{1-6}$ haloalkyl.
(4i) n is as defined for formula (I) and each $R^{32}$ is independently halogen, $C_{1-6}$ alkyl, or $C_{1-6}$ haloalkyl.
(4j) n is as defined for formula (I) and each $R^{32}$ is independently —OR$^{34}$, —SR$^{34}$, —N(R$^{34}$)$_2$, —C(O)R$^{34}$, —C(O)OR$^{34}$, —C(O)N(R$^{34}$)$_2$, —S(O)$_2$R$^{34}$, —OC(O)R$^{34}$, —OC(O)OR$^{34}$, —OC(O)N(R$^{34}$)$_2$, —N(R$^{34}$)C(O)R$^{34}$, —N(R$^{34}$)C(O)OR$^{34}$, or —N(R$^{34}$)C(O)N(R$^{34}$)$_2$, wherein each $R^{34}$ is independently hydrogen or $C_{1-6}$ alkyl.
(4k) n is as defined for formula (I) and each $R^{32}$ is independently —OR$^{34}$, —SR$^{34}$, —N(R$^{34}$)$_2$, wherein each $R^{34}$ is independently hydrogen or $C_{1-6}$ alkyl.
(4l) n is as defined for formula (I) and each $R^{32}$ is independently —C(O)R$^{34}$, —C(O)OR$^{34}$, —C(O)N(R$^{34}$)$_2$, or —S(O)$_2$R$^{34}$, wherein each $R^{34}$ is independently hydrogen or $C_{1-6}$ alkyl.
(4m) n is 1 or 2 and each $R^{32}$ is as defined for formula (I).
(4n) n is 1 or 2 and each $R^{32}$ is independently halogen, cyano, nitro, $C_{1-6}$ alkyl, or $C_{1-6}$ haloalkyl.
(4o) n is 1 or 2 and each $R^{32}$ is independently halogen, $C_{1-6}$ alkyl, or $C_{1-6}$ haloalkyl.
(4p) n is 1 or 2 and each $R^{32}$ is independently —OR$^{34}$, —SR$^{34}$, —N(R$^{34}$)$_2$, —C(O)R$^{34}$, —C(O)OR$^{34}$, —C(O)N(R$^{34}$)$_2$, —S(O)$_2$R$^{34}$, —OC(O)R$^{34}$, —OC(O)OR$^{34}$, —OC(O)N(R$^{34}$)$_2$, —N(R$^{34}$)C(O)R$^{34}$, —N(R$^{34}$)C(O)OR$^{34}$, or —N(R$^{34}$)C(O)N(R$^{34}$)$_2$ wherein each $R^{34}$ is independently hydrogen or $C_{1-6}$ alkyl.
(4q) n is 1 or 2 and each $R^{32}$ is independently —OR$^{34}$, —SR$^{34}$, —N(R$^{34}$)$_2$, wherein each $R^{34}$ is independently hydrogen or $C_{1-6}$ alkyl.
(4r) n is 1 or 2 and each $R^{32}$ is independently —C(O)R$^{34}$, —C(O)OR$^{34}$, —C(O)N(R$^{34}$)$_2$, or —S(O)$_2$R$^{34}$, wherein each $R^{34}$ is independently hydrogen or $C_{1-6}$ alkyl.
(4s) n is 1 and $R^{32}$ is as defined for formula (I).
(4t) n is 1 and $R^{32}$ is halogen, cyano, nitro, $C_{1-6}$ alkyl, or $C_{1-6}$ haloalkyl.
(4u) n is 1 and $R^{32}$ is halogen, $C_{1-6}$ alkyl, or $C_{1-6}$ haloalkyl.
(4v) n is 1 and $R^{32}$ is —OR$^{34}$, —SR$^{34}$, —N(R$^{34}$)$_2$, —C(O)R$^{34}$, —C(O)OR$^{34}$, —C(O)N(R$^{34}$)$_2$, —S(O)$_2$R$^{34}$, —OC(O)R$^{34}$, —OC(O)OR$^{34}$, —OC(O)N(R$^{34}$)$_2$, —N(R$^{34}$)C(O)R$^{34}$, —N(R$^{34}$)C(O)OR$^{34}$, or —N($R^{34}$)C(O)N($R^{34}$)$_2$, wherein each $R^{34}$ is independently hydrogen or $C_{1-6}$ alkyl.

(4w) n is 1 and $R^{32}$ is —O$R^{34}$, —S$R^{34}$, —N($R^{34}$)$_2$, wherein each $R^{34}$ is independently hydrogen or $C_{1-6}$ alkyl.

(4x) n is 1 and $R^{32}$ is —C(O)$R^{34}$, —C(O)O$R^{34}$, —C(O)N($R^{34}$)$_2$, or —S(O)$_2R^{34}$, wherein each $R^{34}$ is independently hydrogen or $C_{1-6}$ alkyl.

$R^{33}$ is selected from one of the following groups (5a)-(5t):

(5a) $R^{33}$ is $C_{1-6}$ alkyl, $C_{3-8}$ cycloalkyl, ($C_{3-8}$ cycloalkyl)$C_{1-6}$ alkyl, or heterocyclyl, wherein the alkyl, cycloalkyl, and heterocyclyl are optionally substituted with one, two, three, or four groups that are each independently halogen, cyano, nitro, $C_{1-6}$ alkyl, $C_{1-6}$ haloalkyl, —O$R^{20}$, —S$R^{20}$, —N($R^{20}$)$_2$, —C(O)$R^{20}$, —C(O)O$R^{20}$, —C(O)N($R^{20}$)$_2$, —S(O)$_2R^{20}$, —OC(O)$R^{20}$, —OC(O)O$R^{20}$, —OC(O)N($R^{20}$)$_2$, —N($R^{20}$)C(O)$R^{20}$, —N($R^{20}$)C(O)O$R^{20}$, or —N($R^{20}$)C(O)N($R^{20}$)$_2$, wherein each $R^{20}$ is independently hydrogen or $C_{1-6}$ alkyl.

(5b) $R^{33}$ is $C_{1-6}$ alkyl, $C_{3-8}$ cycloalkyl, ($C_{3-8}$ cycloalkyl)$C_{1-6}$ alkyl, or heterocyclyl, wherein the alkyl, cycloalkyl, and heterocyclyl are each substituted with one, two, three, or four groups that are each independently halogen, cyano, nitro, $C_{1-6}$ alkyl, $C_{1-6}$ haloalkyl, —O$R^{20}$, —S$R^{20}$, —N($R^{20}$)$_2$, —C(O)$R^{20}$, —C(O)O$R^{20}$, —C(O)N($R^{20}$)$_2$, —S(O)$_2R^{20}$, —OC(O)$R^{20}$, —OC(O)O$R^{20}$, —OC(O)N($R^{20}$)$_2$, —N($R^{20}$)C(O)$R^{20}$, —N($R^{20}$)C(O)O$R^{20}$, or —N($R^{20}$)C(O)N($R^{20}$)$_2$, wherein each $R^{20}$ is independently hydrogen or $C_{1-6}$ alkyl.

(5c) $R^{33}$ is $C_{1-6}$ alkyl, $C_{3-8}$ cycloalkyl, ($C_{3-8}$ cycloalkyl)$C_{1-6}$ alkyl, or heterocyclyl, wherein the alkyl, cycloalkyl, and heterocyclyl are optionally substituted with one or two groups that are each independently halogen, $C_{1-6}$ alkyl, or $C_{1-6}$ haloalkyl.

(5d) $R^{33}$ is $C_{1-6}$ alkyl, $C_{3-8}$ cycloalkyl, ($C_{3-8}$ cycloalkyl)$C_{1-6}$ alkyl, or heterocyclyl, wherein the alkyl, cycloalkyl, and heterocyclyl are each substituted with one or two groups that are each independently halogen, $C_{1-6}$ alkyl, or $C_{1-6}$ haloalkyl.

(5e) $R^{33}$ is $C_{3-8}$ cycloalkyl, ($C_{3-8}$ cycloalkyl)$C_{1-6}$ alkyl, or heterocyclyl, wherein the, cycloalkyl, and heterocyclyl are optionally substituted with one, two, three, or four groups that are each independently halogen, cyano, nitro, $C_{1-6}$ alkyl, $C_{1-6}$ haloalkyl, —O$R^{20}$, —S$R^{20}$, —N($R^{20}$)$_2$, —C(O)$R^{20}$, —C(O)O$R^{20}$, —C(O)N($R^{20}$)$_2$, —S(O)$_2R^{20}$, —OC(O)$R^{20}$, —OC(O)O$R^{20}$, —OC(O)N($R^{20}$)$_2$, —N($R^{20}$)C(O)$R^{20}$, —N($R^{20}$)C(O)O$R^{20}$, or —N($R^{20}$)C(O)N($R^{20}$)$_2$, wherein each $R^{20}$ is independently hydrogen or $C_{1-6}$ alkyl.

(5f) $R^{33}$ is $C_{3-8}$ cycloalkyl or ($C_{3-8}$ cycloalkyl)$C_{1-6}$ alkyl, wherein the cycloalkyl is optionally substituted with one, two, three, or four groups that are each independently halogen, cyano, nitro, $C_{1-6}$ alkyl, $C_{1-6}$ haloalkyl, —O$R^{20}$, —S$R^{20}$, —N($R^{20}$)$_2$, —C(O)$R^{20}$, —C(O)O$R^{20}$, —C(O)N($R^{20}$)$_2$, —S(O)$_2R^{20}$, —OC(O)$R^{20}$, —OC(O)O$R^{20}$, —OC(O)N($R^{20}$)$_2$, —N($R^{20}$)C(O)$R^{20}$, —N($R^{20}$)C(O)O$R^{20}$, or —N($R^{20}$)C(O)N($R^{20}$)$_2$, wherein each $R^{20}$ is independently hydrogen or $C_{1-6}$ alkyl.

(5g) $R^{33}$ is $C_{3-8}$ cycloalkyl, optionally substituted with one or two groups that are each independently halogen, $C_{1-6}$ alkyl, or $C_{1-6}$ haloalkyl.

(5h) $R^{33}$ is $C_{3-6}$ cycloalkyl, are each substituted with one or two groups that are each independently halogen, $C_{1-6}$ alkyl, or $C_{1-6}$ haloalkyl.

(5i) $R^{33}$ is $C_{3-8}$ cycloalkyl, optionally substituted with one, two, three, or four groups that are each independently halogen, cyano, nitro, $C_{1-6}$ alkyl, $C_{1-6}$ haloalkyl, —O$R^{20}$, —S$R^{20}$, —N($R^{20}$)$_2$, —C(O)$R^{20}$, —C(O)O$R^{20}$, —C(O)N($R^{20}$)$_2$, —S(O)$_2R^{20}$, —OC(O)$R^{20}$, —OC(O)O$R^{20}$, —OC(O)N($R^{20}$)$_2$, —N($R^{20}$)C(O)$R^{20}$, —N($R^{20}$)C(O)O$R^{20}$, or —N($R^{20}$)C(O)N($R^{20}$)$_2$, wherein each $R^{20}$ is independently hydrogen or $C_{1-6}$ alkyl.

(5j) $R^{33}$ is $C_{1-6}$ alkyl or $C_{3-8}$ cycloalkyl, wherein the alkyl and cycloalkyl are optionally substituted with one, two, three, or four groups that are each independently halogen, cyano, nitro, $C_{1-6}$ alkyl, $C_{1-6}$ haloalkyl, —O$R^{20}$, —S$R^{20}$, —N($R^{20}$)$_2$, —C(O)$R^{20}$, —C(O)O$R^{20}$, —C(O)N($R^{20}$)$_2$, —S(O)$_2R^{20}$, —OC(O)$R^{20}$, —OC(O)O$R^{20}$, —OC(O)N($R^{20}$)$_2$, —N($R^{20}$)C(O)$R^{20}$, —N($R^{20}$)C(O)O$R^{20}$, or —N($R^{20}$)C(O)N($R^{20}$)$_2$, wherein each $R^{20}$ is independently hydrogen or $C_{1-6}$ alkyl.

(5k) $R^{33}$ is $C_{1-6}$ alkyl or $C_{3-8}$ cycloalkyl, wherein the alkyl and cycloalkyl are optionally substituted with one or two groups that are each independently halogen, cyano, nitro, $C_{1-6}$ alkyl, $C_{1-6}$ haloalkyl, —O$R^{20}$, —S$R^{20}$, —N($R^{20}$)$_2$, —C(O)$R^{20}$, —C(O)O$R^{20}$, —C(O)N($R^{20}$)$_2$, —S(O)$_2R^{20}$, —OC(O)$R^{20}$, —OC(O)O$R^{20}$, —OC(O)N($R^{20}$)$_2$, —N($R^{20}$)C(O)$R^{20}$, —N($R^{20}$)C(O)O$R^{20}$, or —N($R^{20}$)C(O)N($R^{20}$)$_2$, wherein each $R^{20}$ is independently hydrogen or $C_{1-6}$ alkyl.

(5l) $R^{33}$ is $C_{1-6}$ alkyl or $C_{3-8}$ cycloalkyl, wherein the alkyl and cycloalkyl are optionally substituted with one or two groups that are each independently halogen, cyano, nitro, $C_{1-6}$ alkyl, $C_{1-6}$ haloalkyl, —O$R^{20}$, —S$R^{20}$, —N($R^{20}$)$_2$, —C(O)$R^{20}$, —C(O)O$R^{20}$, or —C(O)N($R^{20}$)$_2$, wherein each $R^{20}$ is independently hydrogen or $C_{1-6}$ alkyl.

(5m) $R^{33}$ is $C_{1-6}$ alkyl or $C_{3-8}$ cycloalkyl, wherein the alkyl and cycloalkyl are optionally substituted with one or two groups that are each independently halogen, cyano, nitro, $C_{1-6}$ alkyl, $C_{1-6}$ haloalkyl, —O$R^{20}$, —N($R^{20}$)$_2$, —C(O)$R^{20}$, —C(O)O$R^{20}$, or —C(O)N($R^{20}$)$_2$, wherein each $R^{20}$ is independently hydrogen or $C_{1-6}$ alkyl.

(5n) $R^{33}$ is $C_{1-6}$ alkyl or $C_{3-8}$ cycloalkyl.

(5o) $R^{33}$ is $C_{1-4}$ alkyl or $C_{3-6}$ cycloalkyl.

(5p) $R^{33}$ is $C_{1-4}$ alkyl, cyclopropyl, or cyclobutyl.

(5q) $R^{33}$ is methyl, ethyl, propyl, isopropyl, butyl, isobutyl, tert-butyl, cyclopropyl, or cyclobutyl.

Particular embodiments of this aspect of the invention include compounds of any one of the formulae (I), (Ia), and (Ib), each as defined in each of the following rows, wherein each entry is a group number as defined above (e.g., (3c) refers to Q is —O—), a dash "-" indicates that the variable is as defined for formula (I) or defined according to any one of the applicable variable definitions (1a)-(5q) [e.g., when $R^1$ is a dash, it can be either as defined for Formula (I) or any one of definitions (1a)-(1ii)]; and an "x" indicates that the variable is not applicable to the particular embodiment:

|  | $R^1$ | $R^3$ | $R^{33}$ | n & $R^{32}$ | Q |
|---|---|---|---|---|---|
| (1)-1 | 1h | 2b | 5a | 4c | 3a |
| (1)-2 | 1n | 2b | 5a | 4c | 3a |
| (1)-3 | 1p | 2b | 5a | 4c | 3a |
| (1)-4 | 1aa | 2b | 5a | 4c | 3a |
| (1)-5 | 1h | 2b | 5e | 4c | 3a |
| (1)-6 | 1n | 2b | 5e | 4c | 3a |
| (1)-7 | 1p | 2b | 5e | 4c | 3a |
| (1)-8 | 1aa | 2b | 5e | 4c | 3a |

| | R¹ | R³ | R³³ | n & R³² | Q |
|---|---|---|---|---|---|
| (1)-9 | 1h | 2b | 5i | 4c | 3a |
| (1)-10 | 1n | 2b | 5i | 4c | 3a |
| (1)-11 | 1p | 2b | 5i | 4c | 3a |
| (1)-12 | 1aa | 2b | 5i | 4c | 3a |
| (1)-13 | 1h | 2b | 5q | 4c | 3a |
| (1)-14 | 1n | 2b | 5q | 4c | 3a |
| (1)-15 | 1p | 2b | 5q | 4c | 3a |
| (1)-16 | 1aa | 2b | 5q | 4c | 3a |
| (1)-17 | 1h | 2a | 5a | 4c | 3a |
| (1)-18 | 1n | 2a | 5a | 4c | 3a |
| (1)-19 | 1p | 2a | 5a | 4c | 3a |
| (1)-20 | 1aa | 2a | 5a | 4c | 3a |
| (1)-21 | 1h | 2a | 5e | 4c | 3a |
| (1)-22 | 1n | 2a | 5e | 4c | 3a |
| (1)-23 | 1p | 2a | 5e | 4c | 3a |
| (1)-24 | 1aa | 2a | 5e | 4c | 3a |
| (1)-25 | 1h | 2a | 5i | 4c | 3a |
| (1)-26 | 1n | 2a | 5i | 4c | 3a |
| (1)-27 | 1p | 2a | 5i | 4c | 3a |
| (1)-28 | 1aa | 2a | 5i | 4c | 3a |
| (1)-29 | 1h | 2a | 5q | 4c | 3a |
| (1)-30 | 1n | 2a | 5q | 4c | 3a |
| (1)-31 | 1p | 2a | 5q | 4c | 3a |
| (1)-32 | 1aa | 2a | 5q | 4c | 3a |
| (1)-33 | 1h | 2b | 5a | 4n | 3a |
| (1)-34 | 1n | 2b | 5a | 4n | 3a |
| (1)-35 | 1p | 2b | 5a | 4n | 3a |
| (1)-36 | 1aa | 2b | 5a | 4n | 3a |
| (1)-37 | 1h | 2b | 5e | 4n | 3a |
| (1)-38 | 1n | 2b | 5e | 4n | 3a |
| (1)-39 | 1p | 2b | 5e | 4n | 3a |
| (1)-40 | 1aa | 2b | 5e | 4n | 3a |
| (1)-41 | 1h | 2b | 5i | 4n | 3a |
| (1)-42 | 1n | 2b | 5i | 4n | 3a |
| (1)-43 | 1p | 2b | 5i | 4n | 3a |
| (1)-44 | 1aa | 2b | 5i | 4n | 3a |
| (1)-45 | 1h | 2b | 5q | 4n | 3a |
| (1)-46 | 1n | 2b | 5q | 4n | 3a |
| (1)-47 | 1p | 2b | 5q | 4n | 3a |
| (1)-48 | 1aa | 2b | 5q | 4n | 3a |
| (1)-49 | 1h | 2a | 5a | 4n | 3a |
| (1)-50 | 1n | 2a | 5a | 4n | 3a |
| (1)-51 | 1p | 2a | 5a | 4n | 3a |
| (1)-52 | 1aa | 2a | 5a | 4n | 3a |
| (1)-53 | 1h | 2a | 5e | 4n | 3a |
| (1)-54 | 1n | 2a | 5e | 4n | 3a |
| (1)-55 | 1p | 2a | 5e | 4n | 3a |
| (1)-56 | 1aa | 2a | 5e | 4n | 3a |
| (1)-57 | 1h | 2a | 5i | 4n | 3a |
| (1)-58 | 1n | 2a | 5i | 4n | 3a |
| (1)-59 | 1p | 2a | 5i | 4n | 3a |
| (1)-60 | 1aa | 2a | 5i | 4n | 3a |
| (1)-61 | 1h | 2a | 5q | 4n | 3a |
| (1)-62 | 1n | 2a | 5q | 4n | 3a |
| (1)-63 | 1p | 2a | 5q | 4n | 3a |
| (1)-64 | 1aa | 2a | 5q | 4n | 3a |
| (1)-65 | 1h | 2b | 5a | 4c | 3c |
| (1)-66 | 1n | 2b | 5a | 4c | 3c |
| (1)-67 | 1p | 2b | 5a | 4c | 3c |
| (1)-68 | 1aa | 2b | 5a | 4c | 3c |
| (1)-69 | 1h | 2b | 5e | 4c | 3c |
| (1)-70 | 1n | 2b | 5e | 4c | 3c |
| (1)-71 | 1p | 2b | 5e | 4c | 3c |
| (1)-72 | 1aa | 2b | 5e | 4c | 3c |
| (1)-73 | 1h | 2b | 5i | 4c | 3c |
| (1)-74 | 1n | 2b | 5i | 4c | 3c |
| (1)-75 | 1p | 2b | 5i | 4c | 3c |
| (1)-76 | 1aa | 2b | 5i | 4c | 3c |
| (1)-77 | 1h | 2b | 5q | 4c | 3c |
| (1)-78 | 1n | 2b | 5q | 4c | 3c |
| (1)-79 | 1p | 2b | 5q | 4c | 3c |
| (1)-80 | 1aa | 2b | 5q | 4c | 3c |
| (1)-81 | 1h | 2a | 5a | 4c | 3c |
| (1)-82 | 1n | 2a | 5a | 4c | 3c |
| (1)-83 | 1p | 2a | 5a | 4c | 3c |
| (1)-84 | 1aa | 2a | 5a | 4c | 3c |
| (1)-85 | 1h | 2a | 5e | 4c | 3c |
| (1)-86 | 1n | 2a | 5e | 4c | 3c |
| (1)-87 | 1p | 2a | 5e | 4c | 3c |
| (1)-88 | 1aa | 2a | 5e | 4c | 3c |
| (1)-89 | 1h | 2a | 5i | 4c | 3c |
| (1)-90 | 1n | 2a | 5i | 4c | 3c |
| (1)-91 | 1p | 2a | 5i | 4c | 3c |
| (1)-92 | 1aa | 2a | 5i | 4c | 3c |
| (1)-93 | 1h | 2a | 5q | 4c | 3c |
| (1)-94 | 1n | 2a | 5q | 4c | 3c |
| (1)-95 | 1p | 2a | 5q | 4c | 3c |
| (1)-96 | 1aa | 2a | 5q | 4c | 3c |
| (1)-97 | 1h | 2b | 5a | 4n | 3c |
| (1)-98 | 1n | 2b | 5a | 4n | 3c |
| (1)-99 | 1p | 2b | 5a | 4n | 3c |
| (1)-100 | 1aa | 2b | 5a | 4n | 3c |
| (1)-101 | 1h | 2b | 5e | 4n | 3c |
| (1)-102 | 1n | 2b | 5e | 4n | 3c |
| (1)-103 | 1p | 2b | 5e | 4n | 3c |
| (1)-104 | 1aa | 2b | 5e | 4n | 3c |
| (1)-105 | 1h | 2b | 5i | 4n | 3c |
| (1)-106 | 1n | 2b | 5i | 4n | 3c |
| (1)-107 | 1p | 2b | 5i | 4n | 3c |
| (1)-108 | 1aa | 2b | 5i | 4n | 3c |
| (1)-109 | 1h | 2b | 5q | 4n | 3c |
| (1)-110 | 1n | 2b | 5q | 4n | 3c |
| (1)-111 | 1p | 2b | 5q | 4n | 3c |
| (1)-112 | 1aa | 2b | 5q | 4n | 3c |
| (1)-113 | 1h | 2a | 5a | 4n | 3c |
| (1)-114 | 1n | 2a | 5a | 4n | 3c |
| (1)-115 | 1p | 2a | 5a | 4n | 3c |
| (1)-116 | 1aa | 2a | 5a | 4n | 3c |
| (1)-117 | 1h | 2a | 5e | 4n | 3c |
| (1)-118 | 1n | 2a | 5e | 4n | 3c |
| (1)-119 | 1p | 2a | 5e | 4n | 3c |
| (1)-120 | 1aa | 2a | 5e | 4n | 3c |
| (1)-121 | 1h | 2a | 5i | 4n | 3c |
| (1)-122 | 1n | 2a | 5i | 4n | 3c |
| (1)-123 | 1p | 2a | 5i | 4n | 3c |
| (1)-124 | 1aa | 2a | 5i | 4n | 3c |
| (1)-125 | 1h | 2a | 5q | 4n | 3c |
| (1)-126 | 1n | 2a | 5q | 4n | 3c |
| (1)-127 | 1p | 2a | 5q | 4n | 3c |
| (1)-128 | 1aa | 2a | 5q | 4n | 3c |
| (1)-129 | 1h | 2b | — | — | — |
| (1)-130 | 1n | 2b | — | — | — |
| (1)-131 | 1p | 2b | — | — | — |
| (1)-132 | 1aa | 2b | — | — | — |
| (1)-133 | 1h | 2a | — | — | — |
| (1)-134 | 1n | 2a | — | — | — |
| (1)-135 | 1p | 2a | — | — | — |
| (1)-136 | 1aa | 2a | — | — | — |
| (1)-137 | 1h | 2b | — | — | 3c |
| (1)-138 | 1n | 2b | — | — | 3c |
| (1)-139 | 1p | 2b | — | — | 3c |
| (1)-140 | 1aa | 2b | — | — | 3c |
| (1)-141 | 1h | 2a | — | — | 3c |
| (1)-142 | 1n | 2a | — | — | 3c |
| (1)-143 | 1p | 2a | — | — | 3c |
| (1)-144 | 1aa | 2a | — | — | 3c |
| (1)-145 | 1h | 2b | — | — | 3a |
| (1)-146 | 1n | 2b | — | — | 3a |
| (1)-147 | 1p | 2b | — | — | 3a |
| (1)-148 | 1aa | 2b | — | — | 3a |
| (1)-149 | 1h | 2a | — | — | 3a |
| (1)-150 | 1n | 2a | — | — | 3a |
| (1)-151 | 1p | 2a | — | — | 3a |
| (1)-152 | 1aa | 2a | — | — | 3a |
| (1)-153 | — | — | 5a | — | 3a |
| (1)-154 | — | — | 5e | — | 3a |
| (1)-155 | — | — | 5i | — | 3a |
| (1)-156 | — | — | 5q | — | 3a |
| (1)-157 | — | — | 5a | — | 3c |
| (1)-158 | — | — | 5e | — | 3c |
| (1)-159 | — | — | 5i | — | 3c |
| (1)-160 | — | — | 5q | — | 3a |
| (1)-161 | — | 2b | 5a | — | 3a |
| (1)-162 | — | 2b | 5e | — | 3a |

-continued

| | R¹ | R³ | R³³ | n & R³² | Q |
|---|---|---|---|---|---|
| (1)-163 | — | 2b | 5i | — | 3a |
| (1)-164 | — | 2b | 5q | — | 3a |
| (1)-165 | — | 2b | 5a | — | 3c |
| (1)-166 | — | 2b | 5e | — | 3a |
| (1)-167 | — | 2b | 5i | — | 3a |
| (1)-168 | — | 2b | 5q | — | 3a |
| (1)-169 | — | 2a | 5a | — | 3a |
| (1)-170 | — | 2a | 5e | — | 3a |
| (1)-171 | — | 2a | 5i | — | 3a |
| (1)-172 | — | 2a | 5q | — | 3a |
| (1)-173 | — | 2a | 5a | — | 3c |
| (1)-174 | — | 2a | 5e | — | 3a |
| (1)-175 | — | 2a | 5i | — | 3a |
| (1)-176 | — | 2a | 5q | — | 3a |
| (1)-177 | — | 2a | 5k | — | 3a |
| (1)-178 | — | 2b | 5k | — | 3a |
| (1)-179 | — | 2a | 5k | — | 3c |
| (1)-180 | — | 2b | 5k | — | 3c |
| (1)-181 | — | 2a | 5m | — | 3a |
| (1)-182 | — | 2b | 5m | — | 3a |
| (1)-183 | — | 2a | 5m | — | 3c |
| (1)-184 | — | 2b | 5m | — | 3c |
| (1)-185 | — | 2a | 5o | — | 3a |
| (1)-186 | — | 2b | 5o | — | 3a |
| (1)-187 | — | 2a | 5o | — | 3c |
| (1)-188 | — | 2b | 5o | — | 3c |
| (1)-189 | — | 2a | 5q | — | 3a |
| (1)-190 | — | 2b | 5q | — | 3a |
| (1)-191 | — | 2a | 5q | — | 3c |
| (1)-192 | — | 2b | 5q | — | 3c |
| (1)-193 | — | 2a | 5k | 4a | 3a |
| (1)-194 | — | 2b | 5k | 4a | 3a |
| (1)-195 | — | 2a | 5k | 4a | 3c |
| (1)-196 | — | 2b | 5k | 4a | 3c |
| (1)-197 | — | 2a | 5m | 4a | 3a |
| (1)-198 | — | 2b | 5m | 4a | 3a |
| (1)-199 | — | 2a | 5m | 4a | 3c |
| (1)-200 | — | 2b | 5m | 4a | 3c |
| (1)-201 | — | 2a | 5o | 4a | 3a |
| (1)-202 | — | 2b | 5o | 4a | 3a |
| (1)-203 | — | 2a | 5o | 4a | 3c |
| (1)-204 | — | 2b | 5o | 4a | 3c |
| (1)-205 | — | 2a | 5q | 4a | 3a |
| (1)-206 | — | 2b | 5q | 4a | 3a |
| (1)-207 | — | 2a | 5q | 4a | 3c |
| (1)-208 | — | 2b | 5q | 4a | 3c |

In some embodiments, the compound of the disclosure is selected from:

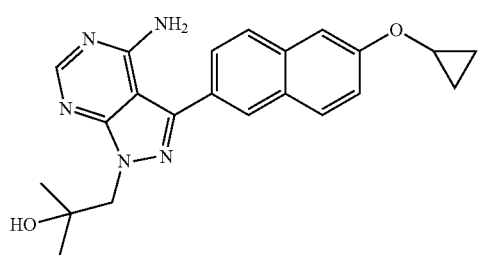 [SMILES: CC(C)(O)Cn1nc(-c2ccc3cc(OC4CC4)ccc3c2)c2c(N)ncnc21]

1-(4-amino-3-(6-cyclopropoxynaphthalen-2-yl)-1H-pyrazolo[3,4-d]pyrimidin-1-yl)-2-methylpropan-2-ol;

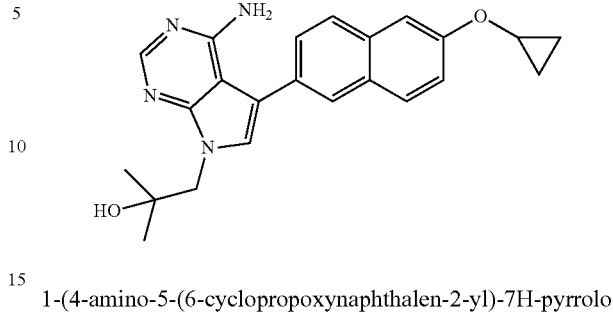

1-(4-amino-5-(6-cyclopropoxynaphthalen-2-yl)-7H-pyrrolo[2,3-d]pyrimidin-7-yl)-2-methylpropan-2-ol;

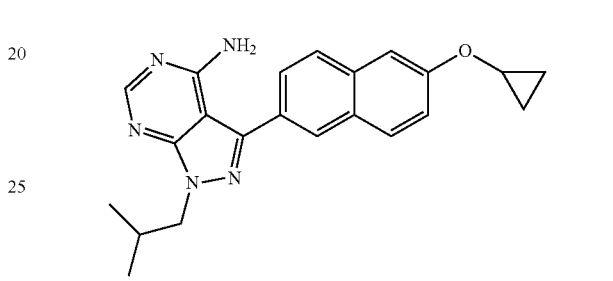

3-(6-cyclopropoxynaphthalen-2-yl)-1-isobutyl-1H-pyrazolo[3,4-d]pyrimidin-4-amine

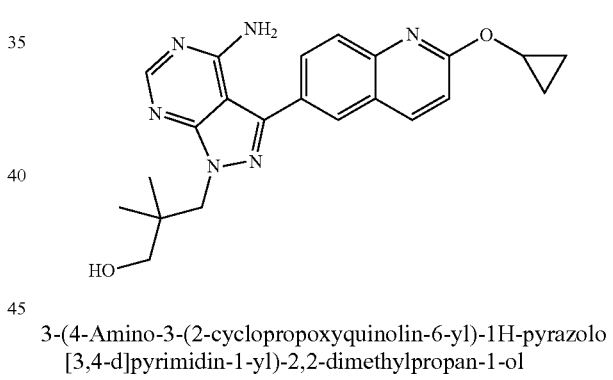

3-(4-Amino-3-(2-cyclopropoxyquinolin-6-yl)-1H-pyrazolo[3,4-d]pyrimidin-1-yl)-2,2-dimethylpropan-1-ol
and

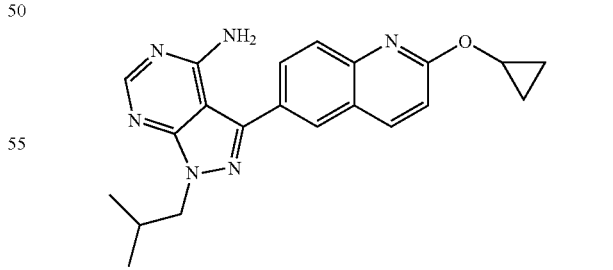

3-(2-cyclopropoxyquinolin-6-yl)-1-isobutyl-1H-pyrazolo[3,4-d]pyrimidin-4-amine.

One embodiment of the present disclosure provide a method of treating a subject in need of treatment for an apicomplexan-related disease comprising administering an effective amount of a compound of the disclosure or any embodiment thereof, that inhibits the activity of an apicomplexan calcium dependent protein kinase (CDPK).

Particular embodiments of the present disclosure provide a method of treating cryptosporidiosis in a subject comprising administering an effective amount of a compound of the disclosure, that inhibits the activity of *Cryptosporidium parvum* and *C. hominus* calcium dependent protein kinase 1 (CpCDPK1).

Other particular embodiments of the present disclosure provide a method of treating cryptosporidiosis in a subject comprising administering an effective amount of a compound of the disclosure, that inhibits the activity of *T. gondii*, calcium dependent protein kinase 1 (TgCDPK1).

Other particular embodiments of the present disclosure provide a method of treating cryptosporidiosis in a subject comprising administering an effective amount of a compound of the disclosure, that inhibits the activity of *P. falciparum* or *P. berghei* calcium dependent protein kinase 4 (PfCDPK4 or PbCDPK4).

Optionally, the compound of any one the compounds of the disclosure, can be administered in combination with a second agent, such as agents specific for use against the specific apicomplexan-related disorder being treated.

In one embodiment, the apicomplexan protozoan related disease is toxoplasmosis. As understood by one of ordinary skill in the art, toxoplasmosis can encompass a number of pathologies, including, but not limited to, encephalitis, retinitis, lymphadenopathy, disseminated disease, and hepatitis. Toxoplasmosis infects most genera of warm-blooded animals, including humans, but the primary host is the felid (cat) family.

Cats are the definitive host for the *Toxoplasma* organism. Infection with this protozoan parasite is fairly common, but actual disease caused by this parasite is relatively rare in cats. Cats can become infected by *Toxoplasma* by eating any of the three infective stages of the parasites. The most common route of infection is probably by ingestion of tissue cysts in infected prey or in other raw meat. *Toxoplasma* multiply in the small intestines and in approximately two to three weeks the oocysts are excreted in the infected cat's feces. In another example, cats may be treated prophylactically for toxoplasmosis (e.g, a gastrointestinal infection) provided by providing a therapeutically effective amount of compounds of the disclosure or to eliminate the chance that they would shed infectious *Toxoplasmodia* oocyts and infect their owners. In another embodiment, infected cats may be treated by providing a therapeutically effective amount of a compound of the disclosure to treat toxoplasmosis. As will be understood by those of skill in the art, similar prophylactic and therapeutic methods for limiting development of or treating toxoplasmosis can be used in any animal that can be infected by *Toxoplasma* sp.

Animals are infected by eating infected meat, by ingestion of feces of a cat that has itself recently been infected, or by transmission from mother to fetus. While cats are often blamed for spreading toxoplasmosis, contact with raw meat is a more significant source of human infections in many countries, and fecal contamination of hands is a greater risk factor. Infection has two stages (1) acute toxoplasmosis; and (2) latent toxoplasmosis. During acute toxoplasmosis, symptoms are often influenza-like: swollen lymph nodes, or muscle aches and pains that last for a month or more. Rarely, a patient with a fully functioning immune system may develop eye damage from toxoplasmosis. Young children (15 years old or younger) and immunocompromised patients, such as those with HIV/AIDS, those taking certain types of chemotherapy, or those who have recently received an organ transplant, may develop severe toxoplasmosis. In an embodiment, a young child can be 14 years old or younger; or 13 years old or younger; or 12 years old or younger; or 11 years old or younger; or 10 years old or younger; or 9 years old or younger; or 8 years old or younger; or 7 years old or younger; or 6 years old or younger; or 5 years old or younger; or 4 years old or younger; or 3 years old or younger; or 2 years old or younger; or 1 year old or younger. This can cause damage to the brain (encephalitis) or the eyes (necrotizing retinochoroiditis). Infants infected via placental transmission may be born with either of these problems, or with nasal malformations, although these complications are rare in newborns. In most immunocompetent patients, the infection enters a latent phase, during which only bradyzoites are present, forming cysts in nervous and muscle tissue. Most infants who are infected while in the womb have no symptoms at birth but may develop symptoms later in life. The most common current therapy for toxoplasmosis is sulfadiazine/pyrimethamine combination therapy, but therapy is often limited by allergic reactions to the sulfa component, anemia and pancytopenia induced by blocking the folate pathway. When sulfadiazine cannot be used, clindamycin may be combined with pyrimethamine but most experts feel it does not work as well as sulfadiazine. Spiramycin has been used for toxoplasmosis during pregnancy but has issues with low efficacy and is no longer available in the United States. Thus few therapeutic alternatives are available.

In another embodiment, the apicomplexan protozoan related disease is cryptosporidiosis. Cryptosporidiosis is caused by infection with the single-celled parasite (not bacterium) *Cryptosporidium parvum*. This parasite is found in many mammals including lambs, calves, goat kids, piglets and humans. Research so far has shown two basic types, the bovine type which affects most species, and a second human type which causes disease in humans only. Outbreaks of human disease, where large numbers of people are affected, are usually water-borne and usually associated with the bovine type of *cryptosporidium*. Individual sporadic cases of cryptosporidiosis in humans are mostly (around 60%) associated with the human type of *cryptosporidium*.

Cryptosporidiosis affects the intestines of mammals and is typically an acute short-term infection. It is spread through the fecal-oral route, often through contaminated water; the main symptom is self-limiting diarrhea in people with intact immune systems. In immunocompromised individuals, such as HIV/AIDS patients, the symptoms are particularly severe and often fatal. *Cryptosporidium* is the organism most commonly isolated in HIV positive patients presenting with diarrhea. Cryptosporidiosis is one of the most common waterborne diseases and is found worldwide. The parasite is transmitted by environmentally hardy microbial cysts (oocysts) that, once ingested, exist in the small intestine and result in an infection of intestinal epithelial tissue. Infection is through contaminated material such as earth, water, uncooked or cross-contaminated food that has been in contact with the feces of an infected individual or animal. It is especially prevalent amongst those in regular contact with bodies of fresh water including recreational water such as swimming pools. Other potential sources include insufficiently treated or insufficiently filtered water water supplies, contaminated food, or exposure to feces. Symptoms appear from two to ten days after infection, and last for up to two weeks or more. In immunocompetent people, the disease can be asymptomatic or cause acute diarrhea or persistent diarrhea that can last for a few weeks. There is often stomach pain or cramping and a low fever. Other symptoms may include nausea, vomiting, malabsorption, and dehydration. Individuals who are asymptomatic (have no symptoms) are nevertheless infective. Immunocompromised people, as well as very young or very old people, can develop a more severe form of cryptosporidiosis. When *Cryptosporidium* spreads beyond the intestine, as it can predominantly in patients with AIDS, it can reach the lungs, middle ear, pancreas, and stomach. Thus, one symptom is pain in the right upper quadrant. The parasite can infect the biliary tract, causing biliary cryptosporidiosis. This can result in cholecystitis and cholangitis. Current treatment is symptomatic, with fluid rehydration, electrolyte correction and management of any pain. Nitazoxanide has been FDA-approved for treatment of diarrhea caused by *Cryptosporidium* in people with healthy immune systems and is available by prescription, however it only shortens the duration of diarrhea by a couple of days. The effectiveness of nitazoxanide in immunosuppressed individuals is unclear and multiple trials have shown no benefit.

The inhibitors described herein may have use in other apicoplexa protozoan related diseases, such as sarcocystosis caused by *Sarcocystis neurona* which is the most common cause of equine protozoal myeloencephalitis (EPM) in horses in America and is transmitted by fecal contamination by opossums, neurosporosis caused by *Neurospora caninum* which causes epidemic abortions in cattle and sheep and is transmitted by canine species fecal contamination and verticle transmissions from mother to calf or lamb, cystoisosporosis caused by *Cystoisospora suis* and causes epidemic diarrhea in pigs and other species in humans and animals, besnoitiosis caused by *Besnoitia besnoiti* is found as a skin and systemic disease of cattle, coccidiosis caused by *Eimeria* spp., cause infections and disease in poultry; which causes Babesiosis which is caused by *Babesia* spp. and results in a malaria-like disease, theileriosis a tick transmitted disease caused by *Theileria equi* and other species and causes a wasting disease in horses and other livestock, and malaria in humans and animals caused by *Plasmodium* spp. In general, calcium dependent protein kinases homologous to *Toxoplasma* and *Cryptosporidium* probably play important roles in the infection by these pathogens as we have examples of the above compounds that are active against the CDPKs of these apicoplexa protozoans and stop infection by these protozoans in vitro, and in the case of *S. neurona* and *N. caninum*, also evidence that therapy with these compounds successfully cure mouse infections with these protozoa.

*Neospora caninum* is a cyst-forming apicomplexan parasite. It is closely related to *Toxoplasma gondii*, but *N. caninum* exhibits distinct differences in transmission patterns, virulence, host specificity, immunogenetic aspects, and the pathology they induce. *N. caninum* represents one of the most important infectious causes of bovine abortion, stillbirth, and the birth of weak calves. The reservoir is the canid, such as dogs and wild foxes and wolves, and cattle are infected both by accidental ingestion of canine feces or by vertical transmission from mother cow to calf. In addition, *N. caninum* causes neosporosis, a neuromuscular disease in dogs. Neosporosis has also been detected in a wide range of other species of livestock and wild animals.

*Plasmodium* calcium dependent protein kinase 4 (CDPK4) is essential for exflaggelation of microgametes, sexual reproduction and infection of the mosquito host and is a potential drug target to block mosquito transmission. *Plasmodium* transmission-blocking compounds that act via inhibition of PfCDPK4 have great promise in the armamentarium of malaria control. *Plasmodium* CDPK4 has a unique ATP binding site which renders CDPK4 differentially sensitive to bumped kinase inhibitors (BKIs). TgCDPK1 and CpCDPK1 have ATP-binding pockets with an atypically small gatekeeper residue, glycine. *P. falciparum* CDPK4 (PfCDPK4) has a serine residue at the gatekeeper position, smaller than any gatekeeper in mammalian kinases, and an overall ATP-binding pocket that is very similar to TgCDPK1 and CpCDPK1. BKIs inhibit *P. falciparum* CDPK4 (PfCDPK4) and prevents the exflagellation of malaria microgametes. Administration of BKIs to mice stops the transmission of *P. berghei* to mosquitoes. Finally, addition of BKIs to blood containing *P. falciparum* gametocytes stops exflagellation of microgametocytes and blocks the infection of mosquitoes. BKIs are non-toxic, selective inhibitors that block malaria transmission to mosquitos, have favorable oral pharmacokinetic (PK) properties, and have a low likelihood of generating resistance.

Thus, other particular embodiments of the present disclosure provide a method for treating malaria comprising administering an effective amount of a compound of the disclosure that inhibits the activity of *Plasmodium falciparum* and *P. berghei* calcium dependent protein kinases. In one embodiment, the compound can be administered in combination with a second agent. In another embodiment, the subject has malaria, and the second agent is an antimalarial therapeutic. The subject can be human. In further embodiments, the subject is a mammal other than a human, such as a cat or livestock (e.g., pigs, sheep, goats, cattle).

Pharmaceutical Compositions

In some embodiments, the method comprises the administration of BKI in a pharmaceutical composition having at least one pharmaceutically acceptable carrier, solvent, adjuvant or diluent.

The compounds described herein may be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. The pharmaceutical compositions described herein may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known in the art for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques. In some cases such coatings may be prepared by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Formulations for oral use may also be presented as lozenges.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an antioxidant such as ascorbic acid.

Pharmaceutical compositions of the invention may also be in the form of oil-in-water emulsions. The oily phase may be a vegetable oil or a mineral oil or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol, glucose or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be a sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compositions disclosed herein may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient. The daily dose can be administered in one to four doses per day. In the case of skin conditions, it may be preferable to apply a topical preparation of compounds of this invention to the affected area two to four times a day.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy. The compounds of the present invention may be administered alone or in combination with at least one additional therapeutic agent. The compounds of the present invention may be combined with one or more additional therapeutic agents simultaneously or sequentially.

Definitions

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural or singular number, respectively. Additionally, the words "herein," "above" and "below" and words of similar import, when used in this application, shall refer to this application as a whole and not to any particular portions of this application.

Terms used herein may be preceded and/or followed by a single dash, "-", or a double dash, "=", to indicate the bond order of the bond between the named substituent and its parent moiety; a single dash indicates a single bond and a double dash indicates a double bond. In the absence of a single or double dash it is understood that a single bond formed between the substituent and its parent moiety; further, substituents are intended to be read "left to right" unless a dash indicates otherwise. For example, $C_1$-$C_6$alkoxycarbonyloxy and —OC(O)$C_1$-$C_6$alkyl indicate the same functionality; similarly arylalkyl and -alkylaryl indicate the same functionality.

The term "alkenyl" as used herein, means a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkyl" as used herein, means a straight or branched chain hydrocarbon containing from 1 to 10 carbon atoms, unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —$CH_2$—, —$CH_2CH_2$—, —$CH_2CH_2CHC(CH_3)$—, —$CH_2CH(CH_2CH_3)CH_2$—.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl," as used herein, means a phenyl (i.e., monocyclic aryl), a bicyclic ring system containing at least one phenyl ring or an aromatic bicyclic ring containing only carbon atoms in the aromatic bicyclic ring system or a multicyclic aryl ring system, provided that the bicyclic or multicyclic aryl ring system does not contain a heteroaryl ring when fully aromatic. The bicyclic aryl can be azulenyl, naphthyl, or a phenyl fused to a monocyclic cycloalkyl, a monocyclic cycloalkenyl, or a monocyclic heterocyclyl. The bicyclic aryl is attached to the parent molecular moiety through any carbon atom contained within the phenyl portion of the bicyclic system, or any carbon atom with the napthyl or azulenyl ring. The fused monocyclic cycloalkyl or monocyclic heterocyclyl portions of the bicyclic aryl are optionally substituted with one or two oxo and/or thia groups. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-7-yl, 2,3-dihydrobenzo[b][1,4]dioxan-5-yl, 2,3-dihydrobenzo[b][1,4]dioxan-6-yl, 2H-benzo[b][1,4]oxazin3(4H)-on-5-yl, 2H-benzo[b][1,4]oxazin3(4H)-on-6-yl, 2H-benzo[b][1,4]oxazin3(4H)-on-7-yl, 2H-benzo[b][1,4]oxazin3(4H)-on-8-yl, benzo[d]oxazin-2(3H)-on-5-yl, benzo[d]oxazin-2(3H)-on-6-yl, benzo[d]oxazin-2(3H)-on-7-yl, benzo[d]oxazin-2(3H)-on-8-yl, quinazolin-4(3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo[d]thiazol-2(3H)-on-4-yl, benzo[d]thiazol-2(3H)-on-5-yl, benzo[d]thiazol-2(3H)-on-6-yl, and benzo[d]thiazol-2(3H)-on-7-yl. In certain embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted with one or two groups which are independently oxo or thia. Multicyclic aryl groups are a phenyl ring (base ring) fused to either (i) one ring system selected from the group consisting of a bicyclic aryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic cycloalkyl, a monocyclic or bicyclic cycloalkenyl, and a monocyclic or bicyclic heterocyclyl, provided that when the base ring is fused to a bicyclic cycloalkyl, bicyclic cycloalkenyl, or bicyclic heterocyclyl, then the base ring is fused to the base ring of the a bicyclic cycloalkyl, bicyclic cycloalkenyl, or bicyclic heterocyclyl. The multicyclic aryl is attached to the parent molecular moiety through any carbon atom contained within the base ring. In certain embodiments, multicyclic aryl groups are a phenyl ring (base ring) fused to either (i) one ring system selected from the group consisting of a bicyclic aryl, a bicyclic cycloalkyl, a bicyclic cycloalkenyl, and a bicyclic heterocyclyl; or (ii) two other ring systems independently selected from the group consisting of a phenyl, a monocyclic cycloalkyl, a monocyclic cycloalkenyl, and a monocyclic heterocyclyl, provided that when the base ring is fused to a bicyclic cycloalkyl, bicyclic cycloalkenyl, or bicyclic heterocyclyl, then the base ring is fused to the base ring of the a bicyclic cycloalkyl, bicyclic cycloalkenyl, or bicyclic heterocyclyl. Examples of multicyclic aryl groups include but are not limited to anthracen-9-yl and phenanthren-9-yl.

The term "arylalkyl" and "-alkylaryl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The terms "cyano" and "nitrile" as used herein, mean a —CN group.

The term "cycloalkyl" as used herein, means a monocyclic, bicyclic, or a multicyclic cycloalkyl ring system. Monocyclic ring systems are cyclic hydrocarbon groups containing from 3 to 8 carbon atoms, where such groups can be saturated or unsaturated, but not aromatic. In certain embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —$(CH_2)_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted with one or two groups which are independently oxo or thia. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. Multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other rings systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic cycloalkyl is attached to the parent molecular moiety through any carbon atom contained within the base ring. In certain embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other rings systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

"Cycloalkenyl" as used herein refers to a monocyclic, bicyclic, or a multicyclic cycloalkenyl ring system. Monocyclic ring systems are cyclic hydrocarbon groups containing from 3 to 8 carbon atoms, where such groups are unsaturated (i.e., containing at least one annular carbon-carbon double bond), but not aromatic. Examples of monocyclic ring systems include cyclopentenyl and cyclohexenyl. Bicyclic cycloalkenyl rings are bridged monocyclic rings or fused bicyclic rings. Bridged monocyclic rings contain a monocyclic cycloalkenyl ring where two non-adjacent carbon atoms of the monocyclic ring are linked by an alkylene bridge of between one and three additional carbon atoms (i.e., a bridging group of the form —(CH$_2$)$_w$—, where w is 1, 2, or 3). Representative examples of bicyclic cycloalkenyls include, but are not limited to, norbornenyl and bicyclo[2.2.2]oct-2-enyl. Fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. The bridged or fused bicyclic cycloalkenyl is attached to the parent molecular moiety through any carbon atom contained within the monocyclic cycloalkenyl ring. Cycloalkenyl groups are optionally substituted with one or two groups which are independently oxo or thia. Multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two rings systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic cycloalkenyl is attached to the parent molecular moiety through any carbon atom contained within the base ring. In certain embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two rings systems independently selected from the group consisting of a phenyl, a monocyclic heteroaryl, a monocyclic cycloalkyl, a monocyclic cycloalkenyl, and a monocyclic heterocyclyl.

The term "halo" or "halogen" as used herein, means —Cl, —Br, —I or —F.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl," as used herein, means a monocyclic, bicyclic, or a multicyclic heteroaryl ring system. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The fused cycloalkyl or heterocyclyl portion of the bicyclic heteroaryl group is optionally substituted with one or two groups which are independently oxo or thia. When the bicyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. When the bicyclic heteroaryl is a monocyclic heteroaryl fused to a phenyl ring or a monocyclic heteroaryl, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4(5H)-onyl. In certain embodiments, the fused bicyclic heteroaryl is a 5 or 6 membered monocyclic heteroaryl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused cycloalkyl, cycloalkenyl, and heterocyclyl groups are optionally substituted with one or two groups which are independently oxo or thia. The multicyclic heteroaryl group is a monocyclic heteroaryl ring (base ring) fused to either (i) one ring system selected from the group consisting of a bicyclic aryl, a bicyclic heteroaryl, a bicyclic heterocyclyl, a bicyclic cycloalkenyl, and a bicyclic cycloalkyl; or (ii) two ring systems selected from the group consisting of a phenyl, a bicyclic aryl, a monocyclic or bicyclic heteroaryl, a monocyclic or bicyclic heterocyclyl, a monocyclic or bicyclic cycloalkenyl, and a monocyclic or bicyclic cycloalkyl. The multicyclic heteroaryl group is connected to the parent molecular moiety through any carbon atom or nitrogen atom contained within the base ring. In certain embodiments, multicyclic heteroaryl groups are a monocyclic heteroaryl ring (base ring) fused to either (i) one ring system selected from the group consisting of a bicyclic aryl, a bicyclic heteroaryl, a bicyclic heterocyclyl, a bicyclic cycloalkenyl, and a bicyclic cycloalkyl; or (ii) two ring systems selected from the group consisting of a phenyl, a monocyclic heteroaryl, a monocyclic heterocyclyl, a monocyclic cycloalkenyl, and a monocyclic cycloalkyl. Examples of multicyclic heteroaryls include, but are not limited to 5H-[1,2,4]triazino[5,6-b]indol-5-yl, 2,3,4,9-tetrahydro-1H-carbazol-9-yl, 9H-pyrido[3,4-b]indol-9-yl, 9H-carbazol-9-yl, acridin-9-yl, The term "heteroarylalkyl" and "-alkylheteroaryl" as used herein, means a heteroaryl, as defined herein, appended to the parent molecular moiety through an alkyl group, as defined herein. Representative examples of heteroarylalkyl include, but are not limited to, fur-3-ylmethyl, 1H-imidazol-2-ylmethyl, 1H-imidazol-4-ylmethyl, 1-(pyridin-4-yl)ethyl, pyridin-3-ylmethyl, pyridin-4-ylmethyl, pyrimidin-5-ylmethyl, 2-(pyrimidin-2-yl)propyl, thien-2-ylmethyl, and thien-3-ylmethyl.

The term "heterocyclyl" as used herein, means a monocyclic, bicyclic, or multicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to either a phenyl, a monocyclic cycloalkyl, a monocyclic cycloalkenyl, a monocyclic heterocycle, or a monocyclic heteroaryl. The bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. Heterocyclyl groups are optionally substituted with one or two groups which are independently oxo or thia. In certain embodiments, the bicyclic heterocyclyl is a 5 or 6 membered monocyclic heterocyclyl ring fused to phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other rings systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In certain embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other rings systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5-yl, 1,2,3,4-tetrahydropyrido[4,3-g]isoquinolin-2-yl, 12H-benzo[b]phenoxazin-12-yl, and dodecahydro-1H-carbazol-9-yl.

The term "nitro" as used herein, means a —NO$_2$ group.

The term "oxo" as used herein means a =O group.

The term "saturated" as used herein means the referenced chemical structure does not contain any multiple carbon-carbon bonds. For example, a saturated cycloalkyl group as defined herein includes cyclohexyl, cyclopropyl, and the like.

The term "thia" as used herein means a =S group.

The term "unsaturated" as used herein means the referenced chemical structure contains at least one multiple carbon-carbon bond, but is not aromatic. For example, an unsaturated cycloalkyl group as defined herein includes cyclohexenyl, cyclopentenyl, cyclohexadienyl, and the like.

The compounds of this invention may contain one or more asymmetric carbon atoms, so that the compounds can exist in different stereoisomeric forms. These compounds can be, for example, racemates, chiral non-racemic or diastereomers. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent; chromatography, using, for example a chiral HPLC column; or derivatizing the racemic mixture with a resolving reagent to generate diastereomers, separating the diastereomers via chromatography, and removing the resolving agent to generate the original compound in enantiomerically enriched form. Any of the above procedures can be repeated to increase the enantiomeric purity of a compound.

When the compounds described herein contain olefinic double bonds or other centers of geometric asymmetry, and unless otherwise specified, it is intended that the compounds include the cis, trans, Z- and E-configurations. Likewise, all tautomeric forms are also intended to be included.

As used herein, the phrase "pharmaceutically acceptable salt" refers to both pharmaceutically acceptable acid and base addition salts and solvates. Such pharmaceutically acceptable salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—$(CH_2)_n$—COOH where n is 0-4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

As used herein, the term "subject", "individual," or "patient," used interchangeably, refers to any animal, including mammals, preferably mice, rats, other rodents, rabbits, dogs, cats, birds, swine, horses, livestock (e.g., pigs, sheep, goats, cattle), primates or humans.

As used here, a subject "in need thereof" refers to a subject that has the disorder or disease to be treated or is predisposed to or otherwise at risk of developing the disease or disorder.

As used here, the terms "treatment" and "treating" means:
(i) inhibiting the progression the disease;
(ii) prophylactic use for example, preventing or limiting development of a disease, condition or disorder in an individual who may be predisposed or otherwise at risk to the disease, condition or disorder but does not yet experience or display the pathology or symptomatology of the disease;
(iii) inhibiting the disease; for example, inhibiting a disease, condition or disorder in an individual who is experiencing or displaying the pathology or symptomatology of the disease, condition or disorder;
(iv) ameliorating the referenced disease state, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease; or
(v) eliciting the referenced biological effect.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician, which includes one or more of the following: (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder; and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

EXAMPLES

The methods of the disclosure are illustrated further by the following examples, which are not to be construed as limiting the disclosure in scope or spirit to the specific procedures and in them. It is understood that the nature of the substituents required for the desired target compound often determines the preferred method of synthesis.

General Synthetic Procedures

All chemicals were purchased from commercial suppliers and used without further purification unless otherwise stated. Reactions were monitored with thin-layer chromatography using silica gel 60 F254 coated glass plates (EM Sciences). Compound purification was performed with an IntelliFlash 280 automated flash chromatography system using pre-packed Varian Super Flash silica gel columns (hexanes/EtOAc or $CH_2Cl_2$/MeOH gradient solvent systems). A Varian Dynamax Microsorb 100-5 $C_{18}$ column (250 mm×21.4 mm), eluting with $H_2O/CH_3CN$ or $H_2O$/MeOH gradient solvent systems (+0.05% TFA) was used for preparatory HPLC purification. Products were detected by UV at $\lambda$=254 nm, with all final compounds displaying >95% purity. NMR spectra were recorded on Bruker 300 or 500 MHz spectrometers at ambient temperature. Chemical shifts are reported in parts per million ($\delta$) and coupling constants in Hz. $^1$H-NMR spectra were referenced to the residual solvent peaks as internal standards (7.26 ppm for $CDCl_3$, 2.50 ppm for $d_6$-DMSO, and 3.34 ppm for $CD_3OD$). Mass spectra were recorded with a Bruker Esquire Liquid Chromatograph—Ion Trap Mass Spectrometer.

In some examples and embodiments, the methods useful in synthesis of the inhibitors of disclosure have been previously described in International Patent Publication WO 2011/0094628 and the U.S. Patent Publication 2013/0018040, both incorporated herein by reference in their entirety.

Methods of Preparation

The exemplary synthetic routes described below can be used to generate derivatives that contain varying substituents at the 1- and 3-positions of the pyrazolopyrimidine or imidazopyrazine core.

General $R_2$ Alkylation Procedure:

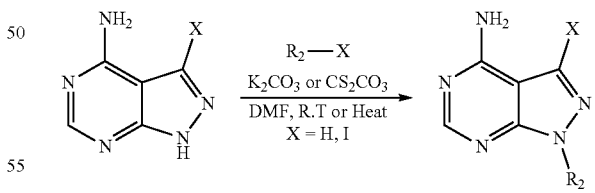

Pyrazolopyrimidine (1 equiv.), $K_2CO_3$, $Cs_2CO_3$ or $K_2CO_3$:$NaH_2PO_4$ (1.5-2 equiv.), and an alkylhalide (1.1 equiv.) or alkylmesylate (1.1 equiv.) were stirred in dry DMF at room temperature or 80° C. The reaction was monitored by thin layer chromatography. After completion, ethyl acetate and water were added and the organic phase was separated. The water phase was extracted with ethyl acetate. The combined organic phases were washed with brine, dried over $Na_2SO_4$ and evaporated under reduced pressure. The crude product was then purified via flash chromatography over silica, eluting with either a hexanes/ EtOAc or CH₂Cl₂/MeOH gradient. If necessary, further purification was performed with preparatory RP-HPLC.

General Suzuki Coupling Procedure:

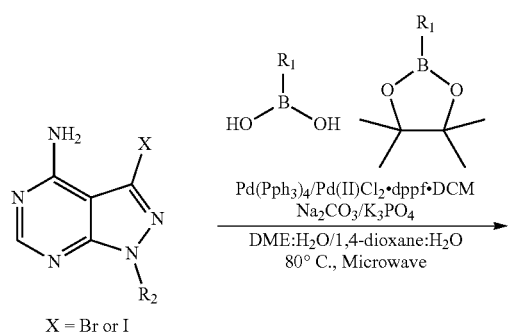

3-Iodopyrazolopyrimidines or 3-Bromopyrazolopyrimidines (1 equiv.), Na₂CO₃/K₃PO₄ (2-4 equiv.), Pd(PPh₃)₄/Pd(II)Cl₂dppf.DCM, (0.05 equiv.), and boronic acids or boronate pinacol esters (1-2 equiv.) were dissolved in a mixture of dimethoxyethane (1.5 mL) and water (0.5 mL) and then heated in a microwave at 80° C. for one hour. After cooling, ethyl acetate and water were added and the organic phase was separated. The water phase was extracted with ethyl acetate. The combined organic phases were washed with brine, dried over Na₂SO₄ and evaporated under reduced pressure. The crude product was then purified via flash chromatography over silica, eluting with either a hexanes/ EtOAc or CH₂Cl₂/MeOH gradient. If necessary, further purification was performed with preparatory RP-HPLC.

General Naphthol Alkylation Procedure:

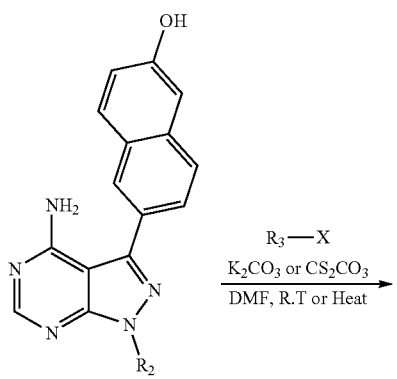

6-Hydroxy-2-naphthalene pyrazolopyrimidines (1 equiv.), K₂CO₃/CS₂CO₃ or (1.5-2 equiv.), and alkyl halides/ epoxides (1.1 equiv.), NaH₂PO₄: K₂CO₃ (1:1 equiv.), were stirred in dry DMF at room temperature or 60-80° C. and monitored by thin layer chromatography. After completion, ethyl acetate and water were added and the organic phase was separated. The water phase was extracted with ethyl acetate. The combined organic phases were washed with brine, dried over Na₂SO₄ and evaporated under reduced pressure. The crude product was then purified via flash chromatography over silica, eluting with either a hexanes/ EtOAc or CH₂Cl₂/MeOH gradient. If necessary, further purification was performed with preparatory RP-HPLC.

General Boc-Deprotection Procedure:

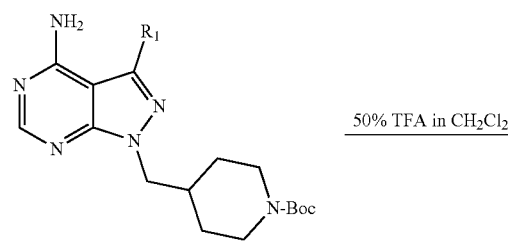

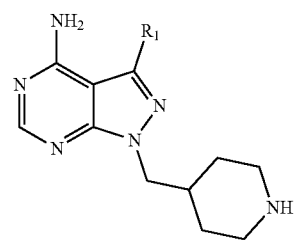

Boc-amine-containing pyrazolopyrimidines was stirred in a TFA/CH₂Cl₂ (1:1) mixture for 3 h. The reaction was then concentrated and purified via preparatory RP-HPLC. After HPLC purification, the product was then re-concentrated from 1.25 M HCl in EtOH to afford the final, purified product as a bis-HCl salt.

General Reductive Amination Procedure:

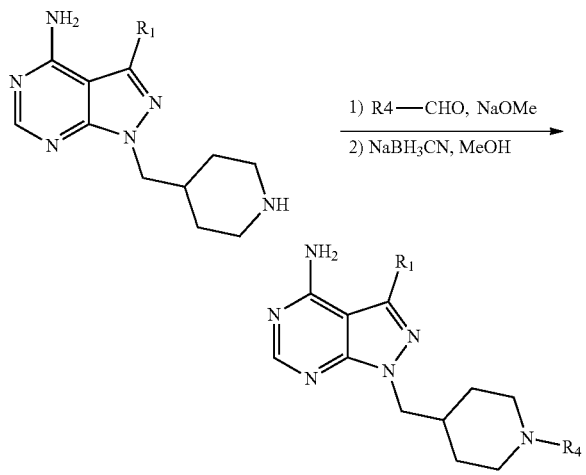

Deprotected pyrazolopyrimidines (1 equiv.) were dissolved in methanol and neutralized with sodium methoxide. A solution containing 2% acetic acid and an aldehyde or ketone (5-10 equiv.) was stirred at room temperature for 10 min. Sodium cyanoborohydride (5 equiv.) was then added and the reaction was stirred until reaching completion, as determined by thin layer chromatography (typically ~2 h). The reaction crude was then purified via preparatory RP-HPLC. After HPLC purification, the residue was dissolved in a small amount of 2 M HCl in methanol and, after concentration in vacuo, the final product was obtained as an HCl salt.

General Pinacol Ester Formation Procedure:

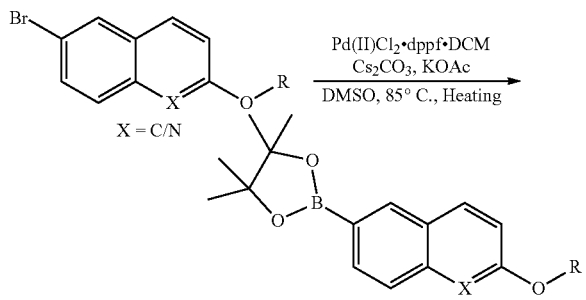

Alkylated naphthols or quinolones (1 equiv.), Cs$_2$CO$_3$ (1.5-2 equiv.), pinacolatodiborane (2.0 equiv.), Pd(II)Cl$_2$ (dppf)·DCM (0.05 equiv.), and KOAc (1 equiv.) in dry DMSO were heated at 85° C. for 5-8 h. After completion, ethyl acetate and water were added and the organic phase was separated. The water phase was extracted with ethyl acetate. The combined organic phases were washed with brine, dried over Na$_2$SO$_4$ and evaporated under reduced pressure. The crude product was then purified via flash chromatography over silica, eluting with a hexanes/EtOAc solvent gradient.

General Procedure for Boronylation Using Triisopropylborate:

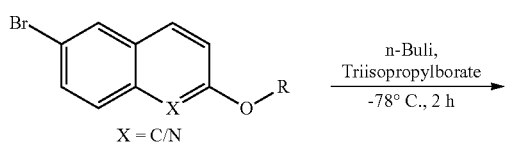

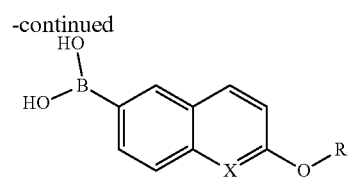

Aryl halides (1 equiv.) and triisopropylborate (1.5 equiv.) were dissolved in tetrahydrofuran:toluene (2:8), cooled to −78° C., and n-Buli (1.7 equiv.) was added dropwise over 30-40 min. After addition, the reaction was stirred at −78° C. for 1 h. After 1 h, the reaction was allowed to warm to 0° C. and stirred for 15-25 min followed by addition of 2N HCl slowly. The organic layer was separated and concentrated in vacuo to afford the desired crude product as a white crystalline product or by collecting and washing with water the white crystalline solid that forms upon addition of 2N HCl.

Example 1: 3-(6-Cyclobutoxynaphthalen-2-yl)-1-((1-methylpiperidin-4-yl)methyl)-1H-pyrazolo[3,4-d]pyrimidin-4-amine

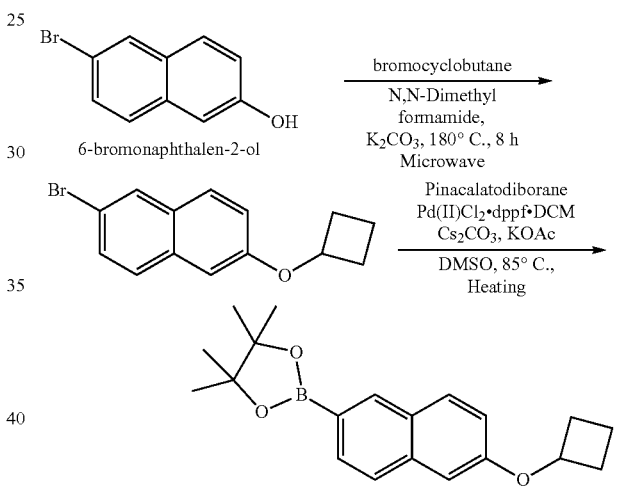

2-Bromo-6-cyclobutoxynaphthalene: 6-bromonaphthalene (700 mg, 3.1 mmol), K$_2$CO$_3$ (2.140 g, 15.5 mmol), and bromocyclobutane (1.75 mL, 18.6 mmol) in dry DMF were heated at 180° C. in a microwave for 8 h. After completion, ethyl acetate and water were added and the organic phase was separated. The aqueous phase was extracted with ethyl acetate (2×10 mL). The combined organic phases were washed with brine, dried over Na$_2$SO$_4$ and evaporated under reduced pressure. The crude product was then purified via flash chromatography over silica, eluting with a hexanes/EtOAc solvent gradient to afford 693 mg (80% yield) of pure product. $^1$H NMR (300 MHz, CDCl$_3$) δ7.88 (s, 1H), 7.65-7.43 (m, 3H), 7.10 (dd, 1H), 6.94 (s, 1H), 4.74 (m, 1H), 2.58-2.45 (m, 2H), 2.30-2.13 (m, 2H), 1.95-1.69 (m, 2H); MS (ESI) 278.5 m/z [MH$^+$], C$_{14}$H$_{14}$BrO requires 278.2.

2-(6-Cyclobutoxynaphthalen-2-yl)-4,4,5,5-tetramethyl-1,3,2-dioxaborolane: 2-Bromo-6-cyclobutoxynaphthalene and pinacolatodiborane were subjected to general pinacol ester formation procedure to afford the desired pure product (631 mg, 60% yield); $^1$H NMR (300 MHz, CDCl$_3$) δ 8.26 (s, 1H), 7.93-7.61 (m, 3H), 7.2-6.93 (m, 2H), 4.80 (m, 1H), 2.67-2.36 (m, 2H), 2.41-2.11 (m, 2H), 2.01-1.60 (m, 2H), 1.37 (s, 12H); MS (ESI) 325.1 m/z [MH$^+$], C$_{20}$H$_{26}$BO$_3$ requires 325.1.

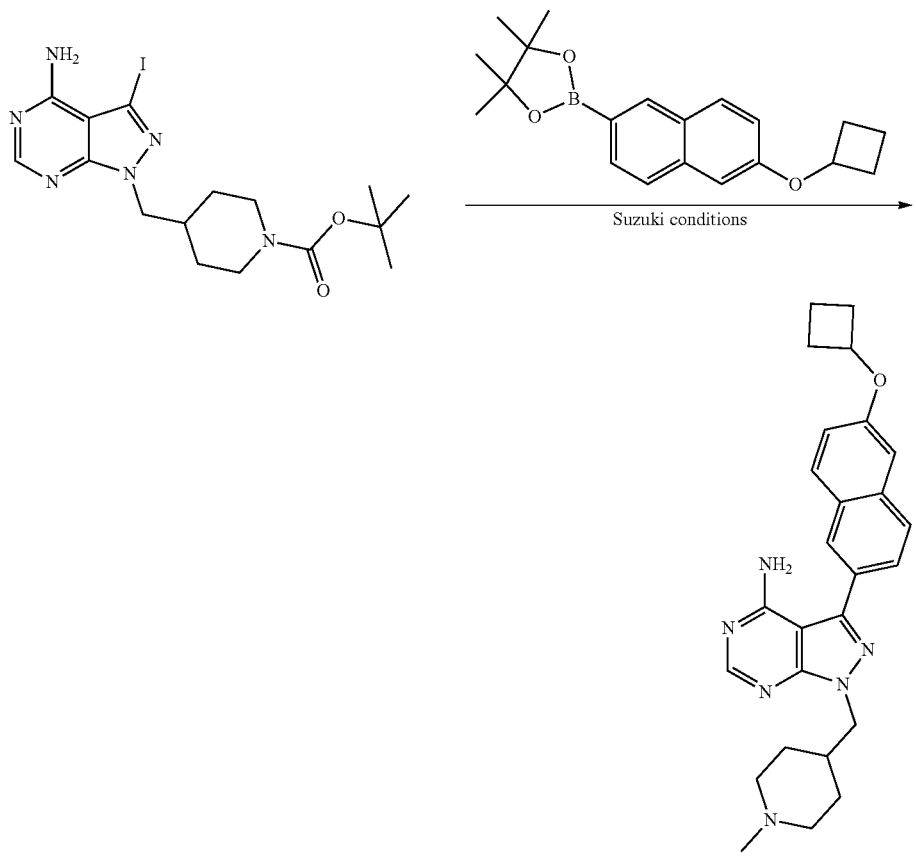

2-(6-Cyclobutoxynaphthalen-2-yl)-4,4,5,5-tetramethyl-1,3,2-dioxaborolane and tert-butyl 4-((4-amino-3-iodo-1H-pyrazolo[3,4-d]pyrimidin-1-yl)methyl)piperidine-1-carboxylate were subjected to the general Suzuki coupling procedure followed by the general boc-deprotection procedure and general reductive amination procedure in order to afford 3-(6-cyclobutoxy-naphthalen-2-yl)-1-((1-methylpiperidin-4-yl)methyl)-1H-pyrazolo[3,4-d]pyrimidin-4-amine.
$^1$H NMR (300 MHz, CD$_3$OD) δ8.47 (s, 1H), 8.15 (s, 1H), 7.99 (d, J=8.3 Hz, 1H), 7.92 (d, J=9.5 Hz, 1H), 7.80 (d, J=8.9 Hz, 1H), 7.24 (m, 2H), 4.53 (d, J=6.6 Hz, 2H), 3.56 (m, 2H), 3.03 (m, 2H), 2.86 (s, 3H), 2.62 (m, 2H), 2.44 (m, 1H), 2.22 (m, 2H), 2.04-1.60 (m, 6H); MS (ESI) 443.4 m/z [MH+], C$_{26}$H$_{31}$N$_6$O requires 443.2.

Example 2: 3-(4-Amino-3-(2-(2,2,2-trifluoroethoxy)quinolin-6-yl)-1H-pyrazolo[3,4-d]pyrimidin-1-yl)-2,2-dimethylpropan-1-ol

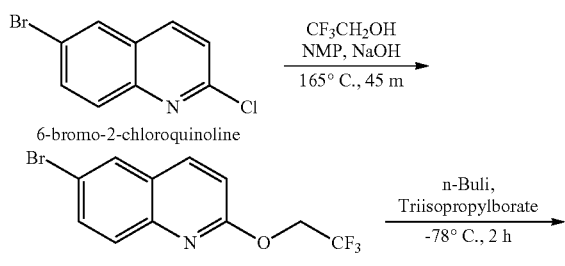

6-bromo-2-chloroquinoline

6-Bromo-2-(2,2,2-trifluoroethoxy)quinolone: 6-bromo-2-chloroquinoline (1.00 g, 4.1 mmol), CF$_3$CH$_2$OH (0.95 mL, 12.3 mmol), N-Methylmorpholine (12 mL), and NaOH (330 mg, 8.2 mmol) were taken in microwave tube and then heated at 165° C. for 45 min. After addition of water, the reaction mixture was extracted with ethyl acetate (3×20 mL). The organic layer was washed with brine, dried over sodium sulfate, and evaporated under reduced pressure. The crude compound was then taken to the next step without further purification.

Synthesis of 2-(2,2,2-Trifluoroethoxy)quinolin-6-ylboronic acid: 6-Bromo-2-(2,2,2-trifluoroethoxy)quinoline was subjected to the general procedure for boronylation using triisopropylborate to afford a white crystalline product (354 mg, 80% yield,). $^1$H NMR (300 MHz, CD$_3$OD) δ6.91 (s, 1H), 6.82 (d, J=8.5 Hz, 1H,), 6.45 (s, 2H) 6.61 (d, J=7.04 Hz, 1H), 3.5 (q, J=8.7 Hz, 2H,); MS (ESI) 272.4 m/z [MH+], C$_{11}$H$_{10}$BF$_3$NO$_3$ requires 272.2.

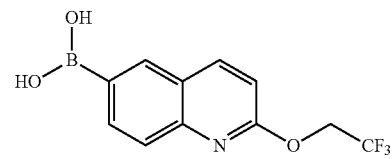

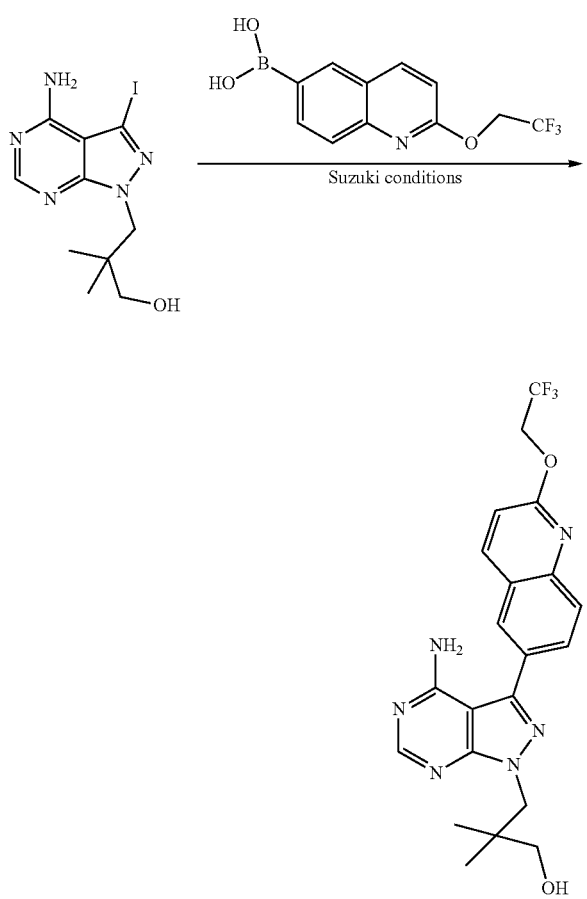 [SMILES: CC(C)(CO)Cn1nc(I)c2c(N)ncnc21 ; OB(O)c1ccc2nc(OCC(F)(F)F)ccc2c1 ; CC(C)(CO)Cn1nc(-c2ccc3nc(OCC(F)(F)F)ccc3c2)c2c(N)ncnc21]

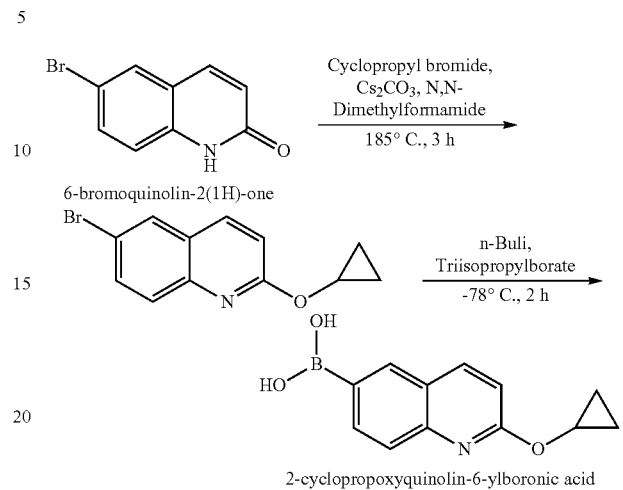

2-cyclopropoxyquinolin-6-ylboronic acid 2-(2,2,2-Trifluoroethoxy)quinolin-6-ylboronic acid and 3-(4-amino-3-iodo-1H-pyrazolo-[3,4-d]pyrimidin-1-yl)-2,2-dimethylpropan-1-ol were subjected to the general Suzuki coupling procedure in order to afford 3-(4-Amino-3-(2-(2,2,2-trifluoroethoxy)quinolin-6-yl)-1H-pyrazolo[3,4-d]pyrimidin-1-yl)-2,2-dimethylpropan-1-ol. $^1$H NMR (300 MHz, CD$_3$OD) δ8.40 (s, 1H), 8.17 (d, J=8.7 Hz, 1H), 8.07 (d, J=1.6 Hz, 1H), 8.01-7.95 (m, 2H), 7.12 (d, J=8.9 Hz, 1H), 4.98 (q, J=8.5 Hz, 2H), 4.35 (s, 2H), 3.15 (s, 2H), 1.05 (s, 6H); MS (ESI) 447.5 m/z [MH+], C$_{21}$H$_{21}$F$_3$N$_6$O$_2$ requires 447.4.

Example 3: 3-(2-Cyclopropoxyquinolin-6-yl)-4-((1-methylpiperidin-4-yl)methyl)-1H-pyrazolo[3,4-d]pyrimidin-4-amine 6-Bromo-2-cyclopropoxyquinoline: 6-Bromo-quinolin-2(1H)-one (1.00 g, 4.4 mmol, 1 equiv.), Cs$_2$CO$_3$ (5.08 g, 17.8 mmol), and bromocyclopropane (1.06 g, 13.3 mmol) in dry DMF (10 mL) were heated at 180° C. in a microwave for 3 h. After completion, ethyl acetate and water were added and the organic phase was separated. The water phase was further extracted with ethyl acetate. The combined organic phases were washed with brine, dried over Na$_2$SO$_4$ and evaporated under reduced pressure. The crude product was then purified via flash chromatography over silica, eluting with a hexanes/EtOAc solvent gradient to afford 0.235 mg (20% yield) of pure product. $^1$H NMR (300 MHz, CDCl$_3$) δ7.89 (s, 1H), 7.87-7.82 (m, 1H), 7.78-7.65 (m, 2H), 6.88 (d, J=8.91 Hz, 1H), 4.54-4.44 (m, 1H), 0.94-0.77 (m, 4H); MS (ESI) 265.5 m/z [MH+], C$_{12}$H$_{11}$BrNO requires 265.2.

2-Cyclopropoxyquinolin-6-ylboronic acid: 6-Bromo-2-cyclopropoxyquinoline (2.01 g, 7.95 mmol, 1 equiv.) and triisopropylborate (2.05 mg, 13.5 mmol, 1.69 equiv.) were subjected to general procedure for boronylation using triisopropylborate to afford the desired pure product (1.05 g, 80% yield); $^1$H NMR (300 MHz, DMSO) δ8.37-8.28 (m, 2H), 8.10-8.04 (m, 1H), 7.77 (d, J=8.5 Hz, 1H), 7.06 (d, J=8.9 Hz, 1H), 4.55-4.45 (m, 1H), 0.91-0.81 (m, 2H), 0.80-0.73 (m, 2H); MS (ESI) 230.2 m/z [MH+], C$_{12}$H$_{13}$BNO$_3$ requires 230.2.

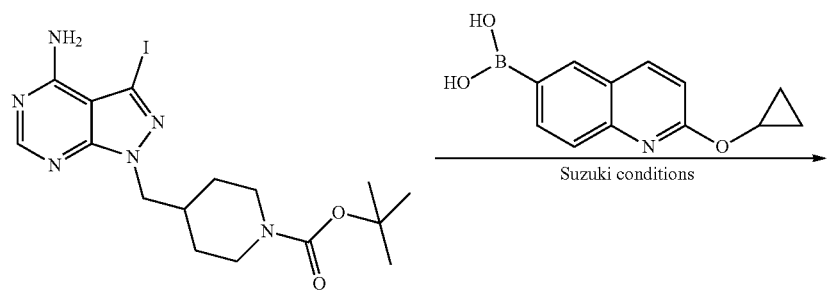

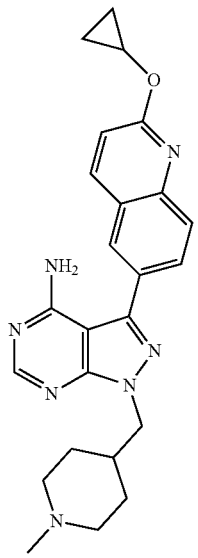

2-Cyclopropoxyquinolin-6-ylboronic acid and tert-butyl 4-((4-amino-3-iodo-1H-pyrazolo[3,4-d]pyrimidin-1-yl)methyl)piperidine-1-carboxylate were subjected to the general Suzuki coupling procedure followed by the general boc-deprotection procedure and general reductive amination procedure in order to afford 3-(2-cyclopropoxyquinolin-6-yl)-14(1-methylpiperidin-4-yl)methyl)-1H-pyrazolo[3,4-d]pyrimidin-4-amine. $^1$H NMR (300 MHz, CD$_3$OD) δ9.17 (s, 1H), 8.75-8.33 (m, 3H), 8.28-7.98 (m, 2H), 4.72 (m, 1H), 4.54 (d, J=6.0 Hz, 2H), 3.56 (m, 2H), 3.10 (m, 2H), 3.00 (s, 3H), 2.48 (m, 1H), 2.00 (m, 2H), 1.60 (m, 2H), 1.20-1.10 (m, 4H); MS (ESI) 430.5 m/z [MH+], C$_{24}$H$_{28}$N$_7$O requires 430.6.

Example 4: 3-(6-Cyclopropoxynaphthalen-2-yl)-1-((1-methylpiperidin-4-yl)methyl)-1H-pyrazolo[3,4-d]pyrimidin-4-amine

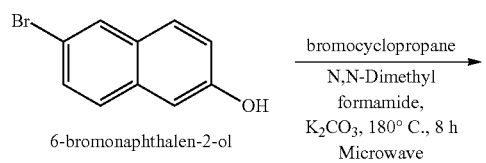

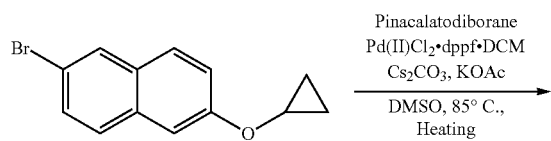

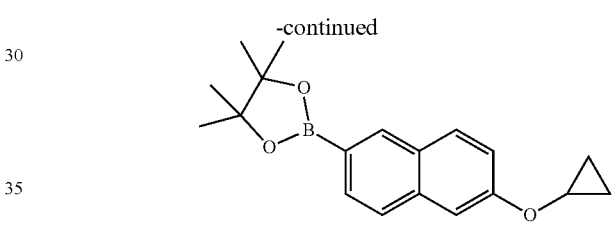

2-Bromo-6-cyclopropoxynaphthalene: 6-Bromonaphthalen-2-ol (3.00 g, 13.0 mmol), Cs$_2$CO$_3$ (1.29 g, 39.6 mmol) and bromocyclopropane (4.07 g, 39.0 mmol) were taken in a microwave tube and heated at 180° C. for 30 min. After completion, ethyl acetate and water were added and the organic phase was separated. The water phase was further extracted with ethyl acetate. The combined organic phases were washed with brine, dried over Na$_2$SO$_4$ and evaporated under reduced pressure. The crude product was then purified via flash chromatography over silica, eluting with a hexanes/EtOAc solvent gradient to afford 2.50 g (71% yield) of pure product. $^1$H NMR (300 MHz, CDCl$_3$): δ ppm 7.91 (m, 1H), 7.66-7.58 (dd, J=8.9, 4.6 Hz, 2H), 7.53-7.46 (dd, J=8.7, 1.9 Hz, 1H), 7.39 (d, J=2.1 Hz, 1H), 7.18-7.12 (dd, J=8.9, 2.3 Hz, 1H), 3.83 (m, 1H), 0.87-0.78 (m, 4H); MS (ESI): 264.2 m/z [MH+], C$_{13}$H$_{12}$BrO requires 264.2.

2-(6-Cyclopropoxynaphthalen-2-yl)-4,4,5,5-tetramethyl-1,3,2-dioxaborolane: 2-Bromo-6-cyclopropoxynaphthalene was subjected to the general pinacol ester formation procedure to afford 1.01 g, (65% yield) of a white crystalline product. $^1$H NMR (300 MHz, CDCl$_3$): δ ppm 8.27 (s, 1H), 7.77 (m, 3H) 7.45 (d, J=2.3 Hz, 1H), 7.14 (dd, J=8.9, 2.48 Hz, 1H), 3.88 (m, 1H), 1.40 (s, 12H), 0.87 (m, 2H), 0.82 (m, 2H); MS (ESI): 311.5 m/z [MH+], C$_{19}$H$_{24}$BO$_3$ requires 311.2.

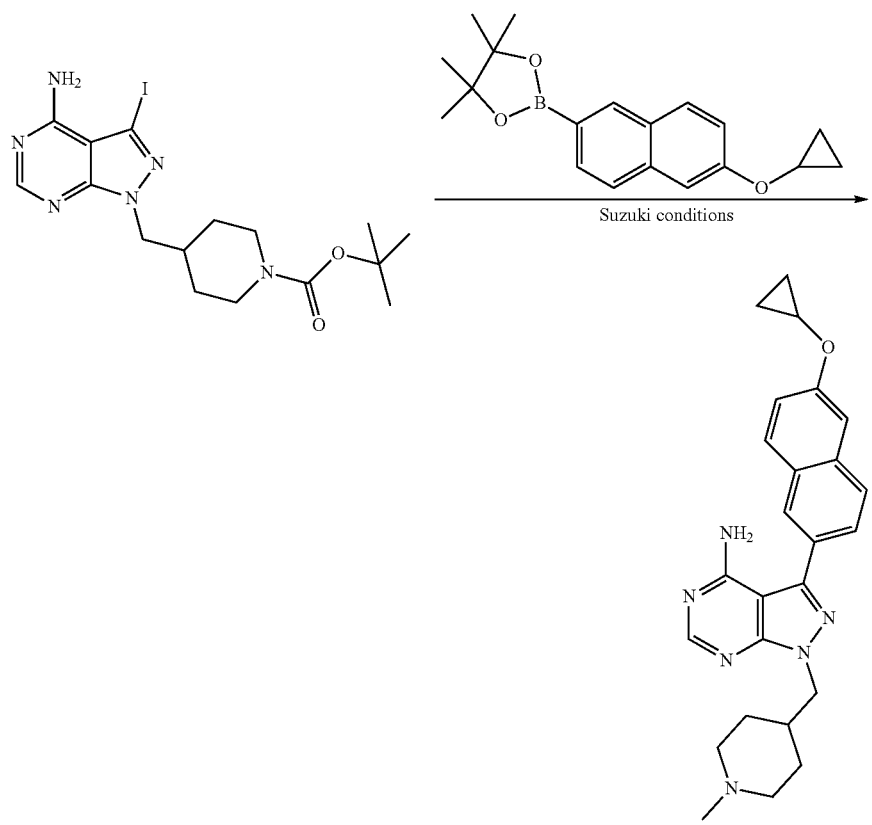

2-(6-Cyclopropoxynaphthalen-2-yl)-4,4,5,5-tetramethyl-1,3,2-dioxaborolane and tert-butyl 4-((4-amino-3-iodo-1H-pyrazolo[3,4-d]pyrimidin-1-yl)methyl)piperidine-1-carboxylate were subjected to the general Suzuki coupling procedure followed by the general boc-deprotection procedure and general reductive amination procedure in order to afford 3-(6-cyclopropoxynaphthalen-2-yl)-1-((1-methylpiperidin-4-yl)methyl)-1H-pyrazolo[3,4-d]pyrimidin-4-amine. $^1$H NMR (300 MHz, CD$_3$OD) δ8.49 (s, 1H), 8.17 (s, 1H), 8.03 (d, J=8.5 Hz, 1H), 7.92 (d, J=9.1 Hz, 1H), 7.80 (d, J=8.5 Hz, 1H), 7.64 (d, J=2.0 Hz, 1H), 7.27 (dd, J=8.9, 1.8 Hz, 1H), 4.52 (d, J=6.0 Hz, 2H), 3.98 (m, 1H), 3.56 (m, 2H), 3.05 (m, 2H), 2.87 (s, 3H), 2.44 (m, 1H), 2.00 (m, 2H), 1.76 (m, 2H), 0.92 (m, 2H), 0.80 (m, 2H); MS (ESI) 429.5 m/z [MH+], C$_{25}$H$_{29}$N$_6$O requires 429.6.

Example 5: 3-(2-Cyclopropoxyquinolin-6-yl)-1-(3-(dimethylamino)-2,2-dimethylpropyl)-1H-pyrazolo[3,4-d]pyrimidin-4-amine

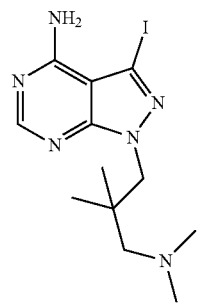

1-(3-(Dimethylamino)-2,2-dimethylpropyl)-3-iodo-1H-pyrazolo[3,4-d]pyrimidin-4-amine was generated with 3-iodo-1H-pyrazolo[3,4-d]pyrimidin-4-amine and 3-bromo-N,N,2,2-tetramethylpropan-1-amine using the general R$_2$ alkylation procedure, to afford the product as pale yellow solid, (286 mg, 40% yield); $^1$H NMR (300 MHz, MeOD4) δ 8.38 (s, 1H), 4.46 (s, 2H), 3.22 (s, 2H), 3.06 (s, 6H), 1.16 (s, 6H); MS (ESI) 375.2 [MH+], C$_{12}$H$_{20}$IN$_6$ requires 375.2.

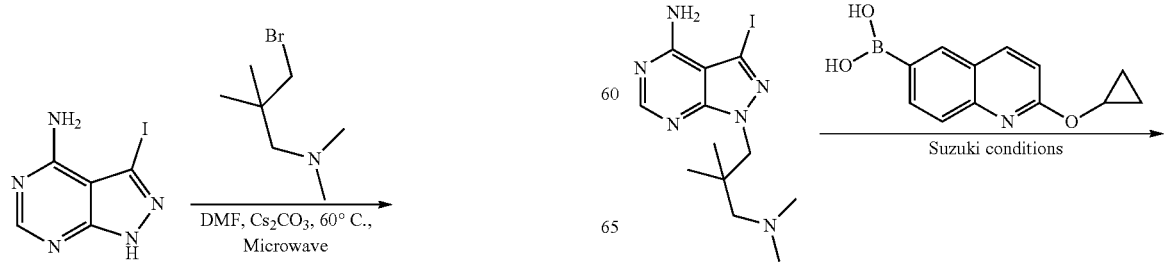

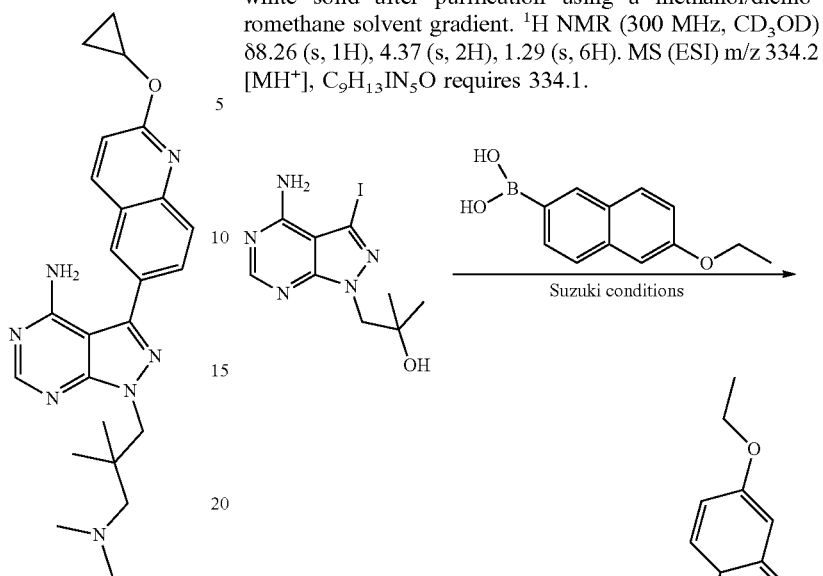

2-Cyclopropoxyquinolin-6-ylboronic acid and 1-(3-(dimethylamino)-2,2-dimethylpropyl)-3-iodo-1H-pyrazolo[3,4-d]pyrimidin-4-amine were subjected to the general Suzuki coupling procedure to afford 3-(2-cyclopropoxyquinolin-6-yl)-1-(3-(dimethylamino)-2,2-dimethylpropyl)-1H-pyrazolo[3,4-d]pyrimidin-4-amine. $^1$H NMR (300 MHz, CD$_3$OD) δ8.29 (s, 1H), 8.22 (d, J=8.9 Hz, 1H,), 8.11 (d, J=1.6 Hz, 1H) 8.01 (s, 1H), 8.00 (dd, J=8.5, 1.5 Hz, 1H,), 7.07 (d, J=8.9 Hz, 1H), 4.46 (m, 1H), 4.36 (s, 2H), 2.46 (s, 2H), 2.44 (s, 6H), 1.03 (s, 6H), 0.93-0.82 (m, 4H). MS (ESI) 432.6 m/z [MH+], C$_{24}$H$_{30}$N$_7$O requires 432.5.

Example 6: 1-(4-amino-3-(6-ethoxynaphthalen-2-yl)-1H-pyrazolo[3,4-d]pyrimidin-1-yl)-2-methylpropan-2-ol

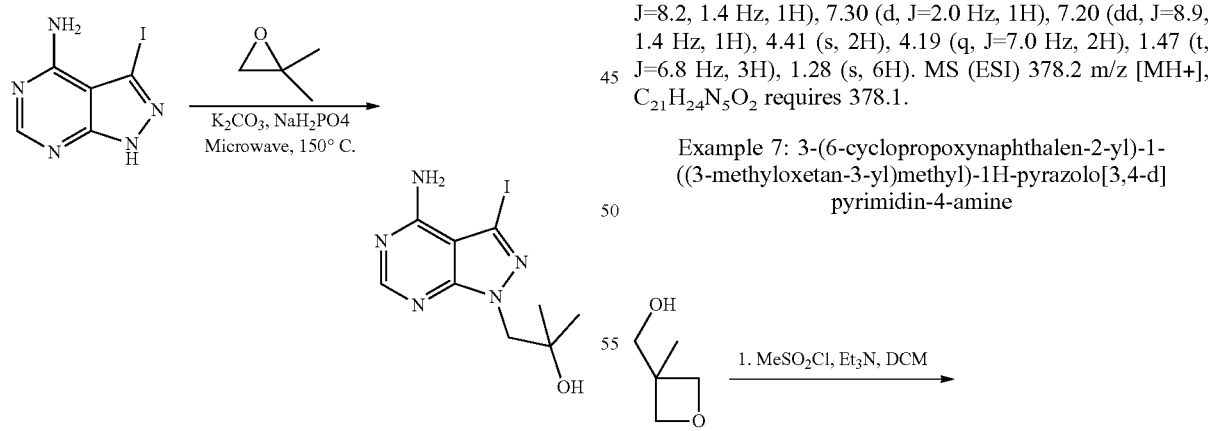

1-(4-Amino-3-iodo-1H-pyrazolo[3,4-d]pyrimidin-1-yl)-2-methylpropan-2-ol was generating using the general R$_2$ alkylation procedure using 3-iodo-1H-pyrazolo[3,4-d]pyrimidin-4-amine (500 mg, 1.92 mmol), 2,2-dimethyloxirane (0.276 mg, 3.80 mmol), and K$_2$CO$_3$:NaH$_2$PO$_4$ (0.262 mg, 1.90 mmol) in 3 mL of a acetonitrile:water (8.5:1.5) mixture. The reaction was stirred at 150° C. for 3 h in a microwave, affording 1-(4-amino-3-iodo-1H-pyrazolo[3,4-d]pyrimidin-1-yl)-2-methylpropan-2-ol (150 mg, yield, 23.4% yield) as a white solid after purification using a methanol/dichloromethane solvent gradient. $^1$H NMR (300 MHz, CD$_3$OD) δ8.26 (s, 1H), 4.37 (s, 2H), 1.29 (s, 6H). MS (ESI) m/z 334.2 [MH+], C$_9$H$_{13}$IN$_5$O requires 334.1.

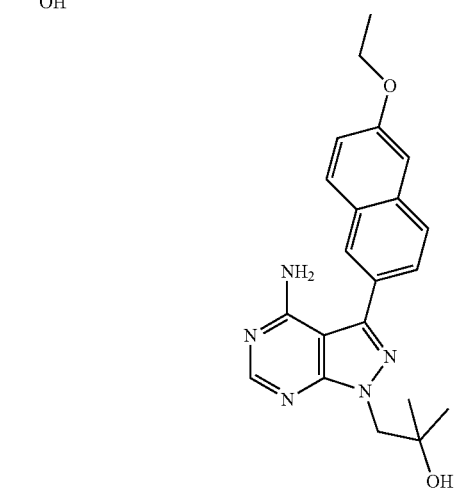

6-ethoxynaphthalen-2-ylboronic acid and 1-(4-amino-3-iodo-1H-pyrazolo[3,4-d]pyrimidin-1-yl)-2-methylpropan-2-ol were subjected to the general Suzuki coupling procedure to afford compound 1-(4-amino-3-(6-ethoxynaphthalen-2-yl)-1H-pyrazolo[3,4-d]pyrimidin-1-yl)-2-methylpropan-2-ol; $^1$H NMR (300 MHz, CD$_3$OD) δ8.26 (s, 1H), 8.09 (s, 1H), 7.97-7.83 (m, 2H), 7.76 (dd, J=8.2, 1.4 Hz, 1H), 7.30 (d, J=2.0 Hz, 1H), 7.20 (dd, J=8.9, 1.4 Hz, 1H), 4.41 (s, 2H), 4.19 (q, J=7.0 Hz, 2H), 1.47 (t, J=6.8 Hz, 3H), 1.28 (s, 6H). MS (ESI) 378.2 m/z [MH+], C$_{21}$H$_{24}$N$_5$O$_2$ requires 378.1.

Example 7: 3-(6-cyclopropoxynaphthalen-2-yl)-1-((3-methyloxetan-3-yl)methyl)-1H-pyrazolo[3,4-d]pyrimidin-4-amine

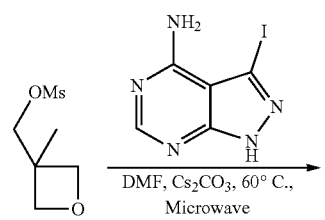
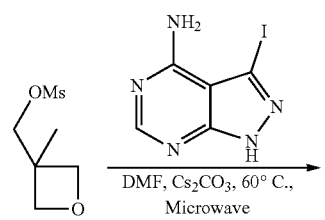

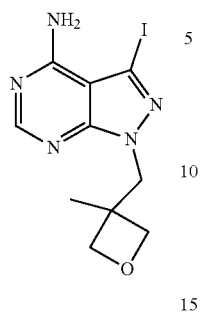

Methanesulfonyl chloride (7.54 mL, 97.9 mmol) was added slowly at 0° C. to a solution of (3-methyloxetan-3-yl)methanol (5.00 mg, 48.9 mmol) and triethylamine (13 mL, 97 mmol) in dichloromethane (20 mL). The reaction was stirred for 5 h at room temperature. After completion of the reaction, dichloromethane was removed by reduced pressure and the reaction was diluted with ethyl acetate. The ethyl acetate was washed with NaHCO₃ (25 mL), 1N HCl, brine (50 mL), dried over sodium sulfate, and concentrated. The crude product was subjected to flash chromatography using a hexane/ethyl acetate solvent gradient to afford pure 3-methyloxetan-3-yl)methyl methanesulfonate (4.40 g, 50% yield). $^1$H NMR (301 MHz, CDCl₃) δ4.70-4.12 (m, 6H), 3.07 (s, 3H), 1.39 (s, 3H); MS (ESI) 181.1 [MH+], C₆H₁₃O₄S requires 181.0.

3-Iodo-1-((3-methyloxetan-3-yl)methyl)-1H-pyrazolo[3,4-d]pyrimidin-4-amine was generated by subjecting 3-iodo-1H-pyrazolo[3,4-d]pyrimidin-4-amine (150 mg, 0.60 mmol) and (3-methyloxetan-3-yl)methyl methanesulfonate (83 mg, 0.46 mmol) to the general R₂ alkylation procedure (110 mg, 55% yield). $^1$H NMR (300 MHz, CDCl₃) δ8.33 (s, 1H), 5.94 (s, 2H), 4.79 (d, J=6.4 Hz, 2H), 4.56 (s, 2H), 4.41 (d, J=6.1 Hz, 2H), 1.28 (s, 3H); MS (ESI) m/z 346.2 [MH⁺], C₁₀H₁₃IN₅O requires 346.1.

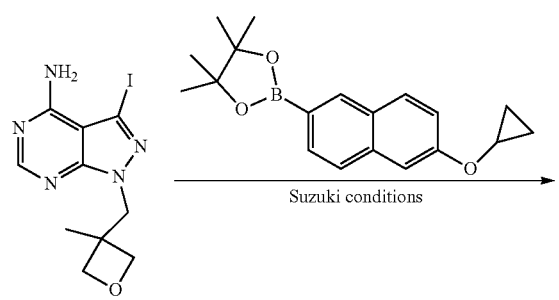

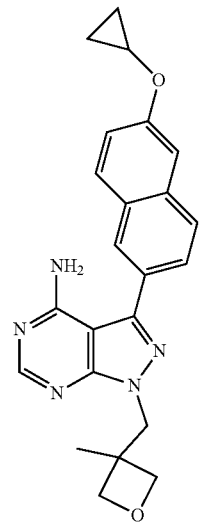

2-(6-cyclopropoxynaphthalen-2-yl)-4,4,5,5-tetramethyl-1,3,2-dioxaborolane and 3-iodo-1-((3-methyloxetan-3-yl)methyl)-1H-pyrazolo[3,4-d]pyrimidin-4-amine were subjected to the general Suzuki coupling procedure in order to afford 3-(6-cyclopropoxynaphthalen-2-yl)-1-((3-methyloxetan-3-yl)methyl)-1H-pyrazolo[3,4-d]pyrimidin-4-amine. $^1$H NMR (300 MHz, CDCl₃) δ8.39 (s, 1H), 8.08 (s, 1H), 7.93 (d, J=8.7 Hz, 1H), 7.83 (d, J=8.9 Hz, 1H), 7.77 (d, J=9.4 Hz, 1H), 7.52 (s, 1H), 7.24 (dd, J=10.0, 3.0 Hz, 1H), 5.68 (s, 2H), 4.90 (d, J=6.1 Hz, 2H), 4.64 (s, 2H), 4.45 (d, J=6.1 Hz, 2H), 3.91 (m, 1H), 1.36 (3, 3H), 0.96-0.83 (m, 4H); MS (ESI) 402.2 m/z [MH+], C₂₃H₂₄N₅O₂ requires 402.4.

Example 8: 2-((4-Amino-3-(6-cyclopropoxynaphthalen-2-yl)-1H-pyrazolo[3,4-d]pyrimidin-1-yl)methyl)-1,1,1,3,3,3-hexafluoropropan-2-ol

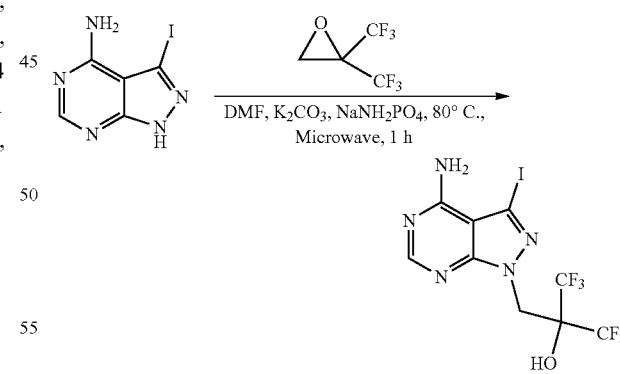

2-((4-Amino-3-iodo-1H-pyrazolo[3,4-d]pyrimidin-1-yl)methyl)-1,1,1,3,3,3-hexafluoropropan-2-ol was generated by subjecting 3-iodo-1H-pyrazolo[3,4-d]pyrimidin-4-amine (250 mg, 0.96 mmol), 2,2-bis(trifluoromethyl)oxirane (0.17 mL, 1.44 mmol), and K₂CO₃:NaH₂PO₄ (198 mg, 1.44 mmol) to the general R₂ alkylation procedure (126 mg, 30% yield). $^1$H-NMR (301 MHz, CDCl₃) δ8.33 (s, 1H), 8.02 (s, 1H), 6.33 (s, 2H); MS (ESI) m/z 442.1 [MH⁺], C₉H₆F₆IN₅O requires 442.2.

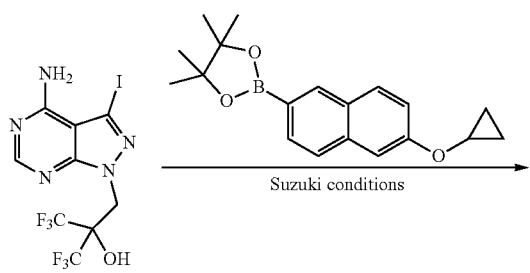

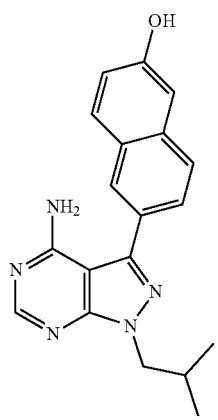

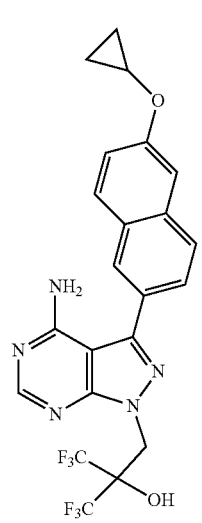

2-(6-Cyclopropoxynaphthalen-2-yl)-4,4,5,5-tetramethyl-1,3,2-dioxaborolane and 2-((4-amino-3-iodo-1H-pyrazolo[3,4-d]pyrimidin-1-yl)methyl)-1,1,1,3,3,3-hexafluoropropan-2-ol were subjected to the general Suzuki coupling procedure in order to afford 2-((4-amino-3-(6-cyclopropoxynaphthalen-2-yl)-1H-pyrazolo[3,4-d]pyrimidin-1-yl)methyl)-1,1,1,3,3,3-hexafluoropropan-2-ol. $^1$H NMR (300 MHz, CD$_3$OD) δ8.32 (s, 1H), 8.11 (s, 1H), 7.97 (d, J=8.5 Hz, 1H), 7.87 (d, J=9.1 Hz, 1H), 7.76 (dd, J=8.5, 1.6 Hz, 1H), 7.59 (d, 1H), 7.23 (dd, J=8.9, 2.2 Hz, 1H), 5.03 (s, 2H), 3.94 (m, 1H), 0.94-0.76 (m, 4H); MS (ESI) 498.2 m/z [MH+], C$_{22}$H$_{18}$F$_6$N$_5$O$_2$ requires 498.2.

Example 9: 3-(6-cyclopropoxynaphthalen-2-yl)-1-isobutyl-1H-pyrazolo[3,4-d]pyrimidin-4-amine

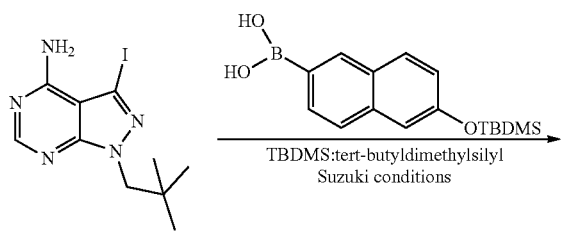

6-tert-butyldimethylsilyloxy-2-naphthaleneboronic acid and 3-iodo-1-isobutyl-1H-pyrazolo[3,4-d]pyrimidin-4-amine[2] were subjected to the general Suzuki coupling procedure. The crude product was purified by silica gel using dichloromethane/methanol gradient (note: deprotection of the tert-butyldimethylsilyloxy protecting group was observed after purification). $^1$H NMR (300 MHz, CD$_3$OD) δ8.27 (s, 1H), 8.03 (s, 1H), 7.82 (m, 2H), 7.71 (m, 1H), 7.18 (m, 2H), 4.21 (d, J=4.2 Hz, 2H), 2.39 (m, 1H), 0.96 (d, J=6.5 Hz, 6H); MS (ESI) 334.4 m/z [MH+], C$_{19}$H$_{19}$N$_5$O requires 334.2.

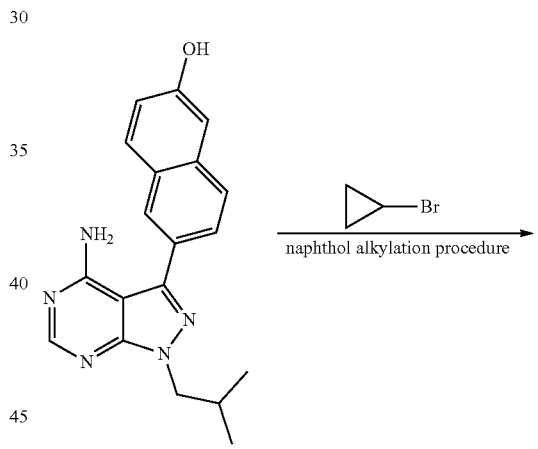

6-(4-amino-1-isobutyl-1H-pyrazolo[3,4-d]pyrimidin-3-yl)naphthalen-2-ol and bromocyclopropane were subjected to the general naphthol alkylation procedure in order to afford 3-(6-cyclopropoxynaphthalen-2-yl)-1-isobutyl-1H-pyrazolo[3,4-d]pyrimidin-4-amine. ¹H NMR (300 MHz, CD₃OD) δ8.27 (s, 1H), 8.10 (s, 1H), 7.98 (d, J=8.7 Hz, 1H), 7.89 (d, J=8.9 Hz, 1H), 7.76 (dd, J=8.5, 1.6 Hz, 1H), 7.61 (d, J=2.2 Hz, 1H), 7.25-7.18 (dd, J=8.9, 2.2 Hz, 1H), 4.24 (d, J=7.25 Hz, 2H), 3.95 (m, 1H), 2.38 (m, 1H), 0.97 (d, J=6.6 Hz, 6H), 0.90 (m, 2H), 0.79 (m, 2H); MS (ESI) 374.2 m/z [MH+], C₂₂H₂₄N₅O requires 374.4.

Example 10: 3-(6-(Cyclopropylmethoxy)naphthalen-2-yl)-1-((1-methylpiperidin-4-ylmethyl)-1H-pyrazolo[3,4-d]pyrimidin-4-amine

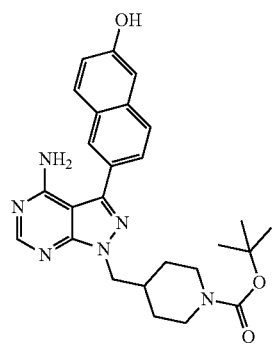

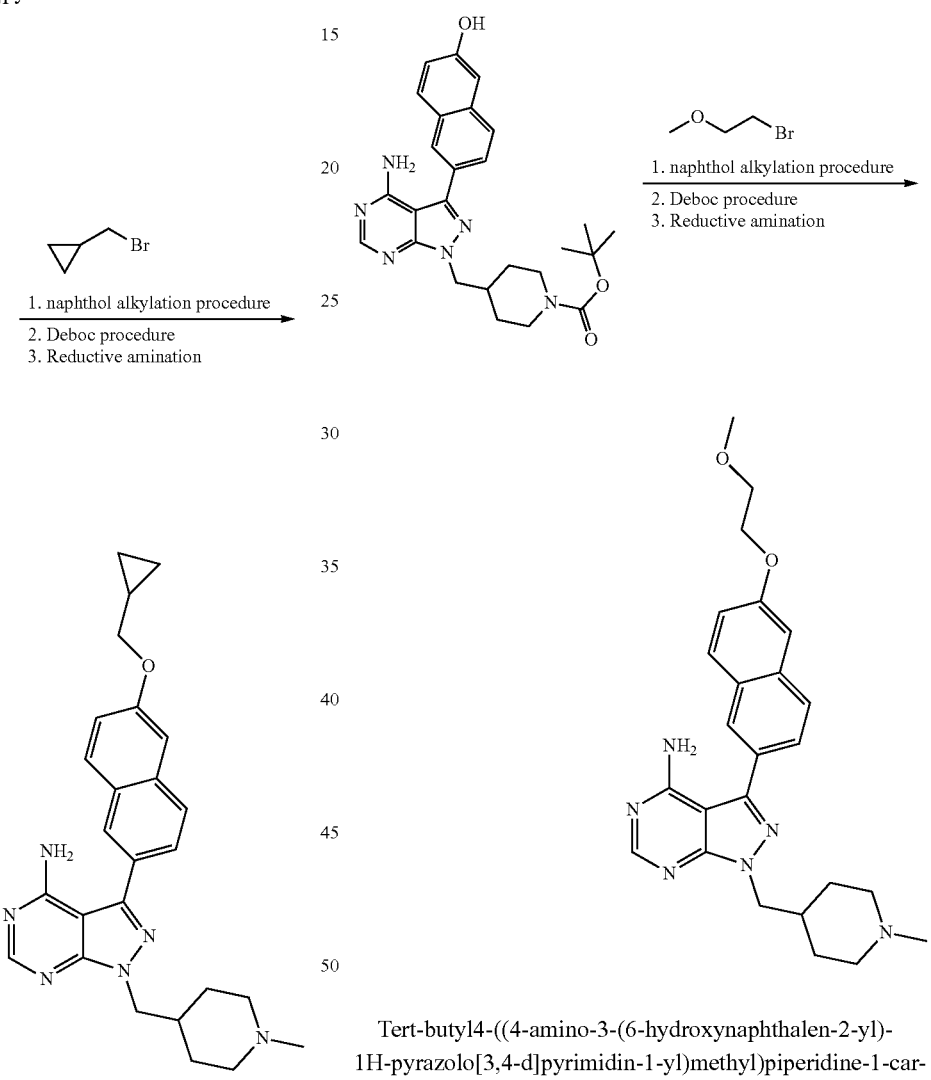

Tert-butyl4-((4-amino-3-(6-hydroxynaphthalen-2-yl)-1H-pyrazolo[3,4-d]pyrimidin-1-yl)methyl)piperidine-1-carboxylate and (bromomethyl)cyclopropane were subjected to the general naphthol alkylation procedure followed by the general boc-deprotection procedure and general reductive amination procedure in order to afford the product. ¹H NMR (300 MHz, CD₃OD) δ8.51 (s, 1H), 8.17 (s, 1H), 8.01 (d, J=8.5 Hz, 1H), 7.93 (d, J=9.1 Hz, 1H), 7.81 (d, J=9.3 Hz, 1H), 7.36 (s, 1H), 7.30 (d, J=9.3 Hz, 1H), 4.56 (d, J=6.4 Hz, 2H), 4.03 (d, J=6.6 Hz, 2H), 3.57 (m, 2H), 3.06 (m, 2H), 2.88 (s, 3H), 2.45 (m, 1H), 2.02 (m, 2H), 1.77 (m, 2H), 1.44 (m, 1H), 0.71 (m, 2H), 0.46 (m, 2H); MS (ESI) 443.5 m/z [MH+], C₂₆H₃₁N₆O requires 443.5.

Example 11: 3-(6-(2-Methoxyethoxy)naphthalen-2-yl)-1-((1-methylpiperidin-4-yl)methyl)-1H-pyrazolo[3,4-d]pyrimidin-4-amine Tert-butyl4-((4-amino-3-(6-hydroxynaphthalen-2-yl)-1H-pyrazolo[3,4-d]pyrimidin-1-yl)methyl)piperidine-1-carboxylate and bromomethoxyethane were subjected to the general naphthol alkylation procedure followed by the general boc-deprotection procedure and general reductive amination procedure in order to afford the product. ¹H NMR (300 MHz, CD₃OD) δ8.50 (s, 1H), 8.16 (s, 1H), 8.01 (d, J=7.8 Hz, 1H), 7.93 (d, J=8.5 Hz, 1H), 7.80 (d, J=8.3 Hz, 1H), 7.40 (s, 1H), 7.30 (d, J=7.8 Hz, 1H), 4.52 (d, J=4.2 Hz, 2H), 4.31 (m, 2H), 3.86 (m, 2H), 3.62 (m, 2H), 3.54 (s, 3H), 3.04 (m, 2H), 2.87 (s, 3H), 2.44 (m, 1H), 1.99 (m, 2H), 1.77 (m, 2H); MS (ESI) 447.5 m/z [MH+], C₂₅H₃₁N₆O₂ requires 447.5.

Example 12: 1-((1-Methylpiperidin-4-yl)methyl)-3-(6-(oxetan-3-yloxy)naphthalen-2-yl)-1H-pyrazolo[3,4-(1]pyrimidin-4-amine

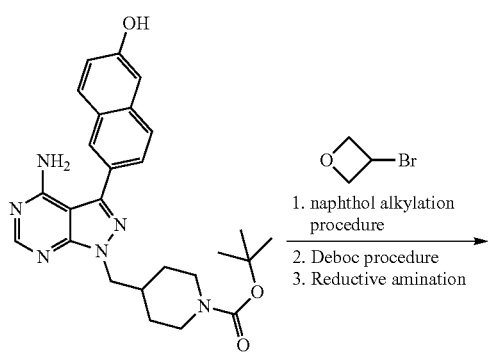

Example 13: 2-(6-(4-Amino-1-((1-methylpiperidin-4-yl)methyl)-1H-pyrazolo[3,4-d]pyrimidin-3-yl)naphthalen-2-yloxy)ethanol

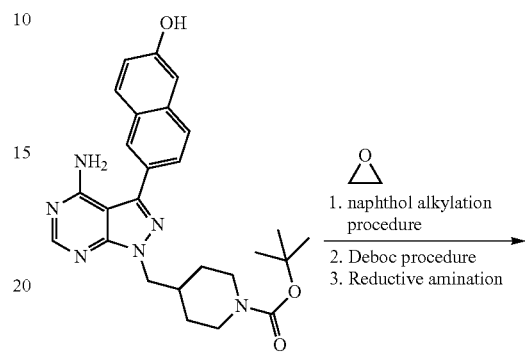

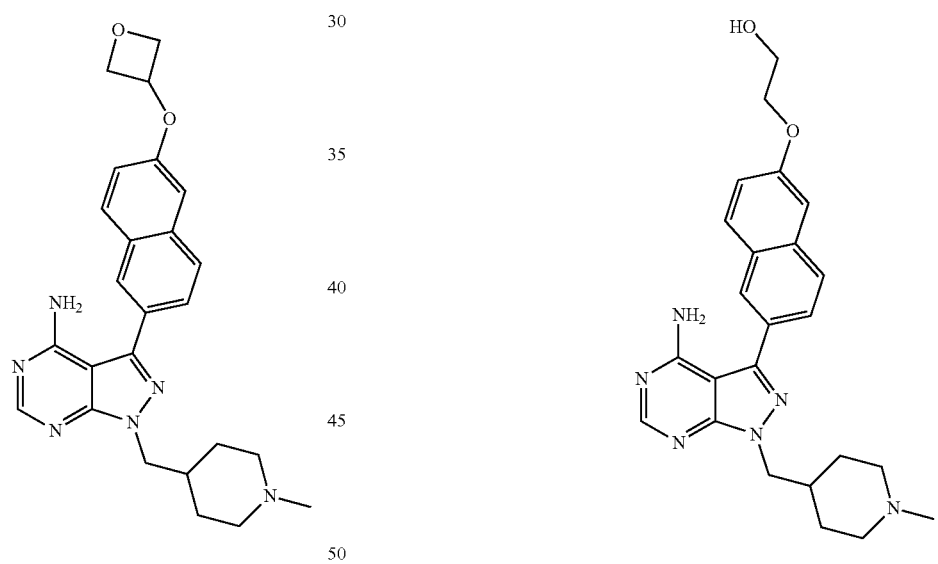

Tert-butyl4-((4-amino-3-(6-hydroxynaphthalen-2-yl)-1H-pyrazolo[3,4-d]pyrimidin-1-yl)methyl)piperidine-1-carboxylate and 3-bromooxetane were subjected to the general naphthol alkylation procedure followed by the general boc-deprotection procedure and general reductive amination procedure in order to afford the product. $^1$H NMR (300 MHz, CD$_3$OD) δ8.49 (s, 1H), 8.18 (s, 1H), 8.06-7.92 (m, 2H), 7.82 (d, J=8.5 Hz, 1H), 7.51 (s, 1H), 7.36 (d, J=9.1 Hz, 1H), 4.81 (m, 1H), 4.53 (d, J=5.6 Hz, 2H), 3.99-3.84 (m, 4H), 3.57 (m, 2H), 3.05 (m, 2H), 2.86 (s, 3H), 2.44 (m, 1H), 2.00 (m, 2H), 1.74 (m, 2H); MS (ESI) 445.2 m/z [MH+], C$_{25}$H$_{29}$N$_6$O$_2$ requires 445.2.

Tert-butyl4-((4-amino-3-(6-hydroxynaphthalen-2-yl)-1H-pyrazolo[3,4-d]pyrimidin-1-yl)methyl)piperidine-1-carboxylate and oxirane were subjected to the general naphthol alkylation procedure followed by the general boc-deprotection procedure and general reductive amination procedure in order to afford the product. $^1$H NMR (300 MHz, CD$_3$OD) δ8.50 (s, 1H), 8.17 (s, 1H), 8.02 (d, J=8.3 Hz, 1H), 7.94 (d, J=8.9 Hz, 1H), 7.80 (d, J=8.9 Hz, 1H), 7.41 (d, J=2.2 Hz, 1H), 7.34 (dd, J=8.7, 2.0 Hz, 1H), 4.53 (d, J=6.4 Hz, 2H), 4.25 (t, J=4.5 Hz, 2H), 3.99 (t, J=4.5 Hz, 2H), 3.56 (m, 2H), 3.04 (m, 2H), 2.86 (s, 3H), 2.44 (m, 1H), 2.00 (m, 2H), 1.72 (m, 2H); MS (ESI) 433.3 m/z [MH+], C$_{24}$H$_{29}$N$_6$O$_2$ requires 433.5.

Example 14: 1-(6-(4-Amino-1-((1-methylpiperidin-4-yl)methyl)-1H-pyrazolo[3,4-d]pyrimidin-3-yl)naphthalen-2-yloxy)-2-methylpropan-2-ol

Example 15: 3-(2-Ethoxyquinolin-6-yl)-14(1-methylpiperidin-4-yl)methyl)-1H-pyrazolo[3,4-d]pyrimidin-4-amine

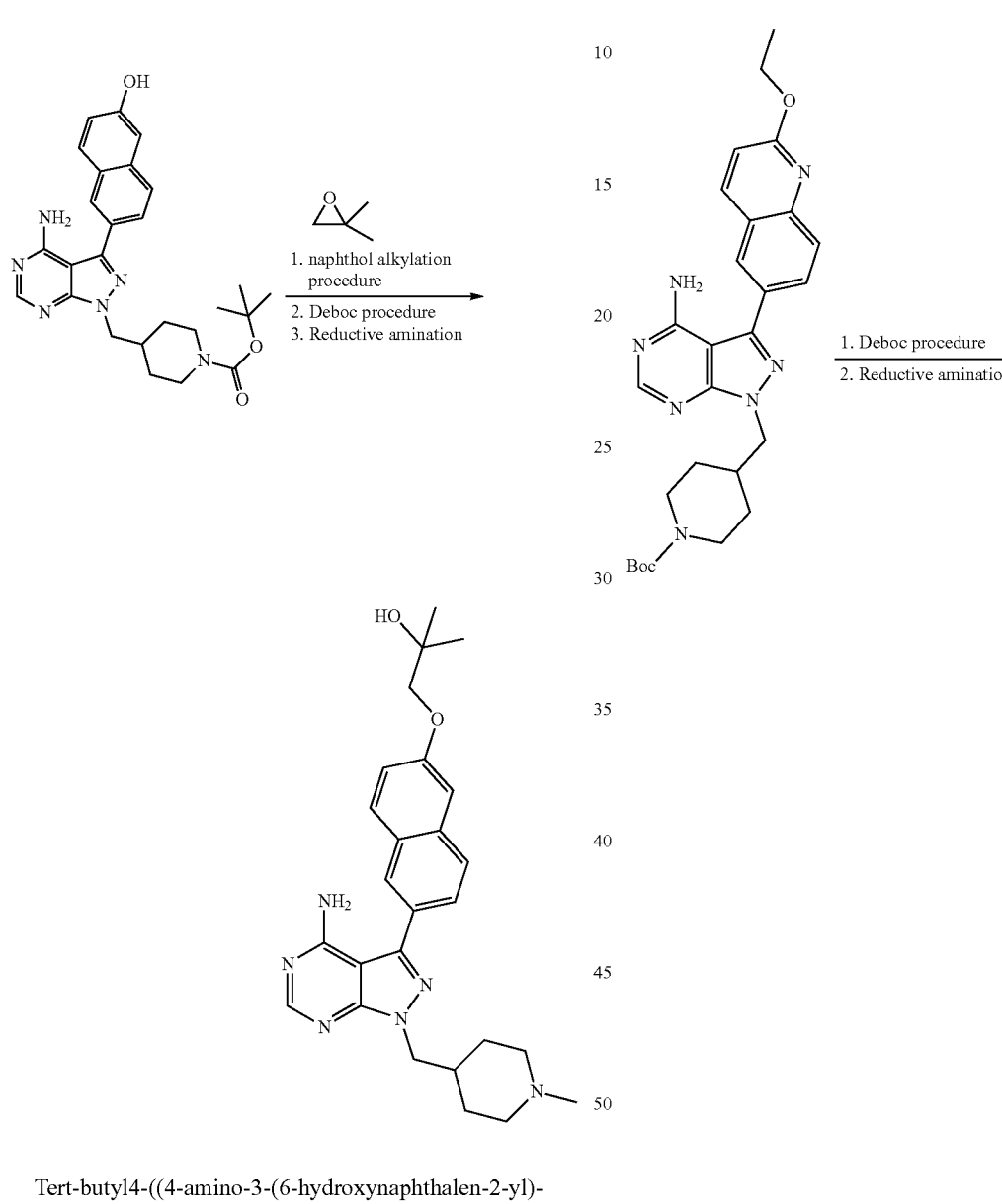

Tert-butyl4-((4-amino-3-(6-hydroxynaphthalen-2-yl)-1H-pyrazolo[3,4-d]pyrimidin-1-yl)methyl)piperidine-1-carboxylate and 2,2-dimethyloxirane were subjected to the general naphthol alkylation procedure followed by the general boc-deprotection procedure and general reductive amination procedure in order to afford the product. $^1$H NMR (300 MHz, CD$_3$OD) δ8.48 (s, 1H), 8.17 (s, 1H), 8.02 (d, J=8.9 Hz, 1H), 7.94 (d, J=8.7 Hz, 1H), 7.79 (d, J=8.5 Hz, 1H), 7.43-7.32 (m, 2H), 4.53 (d, J=6.8 Hz, 2H), 3.98 (s, 2H), 3.56 (m, 2H), 3.04 (m, 2H), 2.87 (s, 3H), 2.44 (m, 1H), 2.00 (m, 2H), 1.77 (m, 2H), 1.41 (s, 6H); MS (ESI) 461.5 m/z [MH+], C$_{26}$H$_{33}$N$_6$O$_2$ requires 461.5.

Tert-butyl4-((4-amino-3-(2-ethoxyquinolin-6-yl)-1H-pyrazolo[3,4-d]pyrimidin-1-yl)methyl)piperidine-1-carboxylate was subjected to the general boc-deprotection procedure and general reductive amination procedure in order to afford the product. $^1$H NMR (300 MHz, CD$_3$OD) δ8.29 (s, 1H), 8.22 (d, J=8.2 Hz, 1H), 8.12 (s, 1H), 7.98 (m, 2H), 7.04 (d, J=8.5 Hz, 1H), 4.55 (q, J=6.8 Hz, 2H), 4.38 (d, J=4.3 Hz, 2H), 2.95 (m, 2H), 2.30 (s, 3H), 2.99 (m, 2H), 1.67 (m, 2H), 1.48 (m, 4H); MS (ESI) 418.3 m/z [MH+], C$_{23}$H$_{28}$N$_7$O requires 418.5.

Example 16: 1-((1-Methylpiperidin-4-yl)methyl)-3-(2-(2,2,2-trifluoroethoxy)quinolin-6-yl)-1H-pyrazolo[3,4-d]pyrimidin-4-amine

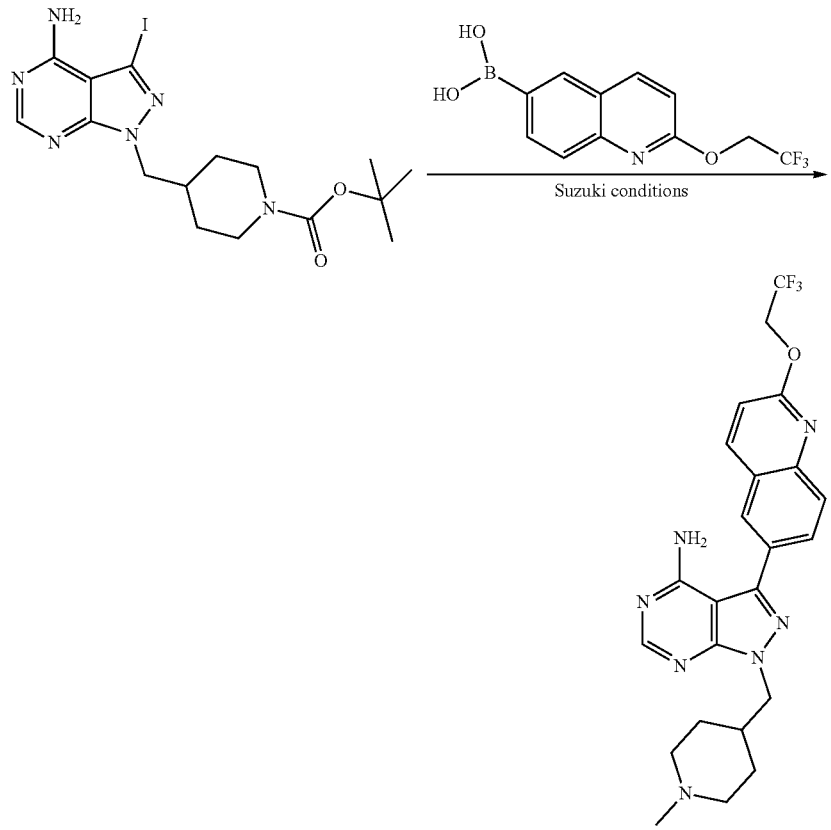

2-(2,2,2-Trifluoroethoxy)quinolin-6-ylboronic acid and tert-butyl 4-((4-amino-3-iodo-1H-pyrazolo[3,4-d]pyrimidin-1-yl)methyl)piperidine-1-carboxylate were subjected to the general Suzuki coupling procedure followed by the general boc-deprotection procedure and general reductive amination procedure in order to afford the product. $^1$H NMR (300 MHz, CD$_3$OD) δ8.49 (s, 1H), 8.39 (d, J=8.5 Hz, 1H), 8.24 (s, 1H), 8.04 (s, 2H), 7.18 (d, J=7.0 Hz, 1H), 5.09 (q, J=8.7 Hz, 2H), 4.52 (s, 2H), 3.54 (m, 2H), 3.04 (m, 2H), 2.84 (s, 3H), 2.45 (m, 1H), 1.98 (m, 2H), 1.75 (m, 2H); MS (ESI) 472.2 m/z [MH+], C$_{23}$H$_{25}$F$_3$N$_7$O requires 472.5.

Example 17: 3-(6-ethoxynaphthalen-2-yl)-1-isobutyl-1H-pyrazolo[3,4-(1]pyrimidin-4-amine

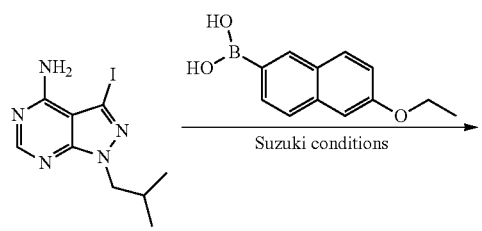

6-ethoxynaphthalen-2-ylboronic acid and 3-iodo-1-isobutyl-1H-pyrazolo[3,4-d]pyrimidin-4-amine were subjected to the general Suzuki coupling procedure in order to afford the product. $^1$H NMR (300 MHz, CD$_3$OD) δ8.27 (s, 1H), 8.09 (s, 1H), 7.96 (d, J=8.1 Hz, 1H), 7.89 (d, J=9.1 Hz, 1H), 7.75 (dd, J=8.2, 2.0 Hz, 1H), 7.32 (s, 1H), 7.22 (dd, J=2.4 Hz, 1H), 4.28-4.17 (m, 4H), 2.39 (m, 1H), 1.48 (t, J=6.8 Hz, 3H), 0.96 (d, J=6.6 Hz, 6H); MS (ESI) 362.4 m/z [MH+], $C_{21}H_{24}N_5O$ requires 362.2.

Example 18: 3-(2-Cyclopropoxyquinolin-6-yl)-1-isobutyl-1H-pyrazolo[3,4-(1]pyrimidin-4-amine

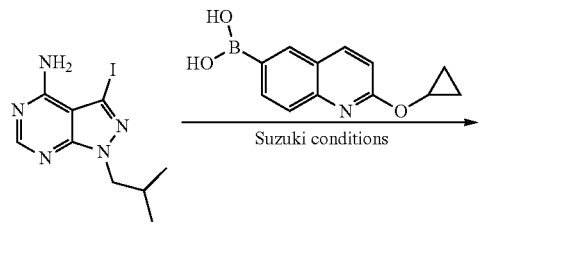

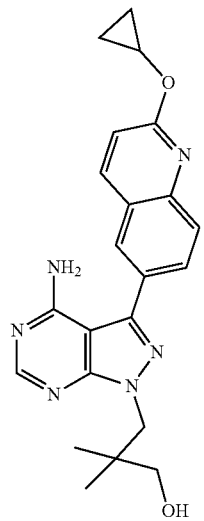

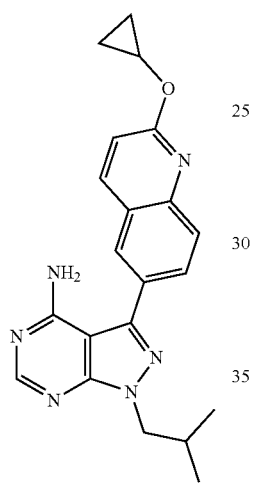

2-Cyclopropoxyquinolin-6-ylboronic acid and 3-iodo-1-isobutyl-1H-pyrazolo[3,4-d]pyrimidin-4-amine were subjected to the general Suzuki coupling procedure in order to afford the product. $^1$H NMR (300 MHz, CD$_3$OD) δ8.25 (s, 1H), 8.23 (d, J=8.9 Hz, 1H), 8.10 (s, 1H), 8.00-7.91 (m, 2H), 7.02 (d, J=8.7 Hz, 1H), 4.46 (s, 1H), 4.22 (d, J=7.4 Hz, 2H), 2.36 (m, 1H), 0.96 (d, J=6.6 Hz, 6H), 0.91-0.72 (m, 4H); MS (ESI) 375.4 m/z [MH+], $C_{21}H_{23}N_6O$ requires 375.4.

Example 19: 3-(4-Amino-3-(2-cyclopropoxyquinolin-6-yl)-1H-pyrazolo[3,4-d]pyrimidin-1-yl)-2,2-dimethylpropan-1-ol

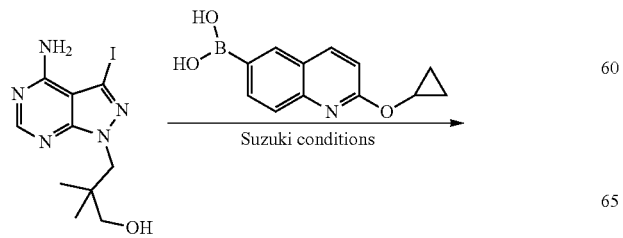

2-Cyclopropoxyquinolin-6-ylboronic acid and previously reported 3-(4-amino-3-iodo-1H-pyrazolo[3,4-d]pyrimidin-1-yl)-2,2-dimethylpropan-1-ol were subjected to the general Suzuki coupling procedure in order to afford the product. $^1$H NMR (300 MHz, CD$_3$OD) δ8.65 (s, 1H), 8.50 (s, 1H), 8.36 (m, 1H), 8.21-8.05 (m, 2H), 7.51 (d, J=8.3 Hz, 1H), 4.59 (s, 2H), 4.47 (s, 2H), 4.46 (m, 1H), 1.01 (s, 6H), 0.70 (m, 4H); MS (ESI) 405.2 m/z [MH+], $C_{22}H_{25}N_6O_2$ requires 405.4.

Example 20: 3-(2-Cyclopropoxyquinolin-6-yl)-1-((3-methyloxetan-3-yl)methyl)-1H-pyrazolo[3,4-d]pyrimidin-4-amine

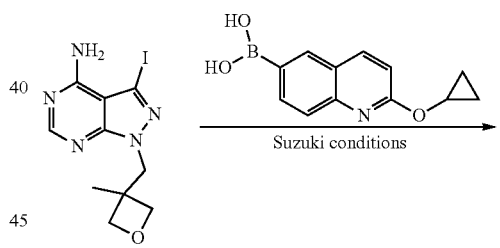

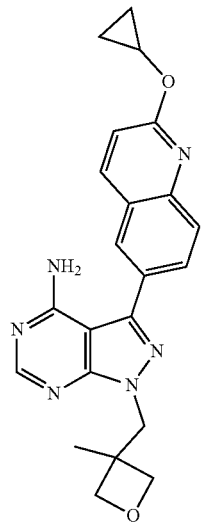

2-Cyclopropoxyquinolin-6-ylboronic acid and 3-iodo-1-((3-methyloxetan-3-yl)methyl)-1H-pyrazolo[3,4-d]pyrimidin-4-amine were subjected to the general Suzuki coupling procedure in order to afford the product. $^1$H NMR (300 MHz, CDCl$_3$) δ8.41 (s, 1H), 8.12-8.01 (m, 3H), 7.96 (d, J=8.3 Hz, 1H), 6.97 (d, J=8.0 Hz, 1H), 5.54 (s, 2H), 4.91 (d, J=6.1 Hz, 2H), 4.64 (s, 2H), 4.56 (m, 1H), 4.45 (d, J=6.1 Hz, 2H), 1.36 (s, 3H), 0.95-0.82 (m, 4H); MS (ESI) 403.2 m/z [MH+], C$_{22}$H$_{23}$N$_6$O$_2$ requires 403.4.

Example 21: 3-(6-Cyclopropoxynaphthalen-2-yl)-1-((tetrahydro-2H-pyran-4-yl)methyl)-1H-pyrazolo[3,4-(1]pyrimidin-4-amine

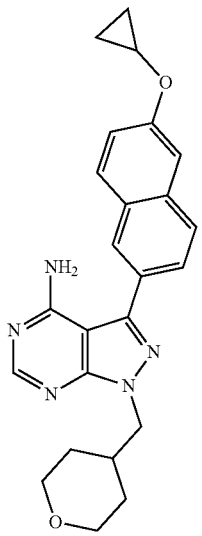

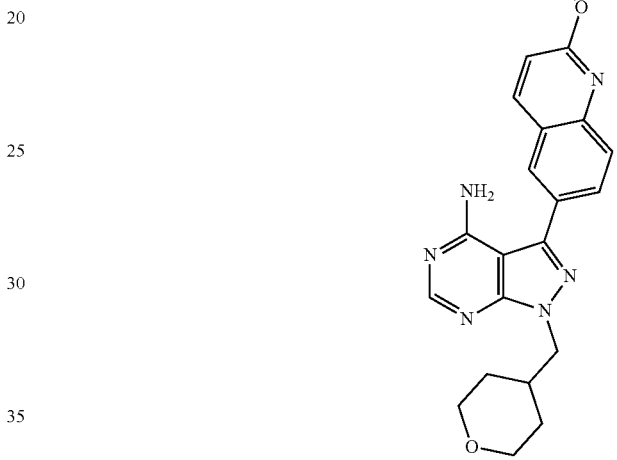

2-(6-Cyclopropoxynaphthalen-2-yl)-4,4,5,5-tetramethyl-1,3,2-dioxaborolane and 3-iodo-1-((tetrahydro-2H-pyran-4-yl)methyl)-1H-pyrazolo[3,4-d]pyrimidin-4-amine were subjected to the general Suzuki coupling procedure in order to afford the product. $^1$H NMR (300 MHz, CD$_3$OD) δ8.47 (s, 1H), 8.16 (s, 1H), 8.03 (d, J=8.2 Hz, 1H), 7.92 (d, J=9.1 Hz, 1H), 7.78 (d, J=8.2 Hz, 1H), 7.64 (s, 1H), 7.27 (dd, J=9.1, 2.2 Hz, 1H) 4.45 (d, J=6.8 Hz, 2H,), 3.99 (m, 1H), 3.76 (m, 2H), 3.05 (m, 2H), 2.40 (m, 1H), 1.61 (m, 2H), 1.46 (m, 2H), 0.93-0.80 (m, 4H); MS (ESI) 416.4 m/z [MH+], C$_{24}$H$_{25}$N$_5$O$_2$ requires 416.4.

Example 22: 3-(2-Cyclopropoxyquinolin-6-yl)-1-((tetrahydro-2H-pyran-4-yl)methyl)-1H-pyrazolo[3,4-(1]pyrimidin-4-amine

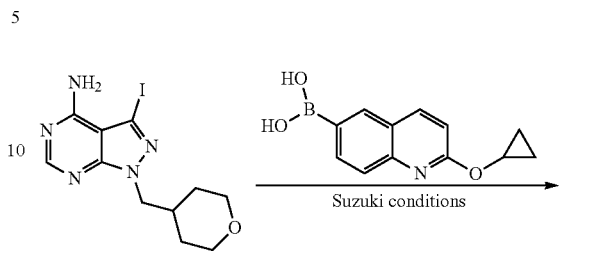

2-cyclopropoxyquinolin-6-ylboronic acid and 3-iodo-1-((tetrahydro-2H-pyran-4-yl)methyl)-1H-pyrazolo[3,4-d]pyrimidin-4-amine were subjected to the general Suzuki coupling procedure in order to afford the product. $^1$H NMR (300 MHz, CD$_3$OD) δ8.31 (s, 1H), 8.22 (d, J=8.9 Hz, 1H), 8.12 (d, J=1.8 Hz, 1H), 8.06 (d, J=8.7 Hz, 1H), 8.00 (dd, 1.2 Hz, 1H), 7.07 (d, J=8.9 Hz, 1H), 4.47 (m, 1H) 4.36 (d, J=7.2 Hz, 2H,), 3.98 (m, 2H), 3.42 (m, 2H), 2.34 (m, 1H), 1.59 (m, 2H), 1.49 (m, 2H), 0.93-0.83 (m, 4H); MS (ESI) 416.4 m/z [MH+], C$_{23}$H$_{24}$N$_6$O$_2$ requires 416.4.

Example 23: 1-(4-amino-3-(2-ethoxyquinolin-6-yl)-1H-pyrazolo[3,4-d]pyrimidin-1-yl)-2-methylpropan-2-ol

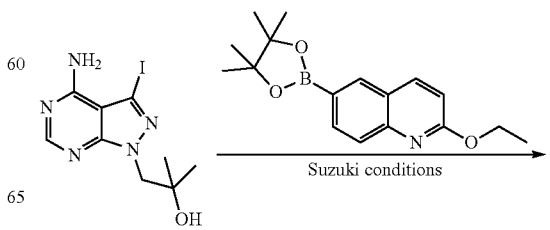

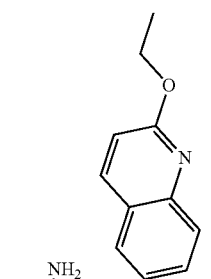

2-ethoxy-6-(4,4,5,5-tetramethyl-1,3,2-dioxaborolan-2-yl)quinoline and 1-(4-amino-3-iodo-1H-pyrazolo[3,4-d]pyrimidin-1-yl)-2-methylpropan-2-ol were subjected to the general Suzuki coupling procedure to afford compound the product. $^1$H NMR (300 MHz, CD$_3$OD) δ8.69 (d, J=9.1 Hz, 1H), 8.45 (s, 1H), 8.34 (s, 1H), 8.17 (d, J=8.0 Hz, 1H), 8.04 (d, J=7.4 Hz, 1H), 7.45 (d, J=7.4 Hz, 1H), 4.67 (q, J=6.0 Hz, 2H), 4.50 (s, 2H), 1.54 (t, J=6.5 Hz, 3H), 1.31 (s, 6H). MS (ESI) 379.2 m/z [MH+], C$_{20}$H$_{23}$N$_6$O$_2$ requires 379.1.

Example 24: 1-(4-Amino-3-(6-cyclopropoxynaphthalen-2-yl)-1H-pyrazolo[3,4-d]pyrimidin-1-yl)-2-methylpropan-2-ol

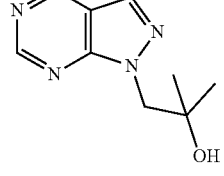

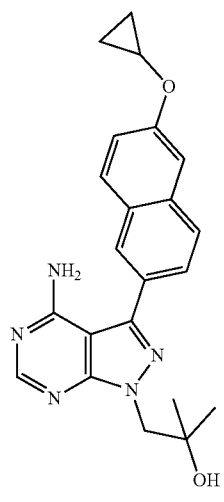

2-(6-Cyclopropoxynaphthalen-2-yl)-4,4,5,5-tetramethyl-1,3,2-dioxaborolane and 1-(4-amino-3-iodo-1H-pyrazolo[3,4-d]pyrimidin-1-yl)-2-methylpropan-2-ol were subjected to the general Suzuki coupling procedure to afford title compound the product; $^1$H NMR (500 MHz, CD$_3$OD) δ8.26 (s, 1H), 8.08 (s, 1H), 7.93 (d, J=8.4 Hz, 1H), 7.85 (d, J=8.81 Hz, 1H), 7.76 (d, J=8.4 Hz, 1H), 7.57 (s, 1H), 7.20 (dd, J=8.8, 1.8 Hz, 1H), 4.40 (s, 2H), 3.91 (m, 1H), 1.27 (s, 6H), 0.88 (m, 2H), 0.78 (m, 2H). MS (ESI) 390.2 m/z [MH+], C$_{22}$H$_{24}$N$_5$O$_2$ requires 390.1.

Example 25: 1-(4-Amino-3-(2-cyclopropoxyquinolin-6-yl)-1H-pyrazolo[3,4-d]pyrimidin-1-yl)-2-methylpropan-2-ol

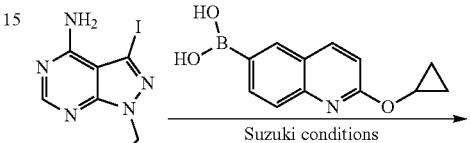

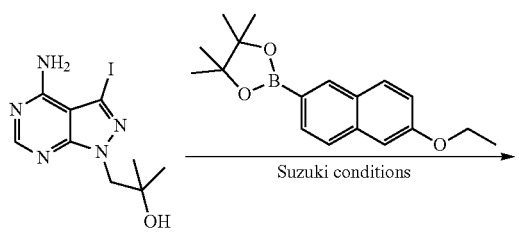

2-Cyclopropoxyquinolin-6-ylboronic acid and 1-(4-amino-3-iodo-1H-pyrazolo[3,4-d]pyrimidin-1-yl)-2-methylpropan-2-ol were subjected to the general Suzuki coupling procedure in order to afford the product. NMR (300 MHz, CD$_3$OD) δ8.28 (s, 1H), 8.28-8.24 (d, J=8.9 Hz, 1H), 8.15 (t, J=1.4 Hz, 1H), 8.01 (d, J=1.2 Hz, 2H), 7.06 (d, J=8.7 Hz, 1H), 4.53-4.45 (m, 1H), 4.42 (s, 2H), 1.28 (s, 6H), 0.92-0.85 (m, 2H), 0.85-0.77 (m, 2H); MS (ESI) 391.1 m/z [MH$^+$], C$_{21}$H$_{23}$N$_6$O$_2$ requires 391.2.

Example 26: 3-(4-Amino-3-(6-cyclopropoxynaphthalen-2-yl)-1H-pyrazolo[3,4-d]pyrimidin-1-yl)-2,2-dimethylpropan-1-ol

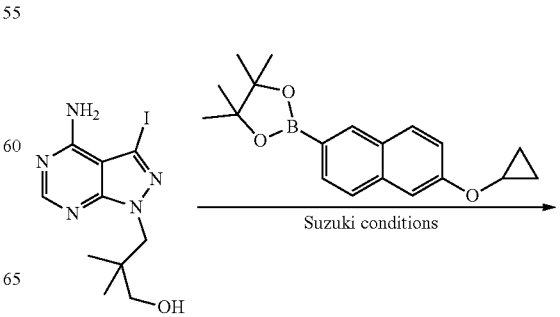

-continued

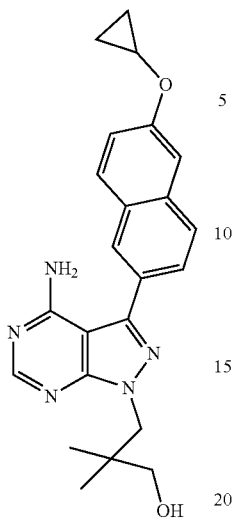

2-(6-Cyclopropoxynaphthalen-2-yl)-4,4,5,5-tetramethyl-1,3,2-dioxaborolane and previously reported 3-(4-amino-3-iodo-1H-pyrazolo[3,4-d]pyrimidin-1-yl)-2,2-dimethylpropan-1-ol were subjected to the general Suzuki coupling procedure in order to afford the product. $^1$H NMR (300 MHz, CD$_3$OD) δ8.30 (s, 1H), 8.12 (s, 1H), 8.00 (d, J=8.7 Hz, 1H), 7.90 (d, J=8.9 Hz, 1H), 7.78 (dd, 1.5 Hz, 1H), 7.62 (d, 1H), 7.24 (dd, J=9.1, 2.4 Hz, 1H), 4.33 (s, 2H), 3.97 (m, 1H), 3.32 (s, 2H), 1.22 (s, 6H), 0.94-0.81 (m, 4H); MS (ESI) 404.5 m/z [MH+], C$_{23}$H$_{26}$N$_5$O$_2$ requires 404.4.

Examples 27-119

The following compounds were prepared by the methothes disclosed herein:

| Ex. No. | Compound |
|---|---|
| 27 | 3-(2-methoxyquinolin-6-yl)-1-((tetrahydro-2H-pyran-4-yl)methyl)-1H-pyrazolo[3,4-d]pyrimidin-4-amine |
| 28 | 3-(2-(cyclopropylmethoxy)quinolin-6-yl)-1-((tetrahydro-2H-pyran-4-yl)methyl)-1H-pyrazolo[3,4-d]pyrimidin-4-amine |
| 29 | 3-(6-(cyclopropylmethoxy)naphthalen-2-yl)-1-((tetrahydro-2H-pyran-4-yl)methyl)-1H-pyrazolo[3,4-d]pyrimidin-4-amine |
| 30 | 3-(6-cyclobutoxynaphthalen-2-yl)-1-((tetrahydro-2H-pyran-4-yl)methyl)-1H-pyrazolo[3,4-d]pyrimidin-4-amine |
| 31 | 3-(6-(oxetan-3-yloxy)naphthalen-2-yl)-1-((tetrahydro-2H-pyran-4-yl)methyl)-1H-pyrazolo[3,4-d]pyrimidin-4-amine |
| 32 | 3-(4-amino-3-(6-ethoxynaphthalen-2-yl)-1H-pyrazolo[3,4-d]pyrimidin-1-yl)-2,2-dimethylpropan-1-ol |
| 33 | 1-(6-(4-amino-1-isobutyl-1H-pyrazolo[3,4-d]pyrimidin-3-yl)naphthalen-2-yloxy)-2-methylpropan-2-ol |
| 34 | 2-(6-(4-amino-1-isobutyl-1H-pyrazolo[3,4-d]pyrimidin-3-yl)naphthalen-2-yloxy)ethanol |
| 35 | 1-isobutyl-3-(6-(oxetan-3-yloxy)naphthalen-2-yl)-1H-pyrazolo[3,4-d]pyrimidin-4-amine |
| 36 | 1-isobutyl-3-(6-(2-methoxyethoxy)naphthalen-2-yl)-1H-pyrazolo[3,4-d]pyrimidin-4-amine |
| 37 | 3-(4-amino-3-(2-ethoxyquinolin-6-yl)-1H-pyrazolo[3,4-d]pyrimidin-1-yl)-2,2-dimethylpropan-1-ol |
| 38 | 3-(2-(2-methoxyethoxy)quinolin-6-yl)-1-neopentyl-1H-pyrazolo[3,4-d]pyrimidin-4-amine |
| 39 | 3-(2-cyclopropoxyquinolin-6-yl)-1-(piperidin-4-ylmethyl)-1H-pyrazolo[3,4-d]pyrimidin-4-amine |
| 40 | 1-(azetidin-3-ylmethyl)-3-(2-cyclopropoxyquinolin-6-yl)-1H-pyrazolo[3,4-d]pyrimidin-4-amine |
| 41 | 3-(2-cyclopropoxyquinolin-6-yl)-1-((1-methylazetidin-3-yl)methyl)-1H-pyrazolo[3,4-d]pyrimidin-4-amine |
| 42 | 3-(2-(2-methoxyethoxy)quinolin-6-yl)-1-((1-methylpiperidin-4-yl)methyl)-1H-pyrazolo[3,4-d]pyrimidin-4-amine |
| 43 | 1-isobutyl-3-(2-(2,2,2-trifluoroethoxy)quinolin-6-yl)-1H-pyrazolo[3,4-d]pyrimidin-4-amine |
| 44 | 1-(piperidin-4-ylmethyl)-3-(2-(2,2,2-trifluoroethoxy)quinolin-6-yl)-1H-pyrazolo[3,4-d]pyrimidin-4-amine |
| 45 | 2-(3-(4-amino-3-(2-cyclopropoxyquinolin-6-yl)-1H-pyrazolo[3,4-d]pyrimidin-1-yl)-2,2-dimethylpropoxy)ethanol |
| 46 | 1-(4-amino-3-(2-(2,2,2-trifluoroethoxy)quinolin-6-yl)-1H-pyrazolo[3,4-d]pyrimidin-1-yl)-2-methylpropan-2-ol |
| 47 | 3-(7-ethoxynaphthalen-2-yl)-1-isobutyl-1H-pyrazolo[3,4-d]pyrimidin-4-amine |
| 48 | 3-(7-ethoxynaphthalen-2-yl)-1-(piperidin-4-ylmethyl)-1H-pyrazolo[3,4-d]pyrimidin-4-amine |
| 49 | 3-(6-ethoxynaphthalen-2-yl)-1-((3-methyloxetan-3-yl)methyl)-1H-pyrazolo[3,4-d]pyrimidin-4-amine |
| 50 | 2-(4-amino-3-(6-ethoxynaphthalen-2-yl)-1H-pyrazolo[3,4-d]pyrimidin-1-yl)-1-morpholinoethanone |
| 51 | 2-(4-amino-3-(6-cyclopropoxynaphthalen-2-yl)-1H-pyrazolo[3,4-d]pyrimidin-1-yl)-1-morpholinoethanone |

-continued

| Ex. No. | Compound |
|---|---|
| 52 | 2-((4-amino-3-(6-(methoxymethyl)naphthalen-2-yl)-1H-pyrazolo[3,4-d]pyrimidin-1-yl)methyl)-1,1,1,3,3,3-hexafluoropropan-2-ol |
| 53 | 2-((4-amino-3-(2-cyclopropoxyquinolin-6-yl)-1H-pyrazolo[3,4-d]pyrimidin-1-yl)methyl)-1,1,1,3,3,3-hexafluoropropan-2-ol |
| 54 | 1-(3-(6-cyclopropoxynaphthalen-2-yl)-1H-pyrrolo[3,2-c]pyridin-1-yl)-2-methylpropan-2-ol |
| 55 | 1-(4-amino-5-(2-cyclopropoxyquinolin-6-yl)-7H-pyrrolo[2,3-d]pyrimidin-7-yl)-2-methylpropan-2-ol |
| 56 | 4-(4-amino-3-(2-cyclopropoxyquinolin-6-yl)-1H-pyrazolo[3,4-d]pyrimidin-1-yl)-2,3,3-trimethylbutan-2-ol |
| 57 | 1-((4-amino-3-(2-cyclopropoxyquinolin-6-yl)-1H-pyrazolo[3,4-d]pyrimidin-1-yl)methyl)cyclobutanol |
| 58 | 1-(4-amino-5-(6-cyclopropoxynaphthalen-2-yl)-7H-pyrrolo[2,3-d]pyrimidin-7-yl)-2-methylpropan-2-ol |
| 59 | 1-((4-amino-3-(6-cyclopropoxynaphthalen-2-yl)-1H-pyrazolo[3,4-d]pyrimidin-1-yl)methyl)cyclobutanol |
| 60 | 1-((4-amino-3-(2-cyclopropoxyquinolin-6-yl)-1H-pyrazolo[3,4-d]pyrimidin-1-yl)methyl)cyclopentanol |
| 61 | 1-((4-amino-3-(6-cyclopropoxynaphthalen-2-yl)-1H-pyrazolo[3,4-d]pyrimidin-1-yl)methyl)cyclopentanol |
| 62 | 4-((4-amino-3-(2-cyclopropoxyquinolin-6-yl)-1H-pyrazolo[3,4-d]pyrimidin-1-yl)methyl)-tetrahydro-2H-pyran-4-ol |
| 63 | 4-((4-amino-3-(6-cyclopropoxynaphthalen-2-yl)-1H-pyrazolo[3,4-d]pyrimidin-1-yl)methyl)-tetrahydro-2H-pyran-4-ol |
| 64 | (3-((4-amino-3-(2-cyclopropoxyquinolin-6-yl)-1H-pyrazolo[3,4-d]pyrimidin-1-yl)methyl)oxetan-3-yl)methanol |
| 65 | (3-((4-amino-3-(6-cyclopropoxynaphthalen-2-yl)-1H-pyrazolo[3,4-d]pyrimidin-1-yl)methyl)oxetan-3-yl)methanol |
| 66 | 3-(6-cyclopropoxynaphthalen-2-yl)-1-(2-methoxy-2-methylpropyl)-1H-pyrazolo[3,4-d]pyrimidin-4-amine |
| 67 | 3-(2-cyclopropoxyquinolin-6-yl)-1-(2-methoxy-2-methylpropyl)-1H-pyrazolo[3,4-d]pyrimidin-4-amine |
| 68 | methyl 3-(4-amino-3-(6-cyclopropoxynaphthalen-2-yl)-1H-pyrazolo[3,4-d]pyrimidin-1-yl)-2,2-dimethylpropanoate |
| 69 | methyl 3-(4-amino-3-(2-cyclopropoxyquinolin-6-yl)-1H-pyrazolo[3,4-d]pyrimidin-1-yl)-2,2-dimethylpropanoate |
| 70 | 4-((4-amino-3-(6-ethoxynaphthalen-2-yl)-1H-pyrazolo[3,4-d]pyrimidin-1-yl)methyl)piperidin-4-ol |
| 71 | 4-((4-amino-3-(6-ethoxynaphthalen-2-yl)-1H-pyrazolo[3,4-d]pyrimidin-1-yl)methyl)-1-methylpiperidin-4-ol |
| 72 | methyl 2-((6-(4-amino-1-((1-methylpiperidin-4-yl)methyl)-1H-pyrazolo[3,4-d]pyrimidin-3-yl)naphthalen-2-yl)oxy)acetate |
| 73 | 2-((6-(4-amino-1-((1-methylpiperidin-4-yl)methyl)-1H-pyrazolo[3,4-d]pyrimidin-3-yl)naphthalen-2-yl)oxy)acetonitrile |
| 74 | 4-((4-amino-3-(6-ethoxynaphthalen-2-yl)-1H-pyrazolo[3,4-d]pyrimidin-1-yl)methyl)piperidine-4-carbonitrile |
| 75 | 4-((4-amino-3-(6-ethoxynaphthalen-2-yl)-1H-pyrazolo[3,4-d]pyrimidin-1-yl)methyl)-1-methylpiperidine-4-carbonitrile |
| 76 | 3-(4-amino-3-(6-cyclopropoxynaphthalen-2-yl)-1H-pyrazolo[3,4-d]pyrimidin-1-yl)-2,2-dimethylpropanoic acid |
| 77 | 3-(6-cyclopropoxynaphthalen-2-yl)-1-(2-fluoro-2-methylpropyl)-1H-pyrazolo[3,4-d]pyrimidin-4-amine |
| 78 | 4-((4-amino-3-(6-cyclopropoxynaphthalen-2-yl)-1H-pyrazolo[3,4-d]pyrimidin-1-yl)methyl)piperidin-4-ol |
| 79 | 4-((4-amino-3-(6-cyclopropoxynaphthalen-2-yl)-1H-pyrazolo[3,4-d]pyrimidin-1-yl)methyl)-1-methylpiperidin-4-ol |
| 80 | 4-((4-amino-3-(2-ethoxyquinolin-6-yl)-1H-pyrazolo[3,4-d]pyrimidin-1-yl)methyl)-1-methylpiperidin-4-ol |
| 81 | 4-((4-amino-3-(2-ethoxyquinolin-6-yl)-1H-pyrazolo[3,4-d]pyrimidin-1-yl)methyl)-1-methylpiperidin-4-ol |
| 82 | 4-((4-amino-3-(2-cyclopropoxyquinolin-6-yl)-1H-pyrazolo[3,4-d]pyrimidin-1-yl)methyl)piperidin-4-ol |
| 83 | 4-((4-amino-3-(6-cyclopropoxynaphthalen-2-yl)-1H-pyrazolo[3,4-d]pyrimidin-1-yl)methyl)-1-methylpiperidine-4-carbonitrile |
| 84 | 4-((4-amino-3-(2-ethoxyquinolin-6-yl)-1H-pyrazolo[3,4-d]pyrimidin-1-yl)methyl)piperidin-4-ol |
| 85 | 4-((4-amino-3-(2-cyclopropoxyquinolin-6-yl)-1H-pyrazolo[3,4-d]pyrimidin-1-yl)methyl)-1-methylpiperidin-4-ol |
| 86 | 4-((4-amino-3-(2-ethoxyquinolin-6-yl)-1H-pyrazolo[3,4-d]pyrimidin-1-yl)methyl)piperidine-4-carbonitrile |
| 87 | 4-((4-amino-3-(2-ethoxyquinolin-6-yl)-1H-pyrazolo[3,4-d]pyrimidin-1-yl)methyl)-1-methylpiperidine-4-carbonitrile |
| 88 | 2-(6-(4-amino-1-(2-hydroxy-2-methylpropyl)-1H-pyrazolo[3,4-d]pyrimidin-3-yl)naphthalen-2-yloxy)acetonitrile |
| 89 | methyl 2-(6-(4-amino-1-(piperidin-4-ylmethyl)-1H-pyrazolo[3,4-d]pyrimidin-3-yl)quinolin-2-yloxy)acetate |

-continued

| Ex. No. | Compound |
|---|---|
| 90 | 3-((4-amino-3-(6-cyclopropoxynaphthalen-2-yl)-1H-pyrazolo[3,4-d]pyrimidin-1-yl)methyl)azetidin-3-ol |
| 91 | 3-((4-amino-3-(6-cyclopropoxynaphthalen-2-yl)-1H-pyrazolo[3,4-d]pyrimidin-1-yl)methyl)-1-methylazetidin-3-ol |
| 92 | 4-((4-amino-3-(2-cyclopropoxyquinolin-6-yl)-1H-pyrazolo[3,4-d]pyrimidin-1-yl)methyl)-1-methylpiperidine-4-carbonitrile |
| 93 | 3-((4-amino-3-(2-ethoxyquinolin-6-yl)-1H-pyrazolo[3,4-d]pyrimidin-1-yl)methyl)azetidin-3-ol |
| 94 | 3-(6-(difluoromethoxy)naphthalen-2-yl)-1-(piperidin-4-ylmethyl)-1H-pyrazolo[3,4-d]pyrimidin-4-amine |
| 95 | 3-(6-(difluoromethoxy)naphthalen-2-yl)-1-((1-methylpiperidin-4-yl)methyl)-1H-pyrazolo[3,4-d]pyrimidin-4-amine |
| 96 | 3-((4-amino-3-(6-ethoxynaphthalen-2-yl)-1H-pyrazolo[3,4-d]pyrimidin-1-yl)methyl)azetidin-3-ol |
| 97 | 3-((4-amino-3-(6-ethoxynaphthalen-2-yl)-1H-pyrazolo[3,4-d]pyrimidin-1-yl)methyl)-1-methylazetidin-3-ol |
| 98 | 4-((4-amino-3-(6-(difluoromethoxy)naphthalen-2-yl)-1H-pyrazolo[3,4-d]pyrimidin-1-yl)methyl)piperidin-4-ol |
| 99 | 4-((4-amino-3-(6-(difluoromethoxy)naphthalen-2-yl)-1H-pyrazolo[3,4-d]pyrimidin-1-yl)methyl)-1-methylpiperidin-4-ol |
| 100 | 4-((4-amino-3-(6-(difluoromethoxy)naphthalen-2-yl)-1H-pyrazolo[3,4-d]pyrimidin-1-yl)methyl)piperidine-4-carbonitrile |
| 101 | 3-((4-amino-3-(2-cyclopropoxyquinolin-6-yl)-1H-pyrazolo[3,4-d]pyrimidin-1-yl)methyl)azetidin-3-ol |
| 102 | 4-((4-amino-3-(6-(difluoromethoxy)naphthalen-2-yl)-1H-pyrazolo[3,4-d]pyrimidin-1-yl)methyl)-1-methylpiperidine-4-carbonitrile |
| 103 | 3-((4-amino-3-(2-cyclopropoxyquinolin-6-yl)-1H-pyrazolo[3,4-d]pyrimidin-1-yl)methyl)-1-methylazetidin-3-ol |
| 104 | 1-(3-(6-ethoxynaphthalen-2-yl)-1-((1-(methylcarbamoyl)piperidin-4-yl)methyl)-1H-pyrazolo[3,4-d]pyrimidin-4-yl)-3-methylurea |
| 105 | 4-((4-amino-3-(2-ethoxyquinolin-6-yl)-1H-pyrazolo[3,4-d]pyrimidin-1-yl)methyl)-N-methylpiperidine-1-carboxamide |
| 106 | 3-(2-ethoxyquinolin-6-yl)-1-isopropyl-1H-pyrazolo[3,4-d]pyrimidin-4-amine |
| 107 | 3-(6-ethoxynaphthalen-2-yl)-1-(2-(piperidin-4-yl)ethyl)-1H-pyrazolo[3,4-d]pyrimidin-4-amine |
| 108 | 3-(6-ethoxynaphthalen-2-yl)-1-(2-(1-methylpiperidin-4-yl)ethyl)-1H-pyrazolo[3,4-d]pyrimidin-4-amine |
| 109 | 3-(6-ethoxynaphthalen-2-yl)-1-(2-(1-ethylpiperidin-4-yl)ethyl)-1H-pyrazolo[3,4-d]pyrimidin-4-amine |
| 110 | 3-(6-ethoxynaphthalen-2-yl)-1-(2-(1-propylpiperidin-4-yl)ethyl)-1H-pyrazolo[3,4-d]pyrimidin-4-amine |
| 111 | 1-(2-(1-(3-aminopropyl)piperidin-4-yl)ethyl)-3-(6-ethoxynaphthalen-2-yl)-1H-pyrazolo[3,4-d]pyrimidin-4-amine |
| 112 | 3-(6-ethoxynaphthalen-2-yl)-1-(1-propylpiperidin-4-yl)-1H-pyrazolo[3,4-d]pyrimidin-4-amine |
| 113 | 1-(1-(3-aminopropyl)piperidin-4-yl)-3-(6-ethoxynaphthalen-2-yl)-1H-pyrazolo[3,4-d]pyrimidin-4-amine |
| 114 | 1-(6-ethoxynaphthalen-2-yl)-3-(piperidin-4-ylmethyl)imidazo[1,5-a]pyrazin-8-amine |
| 115 | 1-(6-ethoxynaphthalen-2-yl)-3-((1-methylpiperidin-4-yl)methyl)imidazo[1,5-a]pyrazin-8-amine |
| 116 | 1-isopropyl-3-(6-(oxetan-3-yloxy)naphthalen-2-yl)-1H-pyrazolo[3,4-d]pyrimidin-4-amine |
| 117 | 1-((6-(4-amino-1-isopropyl-1H-pyrazolo[3,4-d]pyrimidin-3-yl)naphthalen-2-yl)oxy)-2-methylpropan-2-ol |
| 118 | 2-((6-(4-amino-1-isopropyl-1H-pyrazolo[3,4-d]pyrimidin-3-yl)naphthalen-2-yl)oxy)ethan-1-ol |
| 119 | 3-(2-ethoxyquinolin-6-yl)-1-(piperidin-4-ylmethyl)-1H-pyrazolo[3,4-d]pyrimidin-4-amine. |

Biological Example 1: TgCDPK1 Enzymatic Inhibition Assay

Inhibitors were evaluated in triplicate in eight-point dilutions (3-fold dilutions) during the enzymatic reactions. TgCDPK1 enzymatic inhibition was determined with a coupled luciferase assay (Kinaseglo®). 2.1 nM TgCDPK1 and 20 µM BioSyntide-2 (American Peptide Company, Inc. Sunnyvale, Calif.)) were incubated in 25 µL of buffer containing 1 mM EGTA (pH 7.2), 10 mM $MgCl_2$, 20 mM HEPES, pH 7.5 (KOH), 0.1% BSA, and 2 mM $CaCl_2$. The reaction was initiated with the addition of ATP at a 10 µM final concentration. After incubating at 30° C. for 90 min., changes in ATP concentration were determined by adding Kinaseglo® luciferase reagent (Promega, Madison, Wis.) and measuring luminescence with a MicroBeta2 multi-label plate reader (Perkin Elmer, Waltham, Mass.). Results were converted to percent inhibition, and $IC_{50}$ values were calculated using nonlinear regression analysis in GraphPad Prism.

Biological Example 2: Src Kinase Enzymatic Inhibition Assay

Inhibitors were evaluated in triplicate in eight-point dilutions (3-fold dilutions) during the enzymatic reactions. Chicken Src enzymatic inhibition was determined with a coupled luciferase assay (Kinaseglo®). 2 nM Src and 61 µM Src substrate peptide (GenScript, Piscataway, N.J.) were incubated in 25 µL of buffer containing 40 mM Tris-HCl (pH 7.5), 20 mM $MgCl_2$, 1 mM $MnCl_2$, 1 mM DTT, and 0.1% BSA. The reaction was initiated with the addition of ATP at a 10 µM final concentration. After incubating at 30° C. for 90 min., changes in ATP concentration were determined by adding Kinaseglo® luciferase reagent (Promega, Madison, Wis.) and measuring luminescence with a MicroBeta2 multi-label plate reader (Perkin Elmer, Waltham, Mass.). Results were converted to percent inhibition, and IC50 values were calculated using nonlinear regression analysis in GraphPad Prism.

Biological Example 3: Human Cell Growth Inhibition Assay

CRL-8155 human lymphocytic cells (ATCC, WIL2-NS) were cultured in RPMI-1640 growth medium supplemented with 10% heat inactivated fetal bovine serum, 10 mM HEPES, 1 mM sodium pyruvate, and 1 mM L-glutamine. The Alamar Blue® assay (Invitrogen, Grand Island, N.Y.), which measures general cellular metabolism, was used to quantify cell growth. Mid-log cells were seeded in 96-well flat-bottom plates (Corning, Corning, N.Y.) at a density of $3 \times 10^5$ cells/mL containing test compounds at six final concentrations (40 µL, 20 µL, 10 µL, 5 µL, 2.5 µL, and 1.25 µL) in quadruplicate and grown at 37° C. for 48 hours in a 5% $CO_2$ humidified incubator. A ¹/₁₀th volume of Alamar Blue® developing reagent was added to each well and incubated for an additional 3 hours and fluorescence was measured at the respective excitation and emission wavelengths of 560 nm and 590 nm in a FLx800 microplate reader (Biotek, Winooski, Vt.). Percent growth inhibition by test compounds was calculated based on DMSO vehicle and positive controls (50 µL quinacrine), which corresponded to 0% and 100% growth inhibition, respectively.

Biological Example 4: *T. Gondii* Growth Inhibition Assay

The *T. gondii* growth inhibition assay was performed according to a previously reported procedure. Briefly, a dilution series of an inhibitor (diluted in DMSO) was added to DMEM (final DMSO=0.5%). *T. gondii* expressing a β-galactosidase reporter were added to the DMEM and incubated briefly before adding them to fibroblast monolayers in 96 well plates. Plates were visually inspected for evidence of cytotoxic effects on fibroblasts. After 44 h, β-galactosidase was assayed using chlorophenol red β-galactopyranose (Sigma-Aldrich, St. Louis, Mo.) as a substrate. Each dilution series of inhibitor was tested at least twice in triplicate. For assays with drug resistant *T. gondii*, the same procedure was followed except cell lines expressing HA-TgCDPK1 or HA-Gly128Met TgCDPK1 in a "wild type" background were tested.

Biological Example 5: In Vivo Efficacy Against Acute *T. Gondii* Infection in Mice Infection and drug administration were performed as previously reported. Mice were infected with type 1 RH strain *T. gondii* expressing a yellow fluorescent protein. *T. gondii* were harvested from human foreskin fibroblasts, passed through a 3-µm-pore filter, and 10 tachyzoites were inoculated in a volume of 100 µl of phosphate-buffered saline (PBS) intraperitoneally (i.p.) into 4- to 5-week-old, 25-g female CF-1 mice. The compounds were dissolved in polyethylene glycol (PEG) 400 and administered by oral gavage 48 h after inoculation. The control group received PEG 400 only. Groups consisted of 4 mice. After mice were euthanized on the eighth day, the brain and spleen were collected from the mice and peritoneal lavage was performed with 3 ml of PBS (pH 7.4).

In vivo efficacy was evaluated with quantitative real-time PCR for *T. gondii* DNA from the brain and spleen, and quantification of peritoneal *T. gondii* infection as previously described. A sample of 10 µl of peritoneal lavage fluid was examined in a hemocytometer using fluorescence microscopy (excitation/emission 480/535 nm). Yellow-fluorescent tachyzoites were quantified per mL of fluid. After the mice were euthanized, the entire brain and spleen were collected and homogenized. DNA was isolated with a DNA purification kit (Qiagen, Germantown, Md.). 300 ng of total DNA from the brain homogenate and 200 ng of total DNA from the spleen homogenate were analyzed per mouse. A standard curve was generated from DNA purified from *T. gondii* tachyzoites in 10-fold dilutions from 160 ng to 1.6 fg of DNA. Quantitative real-time PCR was performed in duplicate using a 7300 Real-Time PCR System (Applied Biosystems, Grand Island, N.Y.) with iTaq SYBR GREEN PCR Supermix and primers for the *T. gondii* 529-bp repeat element. Results were quantified as *T. gondii* DNA per total DNA. Analysis was performed with GraphPad Prism 5.0 software. This protocol was approved by the institutional animal care and use committee of the Portland Veterans Administration Medical Center.

Biological Example 6: Pharmacokinetic Analysis in Mice and Rats

For mouse oral PK studies, three female BALB/c mice (10 to 12 weeks old) were used in each group. Each group received a test compound at a dose of 10 mg/kg body weight dissolved in 3% ethanol/7% Tween 80/90% normal saline by oral gavage. Blood samples were taken at the designated time points by tail bleeding and centrifuged to obtain plasma. The samples were frozen at −20° C. The test compounds were extracted from the plasma samples using acetonitrile/0.1% formic acid with an internal standard. A standard mix of all test compounds was prepared for comparison and quantification. The compounds were quantified by LC/MS analysis. PK calculations were performed using Phoenix WinNonlin software (Pharsight).

In rats, test compound was administered to Sprague-Dawley jugular canulated rats (Charles River) by either oral gavage or IV injection followed by blood sampling from the jugular vein at designated time points. The oral dose was administered to each rat at 20 mg/kg for compound Ex. 24 and 5 mg/kg for compound Ex. 25 at time=0 in a 1 mL volume of dosing solution (7% Tween 80, 3% EtOH, 5% DMSO, 0.9% saline.) IV injections were administered at 5 mg/kg from time=0 to 3 minutes in a 1 mL volume of dosing solution, and blood was sampled at the same time points via the jugular vein. Experiments were performed with groups of 2 rats each for the oral and IV dosing. Plasma was separated and extracted with acetonitrile and quantified by LC/MS analysis. PK calculations were performed using Phoenix WinNonlin software (Pharsight).

Biological Example 7: Distribution of Compounds Between Mouse Plasma and Brain Mice were injected with test compounds (5 mg/kg IP) and sacrificed at the indicated times for collection of plasma and brain. Compound was dissolved in 0.4 mL of dosing solution (7% Tween 80, 3% ethanol, 5% DMSO, 0.9% saline) for IP injections. The brains were weighed and immediately frozen, then later homogenized in acetonitrile. Prior to animal studies, recovery of test compound was carried out by adding a known amount to a mouse brain in the test extraction solvent and performing the homogenization. Compound recovery was determined by liquid chromatography/tandem mass spectrometry analysis relative to a standard compound amount. Blood was taken from the same mice in heparinized capillary tubes for determination of compound concentration in plasma. The concentration of compound in the brain was obtained by dividing the moles of compound in the brain by the brain volume (obtained from the brain weight assuming 1 g is 1 mL) and correcting for the brain vasculature volume of 3% by weight.

Results

The following compounds were tested for inhibition TgCDPK1:

TABLE 1

| Ex. No. | TgCDPK1 IC50 (µM) |
|---|---|
| 1 | 0.0025 |
| 2 | 0.0172 |
| 3 | 0.0016 |
| 4 | 0.0015 |
| 5 | 0.0045 |
| 6 | 0.0056 |
| 7 | 0.0021 |
| 8 | 0.0949 |
| 9 | 0.0060 |
| 10 | 0.0040 |
| 11 | 0.0155 |
| 12 | 0.0107 |
| 13 | 0.0463 |
| 14 | 0.0242 |
| 15 | 0.0061 |
| 16 | 0.0022 |
| 17 | 0.0008 |
| 18 | 0.0012 |
| 19 | 0.0013 |
| 20 | 0.0018 |
| 21 | 0.0024 |
| 22 | 0.0018 |
| 23 | 0.0033 |
| 24 | 0.0010 |
| 25 | 0.0020 |
| 26 | 0.0009 |
| 27 | 0.0212 |
| 29 | 0.0048 |
| 30 | 0.0026 |
| 31 | 0.0358 |
| 32 | 0.0012 |
| 33 | 0.0057 |
| 34 | 0.0058 |
| 35 | 0.0040 |
| 36 | 0.0017 |
| 37 | 0.0017 |
| 38 | 0.0038 |
| 39 | 0.0010 |
| 40 | 0.0023 |
| 41 | 0.0028 |
| 42 | 0.0080 |
| 43 | 0.0020 |
| 44 | 0.0014 |
| 45 | 1.1991 |
| 46 | 0.0183 |
| 47 | 0.0108 |
| 48 | 0.0191 |
| 49 | 0.0029 |
| 50 | 0.0429 |
| 51 | 0.0158 |
| 52 | 0.0842 |
| 53 | 0.0473 |
| 54 | 1.5500 |
| 55 | 0.0032 |
| 56 | 0.0708 |
| 57 | 0.0061 |
| 58 | 0.0091 |
| 59 | 0.0086 |
| 60 | 0.0127 |
| 61 | 0.0130 |
| 62 | 0.0192 |
| 63 | 0.0128 |
| 64 | 0.0036 |
| 65 | 0.0029 |
| 66 | 1.6629 |
| 67 | 0.4295 |
| 68 | 0.0097 |
| 69 | 0.0432 |
| 70 | 0.0233 |
| 71 | 0.0593 |
| 72 | 0.0496 |
| 73 | 0.0738 |
| 74 | 0.0027 |
| 75 | 0.0183 |
| 76 | 0.0194 |
| 77 | 0.0064 |
| 78 | 0.0007 |
| 79 | 0.0045 |
| 80 | 0.0231 |
| 81 | 0.0013 |
| 82 | 0.0007 |
| 83 | 0.0035 |
| 84 | 0.0040 |
| 85 | 0.0210 |
| 86 | 0.0015 |
| 87 | 0.1030 |
| 88 | 0.1124 |
| 89 | 1.4400 |
| 90 | 0.0051 |
| 91 | 0.0038 |
| 92 | 0.0055 |
| 93 | 0.0029 |
| 94 | 0.0019 |
| 95 | 0.0065 |
| 96 | 0.0078 |
| 97 | 0.0026 |
| 98 | 0.0075 |
| 99 | 0.0358 |
| 100 | 0.0025 |
| 101 | 0.0030 |
| 102 | 0.0182 |
| 103 | 0.0048 |
| 106 | 0.0020 |
| 107 | 0.0019 |
| 108 | 0.0022 |
| 109 | 0.0027 |
| 110 | 0.0030 |
| 111 | 0.0043 |
| 112 | 0.0043 |
| 113 | 0.0043 |
| 114 | 0.0100 |
| 115 | 0.0186 |
| 116 | 0.0061 |
| 117 | 0.0030 |
| 118 | 0.0062 |
| 119 | 0.0034 |

Based on the abilities of a number of inhibitors to potently block *T. gondii* proliferation in mammalian cells, while demonstrating little or no off-target toxicity or hERG inhibition, the solubility in water and pharmacokinetic (PK) properties were examined (Table 2). The solubility of selected inhibitors was determined at pH=6.5. The initial PK profiles of these inhibitors were determined after a single 10 mg/kg oral dose in three Balb/c mice, with sampling conducted at the time points indicated in the Experimental Section. As a reference, after a 10 mg/kg po dose, previously reported inhibitor 3-(6-ethoxynaphthalen-2-yl)-1-((1-methylpiperidin-4-yl)methyl)-1H-pyrazolo[3,4-d]pyrimidin-4- amine (identified as compound 150 in US 2013/0018040, and hereafter) has a maximum concentration (Cmax) of 0.75±0.15 µM and total exposure (area under the plasma concentrations versus time curve, AUC) of 430±84 µM·min. For example Compounds of example 23-25, which all contain a 2-methylpropan-2-ol at the R2 position, are highly soluble and 24 and 25 reach maximum serum concentrations (Cmax)>10-fold higher and total exposure >30-fold higher than 1-(4-amino-3-(2-ethoxyquinolin-6-yl)-1H-pyrazolo[3,4-d]pyrimidin-1-yl)-2-methylpropan-2-ol previously reported compound 150 (Table 2 and FIG. 1).

TABLE 2

Solubility and PK properties of potent and selective TgCDPK1 inhibitors dosed at 10 mg/kg PO to mice.

| Ex. No. | Solubility (µM) | Tmax (min) | Cmax (µM) | AUCo->inf (µM · min) | Half life (min) | clearance (mL/min) |
|---|---|---|---|---|---|---|
| 22 | 17 | 30 | 0.88 ± 0.23 | 67 ± 60 | 50 ± 73 | 110 |
| 23 | >100 | 50 | 5.2 ± 1.0 | 850 ± 411 | 114 ± 115 | 0.2 |
| 24 | >100 | 320 | 13 ± 1 | 13700 ± 1500 | 1190 ± 510 | 0.2 |
| 25 | >100 | 560 | 7.8 ± 1.4 | 16600 ± 4300 | 1110 ± 400 | 0.3 |
| 26 | 6.2 | 40 | 0.39 ± 0.16 | 31 ± 8 | 40 ± 5 | 6.7 |
| 27 | 8.0 | 30 | 3.9 ± 1.1 | 3.9 ± 1.1 | 41 ± 21 | 21 |

Figure 2:
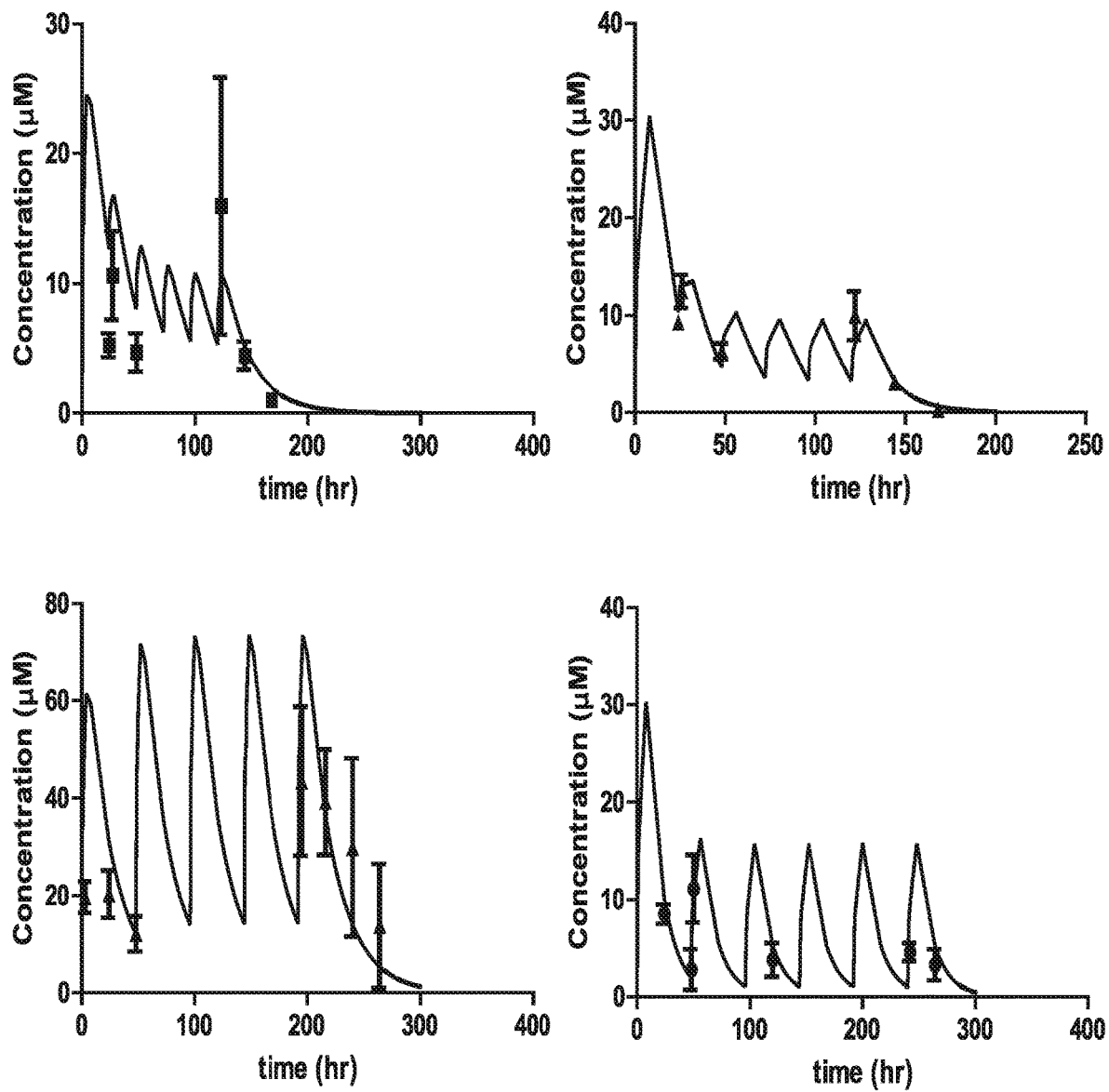
FIG. 2 shows multiple dose PK studies with compounds of Example 24 and 25. The dosing regimens were simulated based on the disposition data following single oral doses to mice (lines) and the observed plasma concentrations (dots) compared to the simulation. (top left panel) 24 was dosed at 20 mg/kg on day 1 and then 5 mg/kg every 24 hours for 5 doses. (bottom left panel) 24 was dosed at 50 mg/kg every 48 hours for 5 doses. (top right panel) 25 was dosed at 20 mg/kg on day 1 and then 5 mg/kg every 24 hours for 5 doses. (bottom right panel) 25 was dosed at 20 mg/kg on day 1 and then 10 mg/kg every 48 hours for 5 doses. Each dot is a mean of 3 mice with standard deviation.
Figure 3:
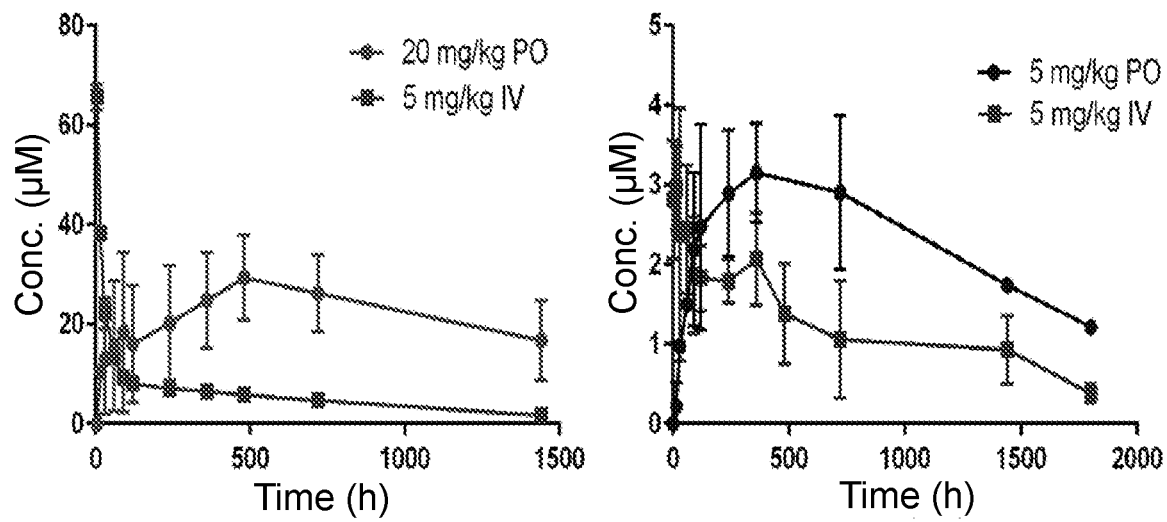
FIG. 3 shows plasma concentration time curves for (A) compound of Example 24 (left) and of Example 25 (right) following IV and PO dosing to rats; and (B) compound of Example 24 following IV and PO dosing to dogs (left) and monkeys (right).
Figure 3:
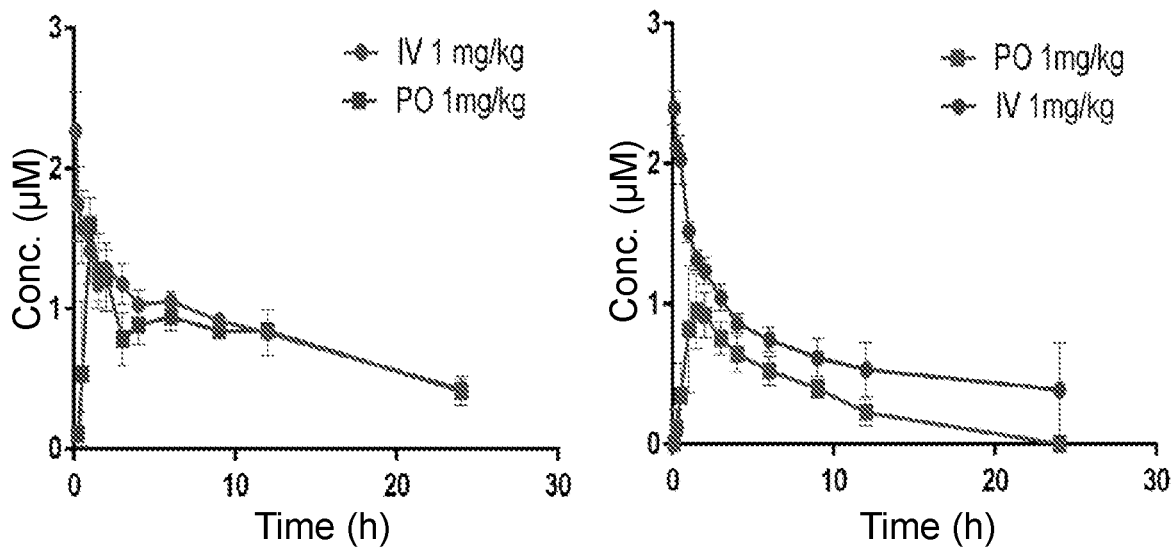

Based on the PK parameters of 24 and 25 following single dose administration to mice, these compounds were evaluated for tolerability following escalated dosing. Both compounds were initially dosed at 10 mg/kg on day one. As no observable adverse effects were detected in mice dosed with either 24 or 25, the next dose was increased to 50 mg/kg on day 4, followed by a final dose of 100 mg/kg on day 8. Mice showed no overt signs of toxicity or weight loss over the 10-day observation period. Next, the plasma protein binding of both compounds was evaluated. Both compounds were highly protein bound in mouse plasma with plasma protein binding of 96% for 24 and 88% for 25. Based on the protein binding values the plasma concentrations required to maintain unbound plasma exposure above the TgCDPK1 EC50 are 1.33 µM for 24 and 1.5 µM for 25. Based on these target concentrations and the single dose PK data, a multiple dosing regimen with a loading dose of 20 mg/kg of 24 and 25 followed by a 5 mg/kg daily dose for five days was evaluated. Blood was collected at multiple time points to determine plasma concentrations over the course of treatment (FIG. 2). Both compounds demonstrated excellent exposure through the 24-hour dosing interval with the trough concentrations remaining >1.5 µM throughout the study. The measured concentrations following multiple dosing were similar to those predicted from the single dose PK studies in mice (FIG. 3). Neither compound showed any evident signs of toxicity compared to mice dosed with vehicle only. Cardiac puncture blood collection was performed at the end of the study for complete blood count and serum biochemical profiles. All results were reported by Phoenix Central Laboratory to be within a normal range for species and age.

In a second multiple dose study compound 24 was administered at 50 mg/kg po every other day for 5 doses and compound 25 was administered with a 20 mg/kg loading dose followed by a 10 mg/kg maintenance dose every other day for 5 doses. The exposure to 25 with this dosing regimen was similar to the one observed with daily dosing of the lower dose and the plasma concentration at various time points were well predicted based on the single dose PK results. With compound 24 plasma concentrations remained >10 µM for the entire duration of the study (FIG. 2) with maximum concentrations reaching 43 µM. The exposure to compound 24 following the last 50 mg/kg dose was higher than predicted from single dose studies with longer half-life suggesting possible saturation of metabolism at this dose.

Based on the favorable single and multiple dose PK and the lack of observable toxicity, compounds 24 and 25 were evaluated for tolerability and PK characteristics in rats following intravenous (IV) and PO dosing. Following IV administration to rats both 24 and 25 displayed biphasic kinetics with compound 25 reaching distribution equilibrium more rapidly than 24. Compound 24 distributed approximately to total body water with a volume of distribution at steady state (Vss) of 0.9 L/kg. The distribution of 25 was more extensive with a Vss of 5.8 L/kg. Both compounds had very low systemic clearances in rats but, in contrast to mice, the clearance of 25 was 4-fold higher than that of 24. The elimination half-lives of both compounds were acceptable for multiple dosing regimens, 9.6 and 13 hours for 24 and 25, respectively (FIG. 3).

Following oral administration to rats both compounds showed slow absorption with absorption phase continuing for 12 hours after oral dosing. The plasma concentrations over the 24-hour period after PO dosing exceeded those observed after IV dosing (FIG. 3) suggesting that both 24 and 33 had essentially complete bioavailability in rats. The apparent bioavailability of these compounds was greatly improved compared to that of compound 150 (46%)

Because it is important that anti-toxoplasmosis therapies are able to prevent reactivation of parasites within tissue cysts, which largely reside in the central nervous system (CNS), the distribution of compounds 24 and 25 to the brain was next determined. To do this, the distribution of 24 and 25 into mouse brain (n=3) at one hr after intraperitoneal dosing of 5 mg/kg was measured. The mean concentration of compound 24 at one hour in brain was 1.2±0.5 µM, a concentration well above the TgCDPK1 $EC_{50}$. The corresponding plasma concentration of 24 was 4.1±1.1 µM resulting in a brain to plasma concentration ratio of 24 of 0.33±0.22. This brain penetration was comparable to compound 150 (0.31). In accordance with the larger distribution volume of compound 25, it demonstrated a greater brain to plasma concentration ratio (1.65±0.84). Both the brain and plasma concentration of 25, 1.90±0.24 µM and 1.23±0.76 µM, respectively, were above the TgCDPK1 $EC_{50}$.

Figure 4:
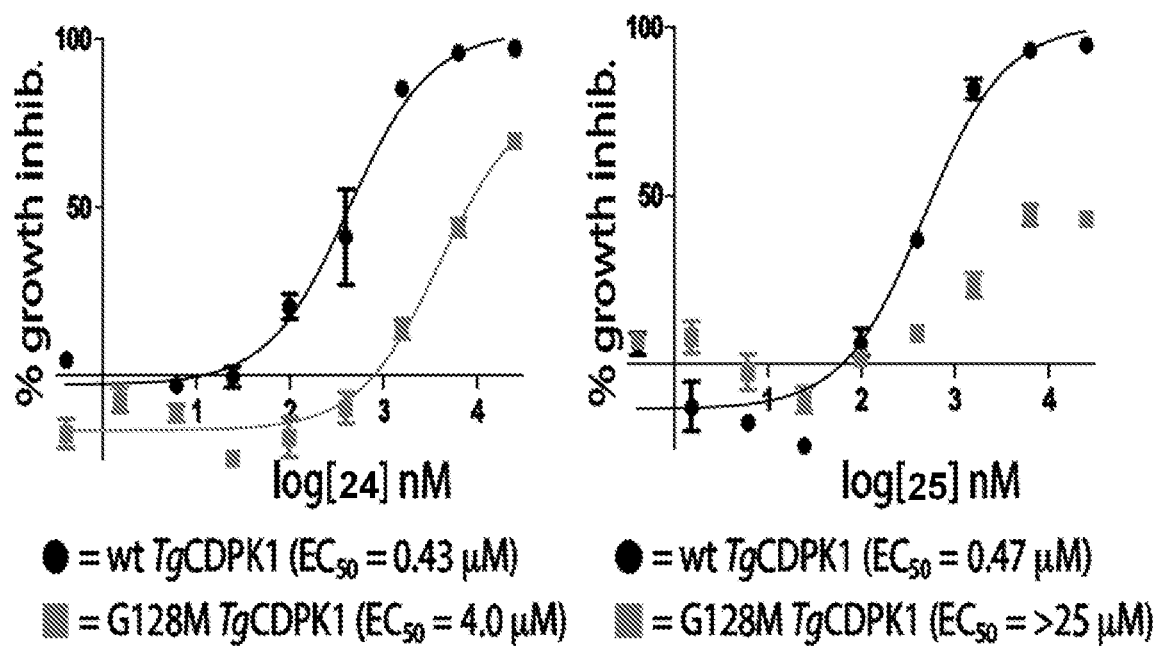
FIG. 4 shows $EC_{50}$ curves of inhibitors 24 (left) and 25 (right) for *T. gondii* over-expressing either wild type (wt) TgCDPK1 (black circles) or a drug resistant G128M TgCDPK1 mutant (gray squares). All experiments were performed in triplicate.

To demonstrate that TgCDPK1 is the kinase target of these compounds in *T. gondii*, 24 and 25 were tested against parasitic cell lines overexpressing the Gly128Met TgCDPK1 gatekeeper mutant or wildtype (wt) TgCDPK1. Expression of the Gly128Met gatekeeper mutant of TgCDPK1, but not wtTgCDPK1, makes *T. gondii* highly resistant to PP-based inhibitors that contain 6-alkoxynaphthalen-2-yl groups at the $R_3$ position. Both 24 and 25 show a dramatic loss in potency against parasites overexpressing the Gly128Met gatekeeper mutant relative to the parent RH strain and to *T. gondii* overexpressing wild type TgCDPK1 (FIG. 4), which is consistent with TgCDPK1 being the primary target through which these inhibitors exert their anti-parasitic effects. 24 and 25 were further profiled for any mammalian kinase off targets using a panel of 80 human kinases representing different subfamilies of the kinome tree with a fluorescence-based competition assay. 78 of the 80 mammalian kinases tested have an $IC_{50}$>1.5 µM (>1500-fold selective for TgCDPK1) for 24. For the two kinasesP-KCv (PKD3) and MEK1 that have sub-micromolar IC50 values, compound 24 is a >120-fold and >900-fold less potent inhibitor than for TgCDPK1, respectively. Compound 25 appears to be slightly more selective than compound 24. Compound 25 demonstrated an IC50 value of greater than 5 µM (>2500-fold selective) for 79 of the kinases tested, with only PKCv (PKD3) demonstrating a submicromolar ($IC_{50}$=0.280 µM; 140-fold selective) $IC_{50}$ value.

The lack of toxicity in the initial mouse toxicity screens allowed us to move forward into large animal pharmacokinetic and tolerability profiling. Male calves (n=2 for each compound) were dosed orally at 10 mg/kg for compound 24 and 9.3 mg/kg for compound 25 and blood sampled up to 12 days after dosing (results not shown). Similar to rats, the absorption of both compounds was slow with maximum concentrations reached at 24 hours for compound 24 and 12 hours for compound 25. The maximum plasma concentrations were similar for the two compounds, 7.9 µM and 9.8 µM, for compound 24 and 25, respectively. However, the overall exposure to 25 was greater than that of 24 due to its lower oral clearance and longer half-life (Table 3). Yet, both compounds had very low oral clearances and long systemic half-lives. Similar to rats, compound 25 had a higher apparent volume of distribution than compound 24 and the overall distribution characteristics were similar to those observed in rats.

TABLE 3

In vivo pharmacokinetic parameters of 24 and 25 in calves following PO administration of 10 mg/kg of 24 and 9.3 mg/kg of 25. Data are shown as the mean and range between animals.

| Ex. | AUC (h*µmol/L) | CL/F (mL/hr/kg) | V/F (L/kg) | t½ (hr) |
|---|---|---|---|---|
| 24 | 588 (353-825) | 52 (31-72) | 1.5 (1.3-1.8) | 23 (17-28) |
| 25 | 849 (607-1091) | 30 (22-39) | 2.3 (1.4-3.2) | 51 (46-56) |

Figure 5:
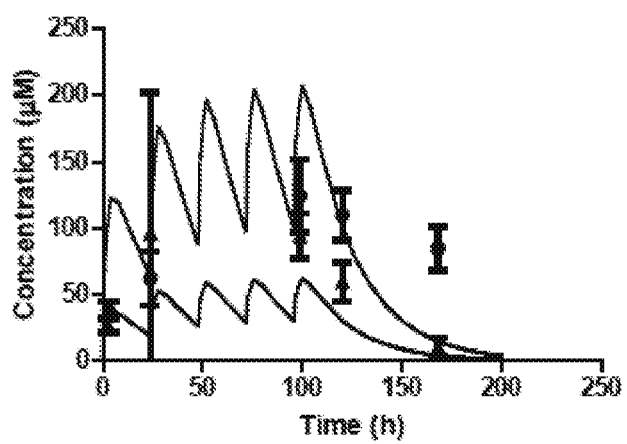
FIG. 5 shows exposure to compound of Example 24 in multiple dose toxicity studies. The concentration profiles of 24 following 30 mg/kg and 100 mg/kg daily doses were simulated based on the single dose 10 mg/kg data. The mean observed concentrations (n=3) with standard deviation are plotted as triangles for 30 mg/kg dosing and circles for the 100 mg/kg dosing) with the simulation.

Potential further toxicity of compound 24 was examined in mice by testing two doses (30 mg/kg and 100 mg/kg PO) daily for five days, while observing mice for signs of toxicity and collecting blood samples. Both groups of mice remained active, well groomed, and appeared normal throughout the study. Upon necropsy, there were no gross abnormalities. Histology revealed mild focal inflammation in the spleen in two of three mice in the 30 mg/kg group. The only abnormality seen in the 100 mg/kg group was inflammatory infiltrate in the hepatic lobules of the liver in one of three mice. The concentrations following 30 mg/kg doses were slightly higher than those predicted from single dose PK data while the exposures following the 100 mg/kg doses were similar to those predicted from single 10 mg/kg dose data (FIG. 5). Similar to the early multiple dosing experiments in mice, after the last 100 mg/kg dose the elimination of compound 24 was slower than predicted with considerable plasma concentrations persisting at 72 hours after the final dose.

Mice were then dosed with single PO doses of 24 ranging from 200 mg/kg to 1000 mg/kg. The lowest observable adverse effect level (LOAEL) was observed at 500 mg/kg and the no observable adverse effect level (NOAEL) was observed at 400 mg/kg. Mice had slightly ruffled fur and were less active than the control mice at 3 hours following the 500 mg/kg dose. The lowered activity persisted at 24 hours but was resolved by 30 hours. The lack of toxicity up to 500 mg/kg confirmed the safety of the compound for small animal efficacy studies.

The pharmacokinetics of 24 was further explored in dogs and monkeys following IV and PO administration. Similar to rats, 24 had a very low clearance in both species and a relatively long half-life (Table 4). The plasma concentrations time-profile following IV dosing was biphasic in both species with a similar extent of distribution in dogs and monkeys as observed in rats and calves (FIG. 3, panel B). The bioavailability of compound 24 was 66±17% in monkeys and 88±12% in dogs demonstrating good bioavailability in both species as predicted from rats.

TABLE 4

In vivo pharmacokinetic parameters of 24 following IV and PO administration of 1 mg/kg to dogs and monkeys (n = 3 for each). Data is show as mean and standard deviation.

| | AUC (h*µ mol/L) | CL (mL/hr/kg) | Vss (L/kg) | t½ (hr) |
|---|---|---|---|---|
| | Dog | | | |
| IV | 11200 ± 1100 | 90 ± 10 | 1.7 ± 0.1 | 13.2 |
| PO | 9620 ± 1350 | | | |
| | Monkey | | | |
| IV | 8720 ± 3400 | 130 ± 50 | 1.8 ± 0.3 | 9.6 |
| PO | 5730 ± 1500 | | | |

Figure 6:
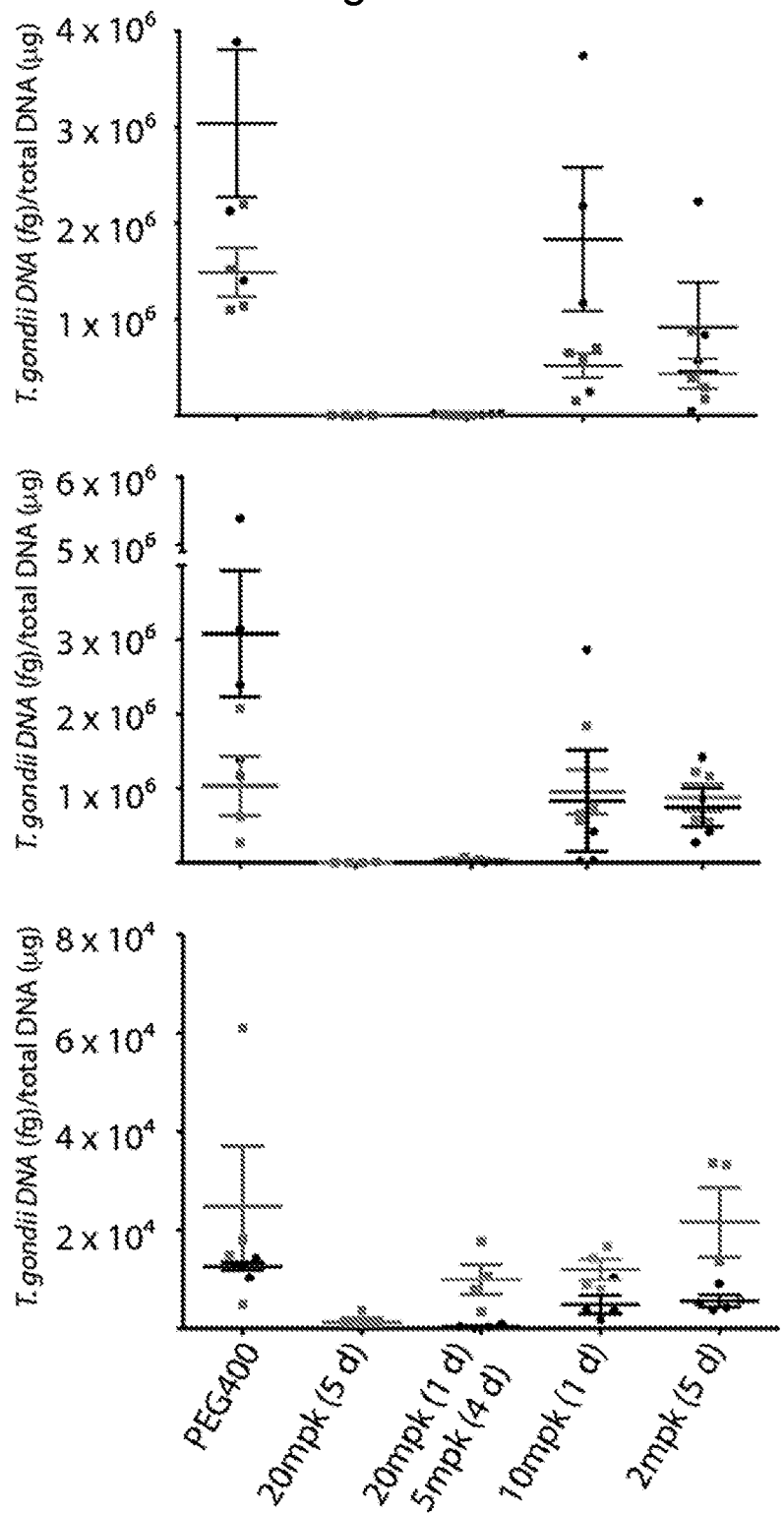
FIG. 6 shows activity of compound of Example 24 against acute toxoplasmosis. Efficacy was evaluated by measurement of *T. gondii* in peritoneal fluid (top), spleen (middle), and brain (bottom) in two experiments. Mice were treated daily for 5 days, beginning 2 days after IP infection with *T. gondii*. Mice were analyzed one day after the last dose. Peritoneal fluid was analyzed by fluorescent microscopy and spleen and brain tissue were analyzed by quantitative real-time PCR. Groups consisted of 4 mice. Bars represent the mean and the standard error of the mean. PEG=polyethylene glycol; mpk=mg/kg.

Example compound 24 was tested against a high inoculum of type 1 RH strain *T. gondii* to determine efficacy against fulminate toxoplasmosis in two experiments (FIG. 6). Unlike type 2 *T. gondii* strains, type 1 strains do not typically form tissue cysts but rather cause death in 5-10 days depending on the size of the inoculum. Compound 24 was administered via oral gavage two days after infection and the burden of infection was measured 5 days after the initiation of treatment. Treatment with 24 at 20 mg/kg for 5 days reduced the *T. gondii* in the peritoneal fluid below the limits of detection (less than 100 tachyzoites/mL). Treatment with 24 was highly effective at 20 mg/kg daily for 5 days in reducing infection in the spleen more than 99%, and infection in the brain 95%. The marked decrease in brain infection compared to controls coupled with the measurement of a sufficient brain concentrations of 24 suggest that this compound is active against actively replicating *T. gondii* in the brain, the target of current first-line anti-toxoplasma drugs. Previous mouse models of RH strain *T. gondii* in mice have detected *T. gondii* DNA in the brain after 2 days and recovery of *T. gondii* in culture at 4 days. In this study, decreases in brain infection may in part be due to efficacy against systemic infection. The favorable safety profile and brain permeability of 24 make it an attractive candidate to treat toxoplasmosis in pregnancy, as well as CNS toxoplasmosis.

Biological Example 8: *Sarcocystis Neurona* Calcium-Dependent Protein Kinase 1 is Targeted in Selective Therapeutic Development for Equine Protozoal Myeloencephalitis Equine protozoal myeloencephalitis (EMP) is a common progressive, degenerative neurological disease of the central nervous system caused by the apicomplexan parasite *Sarcocystis neurona*. Widespread therapeutic failure or relapses even with long term use of available treatments and absence of viable vaccines underscore the need to validate molecular targets within the parasite for new drug development based on novel scaffolds with desirable therapeutic outcome. We recently identified and sequenced an equivalent CDPK homologue (SnCDPK1) in *S. neurona* genome that has similar glycine "gatekeeper" residue. SnCDPK1 and TgCDPK1 have >85% amino acid identity. We have characterized BKIs for in vitro efficacy against SnCDPK1 and *S. neurona* merozoites. Recombinant SnCDPK1 was expressed, purified and screened against a selected group of BKIs previously shown to have low $IC_{50}$s against TgCDPK1 and *T. gondii* tachyzoites. Growth assays with a yellow fluorescent protein-expressing clone of *S. neurona* demonstrated that parasite growth was inhibited by BKIs at nanomolar concentrations (Table 4).

BKI-CDPK1 binding confirmation was performed using *S. neurona* lysates in thermal shift assays using CDPK1-specific antibody. SnCDPK1 was inhibited by low nM concentrations of BKIs. Analysis of *Sarcocystis* cell-inhibition data suggests that BKI interfered with an early step in *S. neurona* host cell invasion and egress processes. This presents molecular and phenotypic evidences that SnCDPK1 could be targeted for rational drug development as TgCDPK1 was previously validated for *T. gondii*. BKIs used in these assays have been chemically optimized with functional groups needed to improve potency, selectivity and pharmacokinetic properties. In vivo experiments were performed in murine model of infections using *Sarcocystis neurona* strain SN 37R. Experimental group treated with compound of Example 24 at a dose of 10 mg/kg/day/oral in drinking water having 0.5% Saccharine for 30 days showed no sign of disease relative to the control group 40 days after the end of treatment period.

Biological Example 9: Treatment of Non-Pregnant and Pregnant 248 Balb/c Mice Experimentally Infected with the *N. Caninum* Isolate The materials and methods for assessing treatment of *N. caninum* in vitro, and treats infected mice and rids of *N. caninum* infection in brain and fetuses has been previously described in Winzer et al. "In vitro and in vivo effects of the bumped kinase inhibitor 1294 in the related cyst-forming apicomplexans *Toxoplasma gondii* and *Neospora caninum*." Antimicrobial Agents and Chemotherapy 59(10):6361-74 (October 2015), incorporated herein by reference in its entirety.

Compound 150 is effective in treating *N. caninum* in vitro, and treats infected mice and rids of *N. caninum* infection in brain and fetuses. In addition, compound 24 has similar properties in that it is active in vitro against *N. caninum* cultures, and it treats pregnant mice removing *N. caninum* from their brains, their bodies, and their fetuses. A variety of other compounds have been found to be active against the presumed target, *N. caninum* calcium-dependent protein kinase 1 (cloned and expressed by our group and was also found to have a glycine gatekeeper residue), the compounds that are active against *T. gondii* CDPK1 are almost all uniformly active against NcCDPK1, and are presumed active in the in vitro and in vivo models as well.

Biological Example 10: *Besnoitia Besnoiti* Activity

Besnoitiosis is a chronic and debilitating bovine disease caused by the apicomplexan *Besnoitia besnoiti*, a protozoan parasite belonging to the group of cyst-forming coccidians. There are currently no therapeutic remedies for this disease. Apicomplexan calcium dependent protein kinases, necessary for host cell invasion and egress, are promising targets for drug development because orthologs are absent in mammalian genomes. Unlike the mammalian host cell kinases, BbCDPK1 has glycine at the entry to the ATP binding site (gatekeeper residue), which renders it sensitive to bumped kinase inhibitors (BKIs). The activity of two BKIs of the disclosure against *Besnoitia besnoiti* is provided in Table 5.

TABLE 4

In vitro activities against SnCDPK1.

| Example No. | SnCDPK1 $IC_{50}(\mu M)$ | $STDEV^{n=x}$ | *S. neurona* $EC_{50}$ ($\mu M$) | Thermal shift from DMSO |
|---|---|---|---|---|
| 24 | 0.0089 | $0.0015^{n=4}$ | 0.042 | 4.1 |
| 25 | 0.0075 | $0.0007^{n=2}$ | 0.128 | ND |
| (structure shown) | >2 | $0.3557^{n=3}$ | >10 | 0 |
| 150 | 0.0059 | $0.0005^{n=3}$ | 0.068 | 2.7 |

TABLE 5

In vitro activities against BbCDPK1 and *Besnoitia besnoiti*.

| Example | BbCDPK1 $IC_{50}$ (μM) | *B. besnoiti* $EC_{50}$ (μM) | *B. besnoiti* $EC_{100}$ (μM) |
|---|---|---|---|
| 150 | 0.004 | 0.045 | 2.580 |
| 24 | 0.005 | 0.097 | 3.590 |

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

What is claimed:

1. A compound of formula:

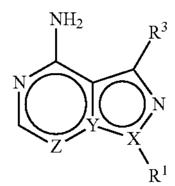

or a pharmaceutically acceptable salt thereof, wherein

X, Y, and Z are defined by either: (i) X is N, Y is C, and Z is N; or (ii) X is C, Y is N, and Z is C(H);

$R^1$ is $C_{2-6}$ alkyl, $C_{1-6}$ haloalkyl, —$C_{1-6}$ alkyl-$R^{12}$, $C_{3-8}$ cycloalkyl, heterocyclyl, heteroaryl, or aryl, wherein the alkyl, cycloalkyl, heterocyclyl, heteroaryl, and aryl groups are each optionally substituted with one or two $R^{11}$ groups;

each $R^{11}$ is independently halogen, cyano, nitro, $C_{1-6}$ alkyl, $C_{1-6}$ haloalkyl, —OR, —SR, —$NR_2$, —C(O)R, —C(O)OR, —C(O)$NR_2$, —$S(O)_2NR_2$, or —$S(O)_2R$;

and $R^{12}$ is —OR, —SR, —$NR_2$, —C(O)R, —C(O)OR, —C(O)$NR_2$, —$S(O)_2R$, —OC(O)R, —OC(O)OR, —OC(O)$NR_2$, —N(R)C(O)R, —N(R)C(O)OR, —N(R)C(O)$NR_2$, aryl, heteroaryl, $C_{3-8}$ cycloalkyl, or heterocyclyl, wherein $R^{12}$ is optionally substituted by one, two, or three groups that are each independently halogen, cyano, nitro, $C_{1-6}$ alkyl, $C_{1-6}$haloalkyl, $C_{1-6}$ hydoxyalkyl, —OR, —SR, —$NR_2$, —C(O)R, —C(O)OR, —C(O)$NR_2$, —$S(O)_2R$, —OC(O)R, —OC(O)OR, —OC(O)$NR_2$, —N(R)C(O)R, —N(R)C(O)OR, or —N(R)C(O)$NR_2$;

$R^3$ is one of the formulas,

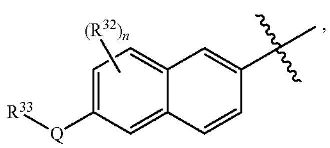

, or

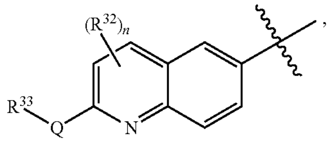

, wherein n is 0, 1, or 2;

Q is —O—, —S—, or —N($R^Q$)—, wherein $R^Q$ is hydrogen or $C_{1-6}$ alkyl; and $R^{33}$ is $C_{1-6}$ alkyl or ($C_{3-8}$ cycloalkyl)$C_{1-6}$ alkyl, wherein the alkyl and cycloalkyl are optionally substituted with one, two, three, or four groups that are each independently halogen, cyano, nitro, $C_{1-6}$ alkyl, $C_{1-6}$ haloalkyl, —$OR^{20}$, —$SR^{20}$, —$N(R^{20})_2$, —C(O)$R^{20}$, —C(O)O$R^{20}$, —C(O)N$(R^{20})_2$, —$S(O)_2R^{20}$, —OC(O)$R^{20}$, —OC(O)O$R^{20}$, —OC(O)N$(R^{20})_2$, —N($R^{20}$)C(O)$R^{20}$, —N($R^{20}$)C(O)O$R^{20}$, or —N($R^{20}$)C(O)N$(R^{20})_2$, wherein each $R^{20}$ is independently hydrogen or $C_{1-6}$ alkyl, each $R^{32}$ is independently halogen, cyano, nitro, $C_{1-6}$ alkyl, $C_{1-6}$ haloalkyl, —$OR^{34}$, —$SR^{34}$, —$N(R^{34})_2$, —C(O)$R^{34}$, —C(O)O$R^{34}$, —C(O)N$(R^{34})_2$, —$S(O)_2R^{34}$, —OC(O)$R^{34}$, —OC(O)O$R^{34}$, —OC(O)N$(R^{34})_2$, —N($R^{34}$)C(O)$R^{34}$, —N($R^{34}$)C(O)O$R^{34}$, or —N($R^{34}$)C(O)N$(R^{34})_2$, wherein each $R^{34}$ is independently hydrogen or $C_{1-6}$ alkyl; and each R is independently hydrogen, $C_{1-6}$ alkyl, $C_{2-6}$ alkenyl, $C_{1-6}$ haloalkyl, $C_{3-8}$ cycloalkyl, heterocyclyl, aryl, aryl$C_{1-6}$ alkyl, heteroaryl, or heteroaryl$C_{1-6}$ alkyl wherein the alkyl, aryl, arylalkyl, heteroaryl, and heteroarylalkyl are optionally substituted with one, two, three, or four groups that are each independently halogen, cyano, nitro, $C_{1-6}$ alkyl, $C_{1-6}$ haloalkyl, —$OR^0$, —$SR^0$, —$N(R^0)_2$, —C(O)$R^0$, —C(O)O$R^0$, —C(O)N$(R^0)_2$, —$S(O)_2R^0$, —OC(O)$R^0$, —OC(O)O$R^0$, —OC(O)N$(R^0)_2$, —N($R^0$)C(O)$R^0$, —N($R^0$)C(O)O$R^0$, or —N($R^0$)C(O)N$(R^0)_2$, wherein each $R^0$ is independently hydrogen or $C_{1-6}$ alkyl;

provided the compound is not:

1-(6-ethoxynaphthalen-2-yl)-3-isopropylimidazo[1,5-a]pyrazin-8-amine;

3-(6-isopropoxynaphthalen-2-yl)-1-isopropyl-1H-pyrazolo[3,4-d]pyrimidin-4-amine;

1-isopropyl-3-(6-propoxynaphthalen-2-yl)-1H-pyrazolo[3,4-d]pyrimidin-4-amine;

1-isopropyl-3-(6-methoxynaphthalen-2-yl)-1H-pyrazolo[3,4-d]pyrimidin-4-amine;

3-(6-ethoxynaphthalen-2-yl)-1-isopropyl-1H-pyrazolo[3,4-d]pyrimidin-4-amine;

3-(6-methoxynaphthalen-2-yl)-1-(piperidin-4-ylmethyl)-1H-pyrazolo[3,4-d]pyrimidin-4-amine;

3-(6-ethoxynaphthalen-2-yl)-1-(piperidin-4-ylmethyl)-1H-pyrazolo[3,4-d]pyrimidin-4-amine;

3-(6-ethoxynaphthalen-2-yl)-1-((1-methylpiperidin-4-yl)methyl)-1H-pyrazolo[3,4-d]pyrimidin-4-amine;

3-(6-isopropoxynaphthalen-2-yl)-1-(piperidin-4-ylmethyl)-1H-pyrazolo[3,4-d]pyrimidin-4-amine;

1-(piperidin-4-ylmethyl)-3-(6-propoxynaphthalen-2-yl)-1H-pyrazolo[3,4-d]pyrimidin-4-amine;

3-(6-(benzyloxy)naphthalen-2-yl)-1-(piperidin-4-ylmethyl)-1H-pyrazolo[3,4-d]pyrimidin-4-amine;

3-(6-butoxynaphthalen-2-yl)-1-(piperidin-4-ylmethyl)-1H-pyrazolo[3,4-d]pyrimidin-4-amine;

3-(6-(allyloxy)naphthalen-2-yl)-1-(piperidin-4-ylmethyl)-1H-pyrazolo[3,4-d]pyrimidin-4-amine;

3-(6-(2-chlorobenzyloxy)naphthalen-2-yl)-1-(piperidin-4-ylmethyl)-1H-pyrazolo[3,4-d]pyrimidin-4-amine;

3-(6-(3-chlorobenzyloxy)naphthalen-2-yl)-1-(piperidin-4-ylmethyl)-1H-pyrazolo[3,4-d]pyrimidin-4-amine;

3-(6-(4-chlorobenzyloxy)naphthalen-2-yl)-1-(piperidin-4-ylmethyl)-1H-pyrazolo[3,4-d]pyrimidin-4-amine;

3-(6-(benzyloxy)naphthalen-2-yl)-1-isopropyl-1H-pyrazolo[3,4-d]pyrimidin-4-amine;
3-(6-(allyloxy)naphthalen-2-yl)-1-isopropyl-1H-pyrazolo[3,4-d]pyrimidin-4-amine;
3-(6-butoxynaphthalen-2-yl)-1-isopropyl-1H-pyrazolo[3,4-d]pyrimidin-4-amine;
3-(6-isobutoxynaphthalen-2-yl)-1-isopropyl-1H-pyrazolo[3,4-d]pyrimidin-4-amine;
3-(6-isobutoxynaphthalen-2-yl)-1-(piperidin-4-ylmethyl)-1H-pyrazolo[3,4-d]pyrimidin-4-amine;
3-(6-(2-chlorobenzyloxy)naphthalen-2-yl)-1-isopropyl-1H-pyrazolo[3,4-d]pyrimidin-4-amine;
3-(6-(3-chlorobenzyloxy)naphthalen-2-yl)-1-isopropyl-1H-pyrazolo[3,4-d]pyrimidin-4-amine;
3-(6-(2,5-dimethylbenzyloxy)naphthalen-2-yl)-1-isopropyl-1H-pyrazolo[3,4-d]pyrimidin-4-amine;
1-isopropyl-3-(6-(2-methylbenzyloxy)naphthalen-2-yl)-1H-pyrazolo[3,4-d]pyrimidin-4-amine;
1-isopropyl-3-(6-(2-methyl-5-(trifluoromethyl)benzyloxy)naphthalen-2-yl)-1H-pyrazolo[3,4-d]pyrimidin-4-amine;
3-(6-(3-chloro-4-(2,2,2-trifluoroethyl)benzyloxy)naphthalen-2-yl)-1-isopropyl-1H-pyrazolo[3,4-d]pyrimidin-4-amine;
3-(6-(3-chloro-5-fluorobenzyloxy)naphthalen-2-yl)-1-isopropyl-1H-pyrazolo[3,4-d]pyrimidin-4-amine;
1-isopropyl-3-(6-(1-phenylethoxy)naphthalen-2-yl)-1H-pyrazolo[3,4-d]pyrimidin-4-amine;
3-(6-(4-tert-butylbenzyloxy)naphthalen-2-yl)-1-isopropyl-1H-pyrazolo[3,4-d]pyrimidin-4-amine;
1-isopropyl-3-(6-(pyridin-4-ylmethoxy)naphthalen-2-yl)-1H-pyrazolo[3,4-d]pyrimidin-4-amine;
3-(6-(4-chlorobenzyloxy)naphthalen-2-yl)-1-isopropyl-1H-pyrazolo[3,4-d]pyrimidin-4-amine;
6-(4-amino-1-(piperidin-4-ylmethyl)-1H-pyrazolo[3,4-d]pyrimidin-3-yl)-N,N-dimethylquinolin-2-amine;
3-tert-butyl-1-(6-ethoxynaphthalen-2-yl)imidazo[1,5-a]pyrazin-8-amine;
3-tert-butyl-1-(6-methoxynaphthalen-2-yl)imidazo[1,5-a]pyrazin-8-amine;
3-(6-ethoxynaphthalen-2-yl)-1-(1-ethylpiperidin-4-yl)-1H-pyrazolo[3,4-d]pyrimidin-4-amine;
3-(6-ethoxynaphthalen-2-yl)-1-(piperidin-4-yl)-1H-pyrazolo[3,4-d]pyrimidin-4-amine; or
3-(6-ethoxynaphthalen-2-yl)-1-(1-methylpiperidin-4-yl)-1H-pyrazolo[3,4-d]pyrimidin-4-amine.

2. The compound of claim 1, which is of the formula

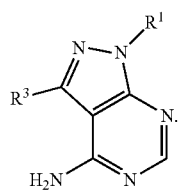

3. The compound of claim 1, wherein $R^3$ is of the formula

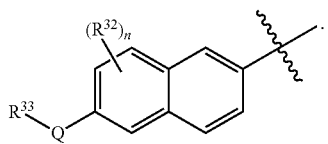

4. The compound of claim 1, wherein Q is —O—.

5. The compound of claim 1, wherein $R^1$ is $C_{2-6}$ alkyl or —$C_{1-4}$ alkyl-$R^{12}$.

6. The compound of claim 5, wherein $R^{12}$ is —OR or heterocyclyl, each optionally substituted.

7. A pharmaceutical composition comprising a compound of claim 1 and a pharmaceutically acceptable excipient, carrier, or diluent.

8. A method of treating an apicomplexan protozoan related disease, wherein the apicomplexan protozoan related disease is selected from toxoplasmosis, cryptosporidiosis, coccidiosis, malaria, neosporosis, sarcocystosis, besnoitiosis, coccidiosis, cystoisoporosis, babesiosis, and theileriosis, comprising administering to a patient in need of such treatment a therapeutically effective amount of (i) a compound of claim 1, or (ii) a pharmaceutical composition comprising such compound and a pharmaceutically acceptable excipient, carrier, or diluent.

9. The method of claim 8, wherein the apicomplexan protozoan related disease is selected from toxoplasmosis, cryptosporidiosis, coccidiosis, and malaria.

10. The method of claim 8, wherein the apicomplexan protozoan related disease is selected from toxoplasmosis or cryptosporidiosis.

11. A method of treating malaria comprising administering to a patient in need of such treatment a therapeutically effective amount of (i) a compound of claim 1 or (ii) a pharmaceutical composition comprising such compound and a pharmaceutically acceptable excipient, carrier, or diluent.

12. A method of treating an apicomplexan protozoan related disease, wherein the apicomplexan protozoan related disease is selected from toxoplasmosis, cryptosporidiosis, coccidiosis, malaria, neosporosis, sarcocystosis, besnoitiosis, coccidiosis, cystoisoporosis, babesiosis, and theileriosis, comprising administering to a patient in need of such treatment a therapeutically effective amount of a pharmaceutical composition comprising:
(i) a compound selected from
3-(6-ethoxynaphthalen-2-yl)-1-((1-methylpiperidin-4-yl)methyl)-1H-pyrazolo[3,4-d]pyrimidin-4-amine, or
3-(2-ethoxyquinolin-6-yl)-1-((1-methylpiperidin-4-yl)methyl)-1H-pyrazolo[3,4-d]pyrimidin-4-amine; and
(ii) a pharmaceutically acceptable excipient, carrier, or diluent selected from: calcium carbonate, sodium carbonate, lactose, calcium phosphate, sodium phosphate, starch or corn starch, alginic acid, gelatin, acacia, magnesium stearate, stearic acid, talc, glyceryl monostearate, glyceryl distearate, gelatin, kaolin, an oil medium, sodium carboxymethylcellulose, methylcellulose, hydropropyl-methylcellulose, sodium alginate, polyvinylpyrrolidone, gum tragacanth, gum acacia, lecithin, polyoxyethylene stearate, heptadecaethyleneoxycetanol, polyoxyethylene sorbitol monooleate, polyethylene sorbitan monooleate, glycerol, propylene glycol, sorbitol, glucose, sucrose, and combinations thereof, and optionally one or more preservative.

13. The method of claim 11, for treating neosporosis, sarcocystosis, besnoitiosis, cystoisoporosis, or theileriosis.

14. The method of claim 11, wherein the compound is 3-(6-ethoxynaphthalen-2-yl)-1-((1-methylpiperidin-4-yl)methyl)-1H-pyrazolo[3,4-d]pyrimidin-4-amine.

15. The method of claim 11, wherein the compound is 3-(2-ethoxyquinolin-6-yl)-1-((1-methylpiperidin-4-yl)methyl)-1H-pyrazolo[3,4-d]pyrimidin-4-amine.

16. A method of treating an apicomplexan protozoan related disease, wherein the apicomplexan protozoan related disease is selected from toxoplasmosis, cryptosporidiosis, coccidiosis, malaria, neosporosis, sarcocystosis, besnoitiosis, coccidiosis, cystoisoporosis, babesiosis, and theileriosis, comprising administering to a patient in need of such treatment one or more dosage units of a pharmaceutical composition comprising:
  (i) a compound selected from
    3-(6-ethoxynaphthalen-2-yl)-1-((1-methylpiperidin-4-yl)methyl)-1H-pyrazolo[3,4-d]pyrimidin-4-amine, or
    3-(2-ethoxyquinolin-6-yl)-1-((1-methylpiperidin-4-yl)methyl)-1H-pyrazolo[3,4-d]pyrimidin-4-amine,
  wherein the dosage of the compound in the dosage unit is 1 mg to 100 mg per kg of the patient; and
  (ii) a pharmaceutically acceptable excipient, carrier, or diluent.

17. The method of claim 16, for treating neosporosis, sarcocystosis, besnoitiosis, cystoisoporosis, or theileriosis.

18. The method of claim 16, wherein the compound is 3-(6-ethoxynaphthalen-2-yl)-1-((1-methylpiperidin-4-yl)methyl)-1H-pyrazolo[3,4-d]pyrimidin-4-amine.

19. The method of claim 16, wherein the compound is 3-(2-ethoxyquinolin-6-yl)-1-((1-methylpiperidin-4-yl)methyl)-1H-pyrazolo[3,4-d]pyrimidin-4-amine.

20. The method of claim 16, wherein the compound is present in a dosage of 5 mg/kg, 10 mg/kg, 20 mg/kg, or 50 mg/kg.

* * * * *